US011224620B2

(12) United States Patent
Bernalier-Donadille et al.

(10) Patent No.: US 11,224,620 B2
(45) **Date of Patent: *Jan. 18, 2022**

(54) COMPOSITIONS COMPRISING BACTERIAL STRAINS

(71) Applicant: 4D PHARMA PLC, Leeds (GB)

(72) Inventors: Annick Bernalier-Donadille, La Roche Blanc (FR); Laureen Crouzet, Beaumont (FR); Chloe Habouzit, Chamalieres (FR)

(73) Assignee: 4D PHARMA PLC, Leeds (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/743,212

(22) Filed: Jan. 15, 2020

(65) Prior Publication Data

US 2020/0323927 A1 Oct. 15, 2020

Related U.S. Application Data

(63) Continuation of application No. 16/022,484, filed on Jun. 28, 2018, now Pat. No. 10,583,158, which is a continuation of application No. 15/916,202, filed on Mar. 8, 2018, now Pat. No. 10,086,023, which is a continuation of application No. PCT/EP1017/025038, filed on Mar. 6, 2017.

(51) Int. Cl.

| | |
|---|---|
| ***A61K 35/74*** | (2015.01) |
| ***A61K 9/00*** | (2006.01) |
| ***A61K 35/741*** | (2015.01) |
| ***A61K 9/48*** | (2006.01) |
| ***A61K 9/19*** | (2006.01) |
| ***A61K 47/02*** | (2006.01) |
| ***A61K 47/10*** | (2017.01) |
| ***A61K 47/12*** | (2006.01) |
| ***A61K 47/26*** | (2006.01) |
| ***A61K 47/36*** | (2006.01) |
| ***A61K 47/38*** | (2006.01) |
| ***A61K 47/42*** | (2017.01) |
| ***A61P 1/00*** | (2006.01) |
| *A61K 35/00* | (2006.01) |

(52) U.S. Cl.

CPC ................ *A61K 35/74* (2013.01); *A61K 9/00* (2013.01); *A61K 9/19* (2013.01); *A61K 9/48* (2013.01); *A61K 9/4891* (2013.01); *A61K 35/741* (2013.01); *A61K 47/02* (2013.01); *A61K 47/10* (2013.01); *A61K 47/12* (2013.01); *A61K 47/26* (2013.01); *A61K 47/36* (2013.01); *A61K 47/38* (2013.01); *A61K 47/42* (2013.01); *A61P 1/00* (2018.01); *A61K 2035/11* (2013.01); *A61K 2035/115* (2013.01)

(58) Field of Classification Search

None

See application file for complete search history.

(56) References Cited

U.S. PATENT DOCUMENTS

| | | | | |
|---|---|---|---|---|
| 3,817,837 | A | 6/1974 | Rubenstein et al. | |
| 3,850,752 | A | 11/1974 | Schuurs et al. | |
| 3,939,350 | A | 2/1976 | Kronick et al. | |
| 3,996,345 | A | 12/1976 | Ullman et al. | |
| 4,275,149 | A | 6/1981 | Litman et al. | |
| 4,277,437 | A | 7/1981 | Maggio | |
| 4,366,241 | A | 12/1982 | Tom et al. | |
| 4,683,202 | A | 7/1987 | Mullis | |
| 4,816,567 | A | 3/1989 | Cabilly et al. | |
| 5,589,168 | A | 12/1996 | Allen et al. | |
| 5,599,795 | A | 2/1997 | McCann et al. | |
| 5,674,707 | A | 10/1997 | Hintz et al. | |
| 5,741,665 | A | 4/1998 | Kato et al. | |
| 5,925,657 | A | 7/1999 | Seed et al. | |
| 5,951,977 | A | 9/1999 | Nisbet et al. | |
| 6,348,452 | B1 | 2/2002 | Brown et al. | |
| 6,468,964 | B1 | 10/2002 | Rowe et al. | |
| 6,645,530 | B1 | 11/2003 | Borody | |
| 7,101,565 | B2 | 9/2006 | Monte | |
| 7,485,325 | B2 | 2/2009 | Swain | |
| 7,625,704 | B2 | 12/2009 | Fredricks et al. | |
| 7,749,494 | B2 * | 7/2010 | Renaud ..................... | A61P 1/00 424/93.4 |
| 7,998,474 | B2 | 8/2011 | Kelly | |
| 8,197,805 | B2 | 6/2012 | Lin et al. | |
| 8,287,932 | B2 | 10/2012 | Rosales et al. | |
| 8,460,648 | B2 | 6/2013 | Borody | |
| 8,557,233 | B2 | 10/2013 | MacSharry et al. | |
| 9,011,834 | B1 | 4/2015 | McKenzie et al. | |
| 9,314,489 | B2 | 4/2016 | Kelly et al. | |
| 9,371,510 | B2 | 6/2016 | Moore | |

(Continued)

FOREIGN PATENT DOCUMENTS

| | | | |
|---|---|---|---|
| CA | 2768301 | A1 | 1/2011 |
| CN | 1863540 | A | 11/2006 |

(Continued)

OTHER PUBLICATIONS

Advances in the Diagnosis and Treatment of Type 1 Diabetes, All About Fats—Development and Homeostasis, ADA-Funded Research, 2014, pp. A47-A48.
Ashish K. Marwaha et al., "TH17 cells in autoimmunity and immunodeficiency: protective or pathogenic?", Frontiers in Immunology, Jun. 2012, vol. 3, Article 129, pp. 1-8, Published online Jun. 4, 2012. Prepublished online Apr. 21, 2012.
Belkaid, Yasmine, and Timothy W Hand. "Role of the microbiota in immunity and inflammation." Cell vol. 157,1 (2014): 121-41. doi:10.1016/j.cell.2014.03.011,Mar. 27, 2014.
Chang H. Kim et al., "Gut Microbiota-Derived Short-Chain Fatty Acids, T Cells, and Inflammation", Immune Network vol. 14, No. 6: 277-288, Dec. 2014, Epub Dec. 22, 2014.

(Continued)

*Primary Examiner* — Padmavathi Baskar
(74) *Attorney, Agent, or Firm* — Wilson Sonsini Goodrich & Rosati

(57) ABSTRACT

The invention provides compositions comprising one or more bacterial strains for treating or preventing visceral hypersensitivity.

10 Claims, 19 Drawing Sheets

Specification includes a Sequence Listing.

(56) References Cited

U.S. PATENT DOCUMENTS

| | | | |
|---|---|---|---|
| 9,376,473 | B2 | 6/2016 | Gleiberman et al. |
| 9,539,293 | B2 | 1/2017 | Kelly et al. |
| 9,610,307 | B2 | 4/2017 | Berry et al. |
| 9,662,381 | B2 | 5/2017 | Honda et al. |
| 9,796,762 | B2 | 10/2017 | Kelly et al. |
| 9,808,519 | B2 | 11/2017 | Honda et al. |
| 9,839,655 | B2 | 12/2017 | Mulder et al. |
| 9,855,302 | B2 | 1/2018 | Gajewski et al. |
| 9,937,211 | B2 | 4/2018 | Kelly et al. |
| 9,974,815 | B2 | 5/2018 | Mulder et al. |
| 9,987,311 | B2 | 6/2018 | Mulder et al. |
| 10,046,015 | B2 | 8/2018 | Mulder et al. |
| 10,058,574 | B2 | 8/2018 | Grant et al. |
| 10,080,772 | B2 | 9/2018 | Crouzet et al. |
| 10,086,020 | B2 | 10/2018 | Bernalier-Donadille et al. |
| 10,086,021 | B2 | 10/2018 | Jeffery et al. |
| 10,086,022 | B2 | 10/2018 | Bernalier-Donadille et al. |
| 10,086,023 | B2 | 10/2018 | Bernalier-Donadille et al. |
| 10,183,046 | B2 | 1/2019 | Kelly |
| 10,226,489 | B2 | 3/2019 | Patterson et al. |
| 10,391,130 | B2 | 8/2019 | Grant et al. |
| 2003/0147858 | A1 | 8/2003 | Renaud et al. |
| 2004/0005304 | A1 | 1/2004 | Brudnak |
| 2004/0106564 | A1 | 6/2004 | Nilius et al. |
| 2006/0062774 | A1 | 3/2006 | Davis et al. |
| 2006/0073161 | A1 | 4/2006 | Breton |
| 2006/0115465 | A1 | 6/2006 | MacFarlane et al. |
| 2007/0167423 | A1 | 7/2007 | Bergauer et al. |
| 2007/0258953 | A1 | 11/2007 | Duncan et al. |
| 2007/0286913 | A1 | 12/2007 | Swain et al. |
| 2008/0069861 | A1 | 3/2008 | Brown et al. |
| 2008/0206212 | A1 | 8/2008 | McMahon et al. |
| 2008/0260906 | A1 | 10/2008 | Stojanovic |
| 2008/0299098 | A1 | 12/2008 | Se et al. |
| 2009/0217401 | A1 | 8/2009 | Korman et al. |
| 2010/0028449 | A1 | 2/2010 | Prakash et al. |
| 2010/0047209 | A1 | 2/2010 | Stanton et al. |
| 2010/0247489 | A1 | 9/2010 | Saur-Brosch |
| 2010/0284973 | A1 | 11/2010 | Schiffer-Mannioui et al. |
| 2010/0303782 | A1 | 12/2010 | Cobb et al. |
| 2010/0311686 | A1 | 12/2010 | Kasper et al. |
| 2010/0316617 | A1 | 12/2010 | Renaud et al. |
| 2011/0053829 | A1 | 3/2011 | Baumhof et al. |
| 2011/0086011 | A1 | 4/2011 | Kasper et al. |
| 2011/0280840 | A1 | 11/2011 | Blaser et al. |
| 2012/0020943 | A1 | 1/2012 | Lin |
| 2012/0107279 | A1 | 5/2012 | Arigoni et al. |
| 2013/0022575 | A1 | 1/2013 | Cassity |
| 2013/0130988 | A1 | 5/2013 | Blareau et al. |
| 2013/0195802 | A1 | 8/2013 | Moore |
| 2013/0280724 | A1 | 10/2013 | Ramadan et al. |
| 2013/0316032 | A1 | 11/2013 | Itoh et al. |
| 2013/0336931 | A1 | 12/2013 | Wadstroem et al. |
| 2014/0037716 | A1 | 2/2014 | Nowill et al. |
| 2014/0056852 | A1 | 2/2014 | Guglielmetti et al. |
| 2014/0112897 | A1 | 4/2014 | Pyne et al. |
| 2014/0147425 | A1 | 5/2014 | Henn et al. |
| 2014/0154218 | A1 | 6/2014 | Kohno et al. |
| 2014/0179770 | A1 | 6/2014 | Zhang et al. |
| 2014/0193464 | A1 | 7/2014 | Lin et al. |
| 2014/0199281 | A1 | 7/2014 | Henn et al. |
| 2014/0227227 | A1 | 8/2014 | Qin et al. |
| 2014/0328803 | A1 | 11/2014 | McKenzie et al. |
| 2014/0335131 | A1 | 11/2014 | Mazmanian et al. |
| 2014/0341921 | A1 | 11/2014 | Honda et al. |
| 2014/0363397 | A1 | 12/2014 | Allen-Vercoe et al. |
| 2015/0044173 | A1 | 2/2015 | Jones et al. |
| 2015/0071957 | A1 | 3/2015 | Kelly et al. |
| 2015/0104418 | A1 | 4/2015 | Flint et al. |
| 2015/0132264 | A1 | 5/2015 | Kelly et al. |
| 2015/0284781 | A1 | 10/2015 | Klumpp et al. |
| 2016/0058804 | A1 | 3/2016 | Jones et al. |
| 2016/0067188 | A1 | 3/2016 | Cade et al. |
| 2016/0184370 | A1 | 6/2016 | McKenzie et al. |
| 2016/0199424 | A1 | 7/2016 | Berry et al. |
| 2016/0223553 | A1 | 8/2016 | Sears et al. |
| 2016/0235792 | A1 | 8/2016 | Berry et al. |
| 2017/0143772 | A1 | 5/2017 | Mulder et al. |
| 2017/0143773 | A1 | 5/2017 | Mulder et al. |
| 2017/0143774 | A1 | 5/2017 | Mulder et al. |
| 2017/0143775 | A1 | 5/2017 | Mulder et al. |
| 2017/0319634 | A1 | 11/2017 | Grant et al. |
| 2017/0326202 | A1 | 11/2017 | Kelly |
| 2017/0354695 | A1 | 12/2017 | Grant et al. |
| 2017/0360856 | A1 | 12/2017 | Grant et al. |
| 2017/0368110 | A1 | 12/2017 | Grant et al. |
| 2018/0072778 | A1 | 3/2018 | Kelly et al. |
| 2018/0078585 | A1 | 3/2018 | Mulder et al. |
| 2018/0078587 | A1 | 3/2018 | Crott et al. |
| 2018/0133265 | A1 | 5/2018 | Stevenson |
| 2018/0207207 | A1 | 7/2018 | Bernalier-Donadille et al. |
| 2018/0207208 | A1 | 7/2018 | Jeffery et al. |
| 2018/0214496 | A1 | 8/2018 | Bernalier-Donadille |
| 2018/0221421 | A1 | 8/2018 | Bernalier-Donadille |
| 2018/0250346 | A1 | 9/2018 | Mulder et al. |
| 2018/0271918 | A1 | 9/2018 | Kelly et al. |
| 2018/0344780 | A1 | 12/2018 | Grant et al. |
| 2018/0369292 | A1 | 12/2018 | Bernalier-Donadille et al. |
| 2018/0369293 | A1 | 12/2018 | Jeffery et al. |
| 2019/0000892 | A1 | 1/2019 | Mulder et al. |
| 2019/0008908 | A1 | 1/2019 | Crouzet et al. |
| 2019/0015459 | A1 | 1/2019 | Grant et al. |
| 2019/0099458 | A1 | 4/2019 | Grant et al. |
| 2019/0134109 | A1 | 5/2019 | Mulder et al. |
| 2019/0151380 | A1 | 5/2019 | Grant et al. |
| 2019/0247448 | A1 | 8/2019 | Grant et al. |
| 2019/0255123 | A1 | 8/2019 | Jeffery et al. |

FOREIGN PATENT DOCUMENTS

| | | | |
|---|---|---|---|
| CN | 1917946 | A | 2/2007 |
| CN | 1954066 | A | 4/2007 |
| CN | 101590081 | A | 12/2009 |
| CN | 102304483 | A | 1/2012 |
| CN | 102031235 | B | 7/2012 |
| CN | 102093967 | B | 1/2013 |
| CN | 102905558 | A | 1/2013 |
| CN | 102940652 | A | 2/2013 |
| CN | 201180025408 | | 2/2013 |
| CN | 102373172 | B | 3/2013 |
| CN | 103037876 | A | 4/2013 |
| CN | 103142656 | A | 6/2013 |
| CN | 103146620 | A | 6/2013 |
| CN | 103156888 | A | 6/2013 |
| CN | 103652322 | A | 3/2014 |
| CN | 103781487 | A | 5/2014 |
| CN | 103820363 | A | 5/2014 |
| CN | 103849590 | A | 6/2014 |
| CN | 103865846 | A | 6/2014 |
| CN | 103930117 | A | 7/2014 |
| CN | 103981115 | A | 8/2014 |
| CN | 103981117 | A | 8/2014 |
| CN | 104160014 | A | 11/2014 |
| CN | 104195075 | A | 12/2014 |
| CN | 103509741 | B | 2/2015 |
| CN | 102940652 | B | 3/2015 |
| CN | 104435000 | A | 3/2015 |
| CN | 103037876 | B | 4/2015 |
| CN | 104546932 | A | 4/2015 |
| CN | 104546933 | A | 4/2015 |
| CN | 104546934 | A | 4/2015 |
| CN | 104546935 | A | 4/2015 |
| CN | 104546940 | A | 4/2015 |
| CN | 104546942 | A | 4/2015 |
| CN | 104560820 | A | 4/2015 |
| CN | 201410522408 | | 4/2015 |
| CN | 105112333 | A | 12/2015 |
| CN | 103820363 | B | 2/2016 |
| CN | 103865846 | B | 3/2016 |
| CN | 105982919 | A | 10/2016 |
| DE | 19826928 | A1 | 12/1999 |
| DE | 10206995 | A1 | 9/2003 |
| EP | 0120516 | A2 | 10/1984 |
| EP | 0238023 | A2 | 9/1987 |

(56) References Cited

FOREIGN PATENT DOCUMENTS

| | | | |
|---|---|---|---|
| EP | 0433299 | A1 | 6/1991 |
| EP | 0449375 | A2 | 10/1991 |
| EP | 0581171 | A1 | 2/1994 |
| EP | 0778778 | A1 | 6/1997 |
| EP | 0888118 | A1 | 1/1999 |
| EP | 1141235 | A2 | 10/2001 |
| EP | 1227152 | A1 | 7/2002 |
| EP | 1383514 | A1 | 1/2004 |
| EP | 1448995 | A1 | 8/2004 |
| EP | 1481681 | A1 | 12/2004 |
| EP | 1765391 | A1 | 3/2007 |
| EP | 1675481 | B1 | 11/2008 |
| EP | 1997499 | A1 | 12/2008 |
| EP | 1997905 | A1 | 12/2008 |
| EP | 1997906 | A1 | 12/2008 |
| EP | 1997907 | A1 | 12/2008 |
| EP | 2044436 | A2 | 4/2009 |
| EP | 2103226 | A1 | 9/2009 |
| EP | 2133088 | A3 | 1/2010 |
| EP | 1280541 | B2 | 3/2010 |
| EP | 2236598 | A1 | 10/2010 |
| EP | 2286832 | A1 | 2/2011 |
| EP | 2308498 | A1 | 4/2011 |
| EP | 2217253 | B1 | 6/2011 |
| EP | 1940243 | B1 | 8/2011 |
| EP | 2359838 | A1 | 8/2011 |
| EP | 1855550 | B1 | 10/2011 |
| EP | 1871400 | B1 | 10/2011 |
| EP | 2124972 | B1 | 6/2012 |
| EP | 1773361 | B2 | 9/2012 |
| EP | 1945234 | B1 | 12/2012 |
| EP | 2323493 | B8 | 12/2012 |
| EP | 2323494 | B8 | 12/2012 |
| EP | 1629850 | B2 | 5/2013 |
| EP | 2203551 | B1 | 8/2013 |
| EP | 2140771 | B1 | 12/2013 |
| EP | 2687227 | A1 | 1/2014 |
| EP | 2179028 | B1 | 8/2014 |
| EP | 2650002 | A4 | 8/2014 |
| EP | 2164349 | B1 | 9/2014 |
| EP | 2134835 | B1 | 10/2014 |
| EP | 2810652 | A2 | 12/2014 |
| EP | 2305838 | B1 | 1/2015 |
| EP | 2832859 | A1 | 2/2015 |
| ES | 2408279 | A2 | 6/2013 |
| JP | H08259450 | A | 10/1996 |
| JP | 2003261453 | A | 9/2003 |
| JP | 2005097280 | A | 4/2005 |
| JP | 2006265212 | A | 10/2006 |
| JP | 2007084533 | A | 4/2007 |
| JP | 2007116991 | A | 5/2007 |
| JP | 2008195635 | A | 8/2008 |
| JP | 2009507023 | A | 2/2009 |
| JP | 2010246523 | A | 11/2010 |
| JP | 5031249 | B2 | 9/2012 |
| JP | 2013005759 | A | 1/2013 |
| JP | 5183848 | B2 | 4/2013 |
| JP | 2013527240 | A | 6/2013 |
| JP | 2013201912 | A | 10/2013 |
| JP | 2014196260 | A | 10/2014 |
| JP | 2014534957 | A | 12/2014 |
| JP | 2015500792 | A | 1/2015 |
| JP | 5710876 | B2 | 4/2015 |
| JP | 5792105 | B2 | 10/2015 |
| KR | 100468522 | B1 | 1/2005 |
| KR | 20100128168 | A | 12/2010 |
| KR | 1020100128168 | | 12/2010 |
| KR | 101017448 | B1 | 2/2011 |
| KR | 101057357 | B1 | 8/2011 |
| KR | 20130021764 | A | 3/2013 |
| KR | 101250463 | B1 | 4/2013 |
| KR | 20140037544 | A | 3/2014 |
| KR | 20140061328 | A | 5/2014 |
| PL | 229020 | B1 | 5/2018 |
| RU | 2078815 | C1 | 5/1997 |
| TW | I417054 | B | 12/2013 |
| WO | WO-8807865 | A1 | 10/1988 |
| WO | WO-9117243 | A1 | 11/1991 |
| WO | WO-9611014 | A1 | 4/1996 |
| WO | WO-9720577 | A1 | 6/1997 |
| WO | WO-9730717 | A1 | 8/1997 |
| WO | WO-9735956 | A1 | 10/1997 |
| WO | WO-9843081 | A1 | 10/1998 |
| WO | WO-9855131 | A1 | 12/1998 |
| WO | WO-9857631 | A1 | 12/1998 |
| WO | WO-9919459 | A1 | 4/1999 |
| WO | WO-9942568 | A1 | 8/1999 |
| WO | WO-9945955 | A1 | 9/1999 |
| WO | WO-0116120 | A1 | 3/2001 |
| WO | WO-0158275 | A2 | 8/2001 |
| WO | WO-0185187 | A1 | 11/2001 |
| WO | WO-0193904 | A1 | 12/2001 |
| WO | WO-0207741 | A1 | 1/2002 |
| WO | WO-0242328 | A2 | 5/2002 |
| WO | WO-02070670 | A1 | 9/2002 |
| WO | WO-02085933 | A1 | 10/2002 |
| WO | WO-02094296 | A1 | 11/2002 |
| WO | WO-03010297 | A1 | 2/2003 |
| WO | WO-03022255 | A2 | 3/2003 |
| WO | WO-03045317 | A2 | 6/2003 |
| WO | WO-03046580 | A1 | 6/2003 |
| WO | WO-03053220 | A2 | 7/2003 |
| WO | WO-2004003235 | A3 | 6/2004 |
| WO | WO-2004085628 | A1 | 10/2004 |
| WO | WO-2005007834 | A1 | 1/2005 |
| WO | WO-2005030133 | A2 | 4/2005 |
| WO | WO-2005032567 | A2 | 4/2005 |
| WO | WO-2005058335 | A1 | 6/2005 |
| WO | WO-2005032567 | A3 | 7/2005 |
| WO | WO-2005093049 | A1 | 10/2005 |
| WO | WO-2005107381 | A2 | 11/2005 |
| WO | WO-2005121130 | A2 | 12/2005 |
| WO | WO-2006012586 | A2 | 2/2006 |
| WO | WO-2006033949 | A1 | 3/2006 |
| WO | WO-2006033950 | A1 | 3/2006 |
| WO | WO-2006033951 | A1 | 3/2006 |
| WO | WO-2006102350 | A1 | 9/2006 |
| WO | WO-2006102536 | A2 | 9/2006 |
| WO | WO-2006091103 | A3 | 10/2006 |
| WO | WO-2006110406 | A2 | 10/2006 |
| WO | WO-2006130205 | A1 | 12/2006 |
| WO | WO-2007027761 | A2 | 3/2007 |
| WO | WO-2007056218 | A2 | 5/2007 |
| WO | WO-2007064732 | A1 | 6/2007 |
| WO | WO-2007064749 | A1 | 6/2007 |
| WO | WO-2007098371 | A2 | 8/2007 |
| WO | WO-2007136719 | A2 | 11/2007 |
| WO | WO-2007140230 | A3 | 2/2008 |
| WO | WO-2008031438 | A3 | 5/2008 |
| WO | WO-2008055702 | A1 | 5/2008 |
| WO | WO-2008055703 | A2 | 5/2008 |
| WO | WO-2008064489 | A1 | 6/2008 |
| WO | WO-2008073148 | A2 | 6/2008 |
| WO | WO-2008076696 | A2 | 6/2008 |
| WO | WO-2008053444 | A3 | 7/2008 |
| WO | WO-2008083157 | A2 | 7/2008 |
| WO | WO-2008134450 | A2 | 11/2008 |
| WO | WO-2008153377 | A1 | 12/2008 |
| WO | WO-2009027753 | A1 | 3/2009 |
| WO | WO-2009030481 | A1 | 3/2009 |
| WO | WO-2009055362 | A1 | 4/2009 |
| WO | WO-2009059284 | A2 | 5/2009 |
| WO | WO-2009072889 | A1 | 6/2009 |
| WO | WO-2009079564 | A2 | 6/2009 |
| WO | WO-2009043856 | A3 | 7/2009 |
| WO | WO-2009080862 | A1 | 7/2009 |
| WO | WO-2009100331 | A2 | 8/2009 |
| WO | WO-2009116864 | A1 | 9/2009 |
| WO | WO-2009128949 | A2 | 10/2009 |
| WO | WO-2009138220 | A1 | 11/2009 |
| WO | WO-2009149149 | A1 | 12/2009 |
| WO | WO-2009151315 | A1 | 12/2009 |
| WO | WO-2009154463 | A2 | 12/2009 |
| WO | WO-2009156301 | A1 | 12/2009 |

(56) References Cited

FOREIGN PATENT DOCUMENTS

| | | | |
|---|---|---|---|
| WO | WO-2010002241 | A1 | 1/2010 |
| WO | WO-2010036876 | A2 | 4/2010 |
| WO | WO-2010037402 | A1 | 4/2010 |
| WO | WO-2010037408 | A1 | 4/2010 |
| WO | WO-2010037539 | A1 | 4/2010 |
| WO | WO-2010048481 | A1 | 4/2010 |
| WO | WO-2010063601 | A1 | 6/2010 |
| WO | WO-2010081126 | A3 | 9/2010 |
| WO | WO-2010129839 | A1 | 11/2010 |
| WO | WO-2010130659 | A1 | 11/2010 |
| WO | WO-2010130660 | A1 | 11/2010 |
| WO | WO-2010130662 | A1 | 11/2010 |
| WO | WO-2010130663 | A1 | 11/2010 |
| WO | WO-2010130697 | A1 | 11/2010 |
| WO | WO-2010130699 | A1 | 11/2010 |
| WO | WO-2010130700 | A1 | 11/2010 |
| WO | WO-2010130701 | A1 | 11/2010 |
| WO | WO-2010130702 | A1 | 11/2010 |
| WO | WO-2010130704 | A1 | 11/2010 |
| WO | WO-2010130710 | A1 | 11/2010 |
| WO | WO-2010130713 | A1 | 11/2010 |
| WO | WO-2010/143940 | A1 | 12/2010 |
| WO | WO-2010139531 | A1 | 12/2010 |
| WO | WO-2010142504 | A1 | 12/2010 |
| WO | WO-2010143961 | A1 | 12/2010 |
| WO | WO-2010147714 | A1 | 12/2010 |
| WO | WO-2010133475 | A3 | 1/2011 |
| WO | WO-2011000620 | A1 | 1/2011 |
| WO | WO-2011000621 | A1 | 1/2011 |
| WO | WO-2011005756 | A1 | 1/2011 |
| WO | WO-2010133472 | A3 | 2/2011 |
| WO | WO-2011020748 | A1 | 2/2011 |
| WO | WO-2011036539 | A1 | 3/2011 |
| WO | WO-2011043654 | A1 | 4/2011 |
| WO | WO-2011044208 | A1 | 4/2011 |
| WO | WO-2011058535 | A1 | 5/2011 |
| WO | WO-2011075138 | A1 | 6/2011 |
| WO | WO-2011096808 | A1 | 8/2011 |
| WO | WO-2011096809 | A1 | 8/2011 |
| WO | WO-2011110918 | A1 | 9/2011 |
| WO | WO-2011121379 | A1 | 10/2011 |
| WO | WO-2011149335 | A1 | 12/2011 |
| WO | WO-2011152566 | A2 | 12/2011 |
| WO | WO-2011153226 | A2 | 12/2011 |
| WO | WO-2011157816 | A1 | 12/2011 |
| WO | WO-2012012874 | A1 | 2/2012 |
| WO | WO-2012016287 | A2 | 2/2012 |
| WO | WO-2012024638 | A2 | 2/2012 |
| WO | WO-2011153226 | A3 | 3/2012 |
| WO | WO-2012055408 | A1 | 5/2012 |
| WO | WO-2012062780 | A1 | 5/2012 |
| WO | WO-2012071380 | A1 | 5/2012 |
| WO | WO-2012076739 | A1 | 6/2012 |
| WO | WO-2012105312 | A1 | 8/2012 |
| WO | WO-2012122478 | A1 | 9/2012 |
| WO | WO-2012140636 | A1 | 10/2012 |
| WO | WO-2012142605 | A1 | 10/2012 |
| WO | WO-2012145491 | A2 | 10/2012 |
| WO | WO-2012158517 | A1 | 11/2012 |
| WO | WO-2012165843 | A2 | 12/2012 |
| WO | WO-2012170478 | A2 | 12/2012 |
| WO | WO-2013005836 | A1 | 1/2013 |
| WO | WO-2013008039 | A2 | 1/2013 |
| WO | WO-2013008102 | A2 | 1/2013 |
| WO | WO-2013037068 | A1 | 3/2013 |
| WO | WO-2013050792 | A1 | 4/2013 |
| WO | WO-2013053836 | A1 | 4/2013 |
| WO | WO-2013063849 | A1 | 5/2013 |
| WO | WO-2013080561 | A1 | 6/2013 |
| WO | WO-2013124725 | A1 | 8/2013 |
| WO | WO-2013144701 | A1 | 10/2013 |
| WO | WO-2013153358 | A1 | 10/2013 |
| WO | WO-2013154725 | A1 | 10/2013 |
| WO | WO-2013171515 | A1 | 11/2013 |
| WO | WO-2013175038 | A1 | 11/2013 |
| WO | WO-2013181694 | A1 | 12/2013 |
| WO | WO-2013182038 | A1 | 12/2013 |
| WO | WO-2014001368 | A1 | 1/2014 |
| WO | WO-2014019271 | A1 | 2/2014 |
| WO | WO-2014020004 | A1 | 2/2014 |
| WO | WO-2014032108 | A1 | 3/2014 |
| WO | WO-2014036182 | A2 | 3/2014 |
| WO | WO-2014043593 | A2 | 3/2014 |
| WO | WO-2014053608 | A1 | 4/2014 |
| WO | WO-2014064359 | A1 | 5/2014 |
| WO | WO-2014067976 | A1 | 5/2014 |
| WO | WO-2014070014 | A1 | 5/2014 |
| WO | WO-2014070225 | A1 | 5/2014 |
| WO | WO-2014075745 | A1 | 5/2014 |
| WO | WO-2014078911 | A1 | 5/2014 |
| WO | WO-2014082050 | A1 | 5/2014 |
| WO | WO-2014093622 | A2 | 6/2014 |
| WO | WO-2014093635 | A1 | 6/2014 |
| WO | WO-2014093655 | A2 | 6/2014 |
| WO | WO-2014121298 | A2 | 8/2014 |
| WO | WO-2014121301 | A1 | 8/2014 |
| WO | WO-2014121302 | A2 | 8/2014 |
| WO | WO-2014121304 | A1 | 8/2014 |
| WO | WO-2014130540 | A1 | 8/2014 |
| WO | WO-2014137211 | A1 | 9/2014 |
| WO | WO-2014145958 | A2 | 9/2014 |
| WO | WO-2014150094 | A1 | 9/2014 |
| WO | WO-2014152338 | A1 | 9/2014 |
| WO | WO-2014153194 | A2 | 9/2014 |
| WO | WO-2014121302 | A3 | 10/2014 |
| WO | WO-2014167338 | A1 | 10/2014 |
| WO | WO-2014182966 | A1 | 11/2014 |
| WO | WO-2014200334 | A1 | 12/2014 |
| WO | WO-2014201037 | A2 | 12/2014 |
| WO | WO-2015003001 | A1 | 1/2015 |
| WO | WO-2015006355 | A2 | 1/2015 |
| WO | WO-2015013214 | A2 | 1/2015 |
| WO | WO-2015017625 | A1 | 2/2015 |
| WO | WO-2015021936 | A1 | 2/2015 |
| WO | WO-2015033305 | A1 | 3/2015 |
| WO | WO-2015038731 | A1 | 3/2015 |
| WO | WO-2015057151 | A1 | 4/2015 |
| WO | WO-2015077794 | A1 | 5/2015 |
| WO | WO-2015095241 | A2 | 6/2015 |
| WO | WO-2015077794 | A4 | 7/2015 |
| WO | WO-2015156419 | A1 | 10/2015 |
| WO | WO-2015156519 | A1 | 10/2015 |
| WO | WO-2015168534 | A1 | 11/2015 |
| WO | WO-2015169944 | A1 | 11/2015 |
| WO | WO-2015095241 | A4 | 12/2015 |
| WO | WO-2016019505 | A1 | 2/2016 |
| WO | WO-2016019506 | A1 | 2/2016 |
| WO | WO-2016033439 | A2 | 3/2016 |
| WO | WO-2016036615 | A1 | 3/2016 |
| WO | WO-2016057671 | A1 | 4/2016 |
| WO | WO-2016065324 | A1 | 4/2016 |
| WO | WO-2016069795 | A2 | 5/2016 |
| WO | WO-2016069801 | A1 | 5/2016 |
| WO | WO-2016070151 | A1 | 5/2016 |
| WO | WO-2016086161 | A1 | 6/2016 |
| WO | WO-2016086205 | A2 | 6/2016 |
| WO | WO-2016086206 | A1 | 6/2016 |
| WO | WO-2016086208 | A1 | 6/2016 |
| WO | WO-2016086209 | A1 | 6/2016 |
| WO | WO-2016086210 | A1 | 6/2016 |
| WO | WO-2016102950 | A1 | 6/2016 |
| WO | WO-2016102951 | A1 | 6/2016 |
| WO | WO-2016118730 | A1 | 7/2016 |
| WO | WO-2016139217 | A1 | 9/2016 |
| WO | WO-2016149449 | A1 | 9/2016 |
| WO | WO-2016149687 | A1 | 9/2016 |
| WO | WO-2016203218 | A1 | 12/2016 |
| WO | WO-2016203220 | A1 | 12/2016 |
| WO | WO-2017079450 | A1 | 5/2017 |
| WO | WO-2017085520 | A1 | 5/2017 |
| WO | WO-2017091753 | A1 | 6/2017 |
| WO | WO-2017148596 | A1 | 9/2017 |
| WO | WO-2017160711 | A1 | 9/2017 |
| WO | WO-2018011594 | A1 | 1/2018 |

(56) References Cited

FOREIGN PATENT DOCUMENTS

| | | | |
|---|---|---|---|
| WO | WO-2018047106 | A1 | 3/2018 |
| WO | WO-2018112363 | | 6/2018 |
| WO | WO-2018112363 | A1 | 6/2018 |
| WO | WO-2018112365 | A2 | 6/2018 |
| WO | WO-2018215782 | A1 | 11/2018 |

OTHER PUBLICATIONS

Chika Kasai et al., "Comparison of the gut microbiota composition between obese and non-obese individuals in a Japanese population, as analyzed by terminal restriction fragment length polymorphism and next-generation sequencing", BMC Gastroenterology (2015)15:100, pp. 1-10, Aug. 11, 2015.

Communication of a notice of opposition to European Patent EP3240554. May 13, 2020, 50 pages.

Drancourt, Michel et al., "16S Ribosomal DNA Sequence Analysis of a Large Collection of Environmental and Clinical Unidentifiable Bacterial Isolates", Journal of Clinical Microbiology, Oct. 2000, 3623-3630.

GenBank Accession No. AB196512.1, *Ruminococcus productus* gene for 16S rRNA, accessed Apr. 16, 2020.

Helena S. Domingues et al., "Functional and Pathogenic Differences of Th1 and Th17 Cells in Experimental Autoimmune Encephalomyelitis", PLoS ONE, Nov. 2010, vol. 5, Issue 11, e15531, pp. 1-13, Published online Nov. 29, 2010.

Hui Yan et al., "Dietary Fat Content and Fiber Type Modulate Hind Gut Microbial Community and Metabolic Markers in the Pig", PLOS ONE, Apr. 2013, vol. 8, Issue 4, e59581, pp. 1-10, Epub Apr. 3, 2013.

Justesen, Ulrik Stenz et al., "16S rRNA Gene Sequencing in Routine Identification of Anaerobic Bacteria Isolated from Blood Cultures", Journal of Clinical Microbiology, vol. 48, No. 3, Mar. 2010, p. 946-948, 0095-1137/10/$12.00 doi:10.1128/JCM.02075-09, Epub Jan. 13, 2010.

Llosa, Nicolas J. et al., "Interleukin-17 and type 17 helper T cells in cancer management and research", Immuno Targets and Therapy, 2014:3, 39-54, Published online Mar. 10, 2014.

Matthias Lochner et al., "The special relationship in the development and function of T helper 17 and regulatory T cells", Prog Mol Biol Transl Sci, 2015, 136:99-129. (33 pages). Epub Aug. 18, 2015.

M. Touyama et al., "Quantification of Blautia wexlerae and Blautia luti in human faeces by real-time PCR using specific primers", Beneficial Microbes: 6 (4)—pp. 583-590, Published Online: Apr. 22, 2015.

Jan. 17, 2019 Notice of Allowance for U.S. Appl. No. 15/803,721.

Dec. 21, 2018 Notice of Allowance U.S. Appl. No. 15/700,700.

Jan. 30, 2019 Notice of Corrected Allowability for U.S. Appl. No. 15/803,721.

Jan. 30, 2019 Final Rejection for U.S. Appl. No. 15/842,635.

Feb. 1, 2019 Non-Final Office Action U.S. Appl. No. 16/040,356.

Mar. 4, 2019 Final Office Action for U.S. Appl. No. 15/704,245.

4d Pharma Plc: "Clinical Update—RNS—London Stock Exchange", Jul. 19, 2016.

4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].

Ahanchian, Hamic, A multi-strain synbiotic may reduce viral respiratory infections in asthmatic children: a randomized controlled trial; Sep. 2016, vol. 8, Issue 9, pp. 2833-2839, DOI: http://dxdoi.or/10.19082/2833.

Alp, G., and Aslim, B. (2010). Relationship between the resistance to bile salts and low pH with exopolysaccharide (EPS) production of *Bifidobacterium* spp. isolated from infants feces and breast milk. Anaerobe 16(2), 101-105. doi: 10.1016/j.anaerobe.2009.06.006. Epub Jul. 2, 2009.

Altschul et al. 'Basic local alignment search tool.' Journal of Molecular Biology. 1990, vol. 215, No. 3, pp. 403-410. Oct. 5, 1990.

"Amedei, A. et al. Multiple sclerosis: the role of cytokines in pathogenesis and in therapies. Int J Mol Sci. Oct. 19, 2012;13(10):13438-60. doi: 10.3390/ijms131013438."

Aminov et al. Molecular diversity, cultivation, and improved detection by fluorescent in situ hybridization of a dominant group of human gut bacteria related to *Roseburia* spp. or *Eubacterium rectale*. Applied and environmental microbiology. 2006, vol. 72, No. 9, pp. 6371-6376.

An et al. (1985) "New cloning vehicles for transformation of higher plants," EMBO J. 4:277-284. Feb. 1, 1985.

An et al. (1988) "Binary Vectors," Plant Molecular Biology Manual. A3:1-19.

An et al. Transformation of Tobacco, Tomato, Potato, and *Arabiodopsis thaliana* Using a Binary Ti Vector System,Plant Physiol. May 1986; 81:301-305. Published May 1986.

Anonymous: "4D pharma's Blautix for Irritable Bowel Syndrome shows positive impact—pharmaceutical daily news", Dec. 13, 2016.

Appleyard, Caroline B. et al., Pretreatment with the probiotic VSL#3 delays transition from inflammation to dysplasia in rate model of colitis-associated cancer; Am J. Physiol. Gastrointest. Liver Physiol. 301:G1004-G1013, 2011, Sep. 8, 2011:DOI:10.1152.ajpg.00167.2011.

Archer et al. (1997) "The Molecular Biology of Secreted Enzyme Production by Fungi," Critical Reviews Biotechnology. 17(4):273-306.

Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92. Sep. 1, 1996.

Atarashi et al. Induction of colonic regulatory T cells by indigenous *Clostridium* species. Science 331(6015):337-341 (2011). Epub Dec. 23, 2010.

Atarashi et al., Th17 Cell Induction by Adhesion of Microbes to Intestinal Epithelial Cells. CELL, vol. 163, No. 2, Oct. 8, 2015. pp. 367-380.

Atarashi, et al., Treg induction by a rationally selected mixture of Clostridia strains from the human microbiota. Supplementary Information. Nature 500, 232-236 (Aug. 8, 2013) doi:10.1038/nature12331.

Atarashi, K. et al., Treg induction by a rationally selected mixture of Clostridia strains from the human microbiota. Nature. 2013; 500(7461):232-236. Epub Jul. 10, 2013.

ATCC Catalog, https://www.atcc.org/search_results.aspx?dsNav=Ntk:primarysearch%7cbacteroides+thetaiotaomicron%7c3%7c,Ny:true,ro:0,N:1000552&searchterms=bacteroides+thetaiotaomicron&redir=1, Accessed on May 2, 2018.

Auriel, E. et al., "Chapter 38—Nonsteroidal anti-inflammatory drugs exposure and the central nerous system", 2014, Handbook of Clinical Neurology 119, 577-584.

Ausubel et al. (1999) Short Protocols in Molecular Biology. 4th edition. pp. 7-58 to 7-60, and Chapter 18. pp. 18-1 to 18-23.

Awadel-Kariem, Mustafa et al., First report of Parabacteroides goldsteinii bacteraemia in a patient with complicated intra-abdominal infection, Anaerobe, vol. 16, Issue 3, Jun. 2010, pp. 223-225. Epub Feb. 6, 2010.

Azad, M.B. et al., Probiotic supplementation during pregnancy or infancy for the prevention of asthma and wheeze: systematic review and meta-analysis BMJ 2013; 347 :f6471. Dec. 4, 2013.

Aziz, R.K., Bartels, D., Best, A.A., DeJongh, M., Disz, T., Edwards, R.A., et al. (2008). The RAST Server: Rapid Annotations using Subsystems Technology. BMC Genomics 9, No. 1, 75. doi: 10.1186/1471-2164-9-75. Published: Feb. 8, 2008.

Bagge, et al., Diversity of spore-forming bacteria in cattle manure, slaughterhouse waste and samples from biogas plants. Journal of applied microbiology. 2010;109: 1549-1565. Epub Jul. 13, 2010.

Balato, et al., Effects of adalimumab therapy in adult subjects with moderate-to-severe psoriasis on Th17 pathway. (2014) J Eur Acad Dermatol Venereol. 28(8):1016-24. Epub Sep. 4, 2013.

Banfield, J. & Murphy, K.R., Non-Th2, Late-onset, non-allergic asthma. Copd & Asthma for NPs, A peer-reviewed newsletter, Aug. 2016; 14: 8 Pages.

(56) References Cited

OTHER PUBLICATIONS

Barcenilla, et al. Phylogenetic relationships of butyrate-producing bacteria from the human gut. Appl Environ Microbiol. Apr. 2000. 66(4):1654-61.
Barry, et al., Criteria for Disksusceptibility tests and quality control guidelines for the cefoperazone-sulbactam combination, Journal of clinical microbiology, Jan. 1988;26(1):13-17.
Beaucage, et al. Deoxynucleoside phosphoramidites—A new class of key intermediates for deoxypolynucleotide synthesis. Tetrahedron Letters, vol. 22, 1981, pp. 1859-1869.
Beggs (1978) "Transformation of yeast by a replicating hybrid plasmid," Nature. 275:104-109. Published: Sep. 1, 1978.
Begley, M., Hill, C., and Gahan, C.G.M. (2006). Bile Salt Hydrolase Activity in Probiotics. Applied and Environmental Microbiology 72(3), 1729-1738. doi: 10.1128/AEM.72.3.1729-1738.2006.
Berg et al. (1996) "Enterocolitis and colon cancer in interleukin-10-deficient mice are associated with aberrant cytokine production and CD4(+) TH1-like responses," The Journal of Clinical Investigation. 98(4):1010-1020. Aug. 15, 1996.
Berger, B., Moine, D., Mansourian, R., and Arigoni, F. (2010). HspR Mutations Are Naturally Selected in Bifidobacterium longum When Successive Heat Shock Treatments Are Applied. Journal of Bacteriology 192(1), 256-263. doi: 10.1128/jb.01147-09.
Berger, S. Gideon guide to medically important bacteria. Gideon E-book Series. 2017 edition. 4 pages.
Bergonzelli, G.E., Granato, D., Pridmore, R.D., Marvin-Guy, L.F., Donnicola, D., and Corthesy-Theulaz, I.E. (2006). GroEL of Lactobacillus johnsonii La1 (NCC 533) is cell surface associated: potential role in interactions with the host and the gastric pathogen Helicobacter pylori. Infect Immun 74(1), 425-434. doi: 10.1128/IAI.74.1.425-434.2006.
Bernalier, A., et al., "Diversity of H2/C02-utilizing acetogenic Bacteria from Feces of Non-Methane-Producing Humans", Current Microbiology vol. 33 (Aug. 1996), pp. 94-99, Springer-Vertag New York Inc., USA.
Bernalier et al., "Acetogenesis from H02 and C0-2 by Methane and Non-Methane-Producing Human Colonic Bacterial Communities" Fems Microbiology Ecology. vol. 19. No. 3. 1996. pp. 193-202. XP000979130.
Bernalier et al. *Ruminococcus hydrogenotrophicus* sp. nov., a new H2/CO2-utilizing acetogenic bacterium isolated from human feces. 1996 Arch. Microbiol. 166 (3), 176-183. Sep. 1996.
Bertram, J. et al. Establishment of a cloned line of Lewis lung carcinoma cells adapted to cell culture. (1980) Cancer let. 11:63-73.
Blandino, G., Fazio, D., DiMarco, R. Probiotics: Overview of microbiological and immunological characteristics (2008). Expert Review of Anti-Infective Therapy, 6 (4), pp. 497-508.
Bond, John H., Jr., et al., "Factors Influencing Pulmonary Medicine Excretion in Man: An indirect method of studying the in situ metabolism of the methane-producing colonic bacteria"; Journal of Experimental Medicine, Oct. 29, 1970, pp. 572-388.
Born, P., et al., English Abstract "Carbohydrate substitutes: comparative study of intestinal absorption of fructose, sorbitol and xylitol", "Zuckeraustauschstoffe: Vergleichende Untersuchung zur intestinalen Resorption von Fructose, Sorbit und Xylit", Medizinische Klinik 89, Technischen Universitat Munchen (Munich) Nov. 15, 1994; 89 (11): 575-8 (Article in German), Urban & Vogel, Munich, Germany.
Born, P., et al., "Fecal bacterial activity in symptomatic carbohydrate malabsorption: Effect on the fecal short-chain fatty acid ratio", intervention during the week "Digestive Diseases Week" from May 16 to May 19, 1999, Orlando, Z. Gasteroenterol2000: 38:623-626, Georg Thieme Verlag Stuttgart, New York, USA.
Bottacini, et al., Comparative genomics of the Bifidobacterium brevetaxon. BMC Genomics, 2014; 15:170. DOI:10.1186/1471-1471-2164-15-170. Published: Mar. 1, 2014.
Bottacini, F., Morrissey, R., Esteban-Torres, M., James, K., van Breen, J., Dikareva, E., et al. (2018). Comparative genomics and genotype-phenotype associations in Bifidobacterium breve. Scientific Reports 8(1), 10633. doi: 10.1038/S41598-018-28919-4. Published: Jul. 13, 2018.
Bourassa, Megan W et al. "Butyrate, neuroepigenetics and the gut microbiome: Can a high fiber diet improve brain health?." Neuroscience letters vol. 625 (2016): 56-63. doi:10.1016/j.neulet.2016.02.009. Jun. 20, 2016.
Brand et al., Collagen-induced arthritis, 2007; Protocol 2(5):1269-1275.
Brasel et al. (2000) "Generation of murine dendritic cells from ftl3-ligand-supplemented bone marrow cultures," Blood. 96(9):3029-3039.
Bravo, Javier A. et al., "Ingestion of Lactobacillus strain regulates emotional behavior and central GABA receptor expression in a mouse via the vagus nerve", PNAS Sep. 20, 2011 108 (38) 16050-16055; https://doi.org/10.1073/pnas.1102999108.
Bressa, et al., Differences in gut microbiota profile between women with active lifestyle and sedentary women. Plos One, 2017; 12(2): 1-20. Feb. 10, 2017.
Brook, I., Clinical Review: Bacteremia caused by anaerobic bacteria in children. Critical Care 6(3): 7 pages (2002). Published online May 9, 2002.
Bry et al. A model of host-microbial interactions in an open mammalian ecosystem. Science 273(5280):1380-1383 (1996). Sep. 6, 1996.
Buffie et al., Precision microbiome restoration of bile acid-mediated resistance to Clostridium difficile. Nature, 517(7533):205-208 (2015). Published online Oct. 22, 2014.
Busing, K. et al., Effects of oral Enterococcus faecium strain DSM 10663 NCIMB 10415 on diarrhoea patterns and performance of sucking piglets. Benef Microbes. Mar. 2015;6(1):41-4. doi: 10.3920/BM2014.0008.
Butcher et al. (1980) The role of tissue culture in the study of crown-gall tumorigenesis. Tissue Culture Methods for Plant Pathologists. Eds.: Ingrams, D. S.; Helgeson, J.P. pp. 203-208.
"Campeau, J.L. et al., Intestinal Epithelial Cells Modulate Antigen-Presenting Cell Responses to Bacterial DNA. Infectionand Immunity. Aug. 2012; 80(8): 2632-2644."
Candela et al. 'Interaction of probiotic Lactobacillus and Bifidobacterium strains with human intestinal epithelial cells:Adhesion properties, competition against enteropathogens and modulation of IL-8 production'. International Journal of Food Microbiology. 2008, vol. 125, No. 3, pp. 286-292. Epub Apr. 30, 2008.
Candela, M., Bergmann, S., Vici, M., Vitali, B., Turroni, S., Eikmanns, B.J., et al. (2007). Binding of human plasminogen to Bifidobacterium. J Bacteriol 189(16), 5929-5936. doi: 10.1128/JB.00159-07. Epub Jun. 8, 2007.
Candela, M., Biagi, E., Centanni, M., Turroni, S., Vici, M., Musiani, F., et al. (2009). Bifidobacterial enolase, a cell surface receptor for human plasminogen involved in the interaction with the host. Microbiology 155(Pt 10), 3294-3303. doi: 10.1099/mic.0.028795-0. Epub Jul. 2, 2009.
Candela, M., Centanni M Fau—Fiori, J., Fiori J Fau—Biagi, E., Biagi E Fau—Turroni, S., Turroni S Fau—Orrico, C., Orrico C Fau—Bergmann, S., et al. (2010). DnaK from *Bifidobacterium animalis* subsp. *lactis* is a surface-exposed human plasminogen receptor upregulated in response to bile salts. Microbiology 156(6), 1609-1618.
Carlson, Greg C. "Glutamate receptor dysfunction and drug targets across models of autism spectrum disorders." Pharmacology, biochemistry, and behavior vol. 100,4 (2012): 850-4. doi:10.1016/j.pbb.2011.02.003. Epub Feb. 16, 2011.
Caruthers, et al. New chemical methods for synthesizing polynucleotides. Nucleic Acids Symp Ser. 1980;(7):215-23.
Carvalho et al. (Jan. 2011) "TLR5 activation induces secretory interleukin-1 receptor antagonist (sll-1 Ra) and reduces inftammasome-associated tissue damage," Nature. 4(1 ):102-111.
Casey et al. 'Isolation and characterization of anti-*Salmonella lactic* acid bacteria from the porcine gastrointestinal tract'. Letters in Applied Microbiology. 2004, vol. 39, No. 5, pp. 431-438.
Caspi, P.R. Experimental autoimmune uveoretinitis in the rat and mouse. Curr Protoc Immunol. May 2003;Chapter 15:Unit 15.6. doi: 10.1002/0471142735.im1506s53.

(56) References Cited

OTHER PUBLICATIONS

Cekanaviciute, et al., Gut bacteria from multiple sclerosis patients modulate human T cells and exacerbate symptoms in mouse models. PNAS. Received for review Jun. 30, 2017; 1-6. Oct. 3, 2017 114 (40) 10713-10718; first published Sep. 11, 2017.
Cereghino et al. (2000) "Heterologous protein expression in the methylotrophic yeast Pichia pastoris," FEMS Microbiol Review. 24(1 ):45-66.
Charriot, et al., Future treatment for ashtma, Eur Respir Rev 2016; 25: 77-92.
Cheluvappa, R. et al., T helper type 17 pathway suppression by appendicitis and appendectomy protects against colitis. Clin Exp Immunol. Feb. 2014;175(2):316-22. doi: 10.1111/cei.12237.
Chen, S. et al., Live combined bacillus subtilis and enterococcus faecium ameliorate murine experimental colitis by immunosuppression. International journal of inflammation. 2014(878054). 7 Pages. Published online Sep. 8, 2014.
Chevreux et al. 'Genome sequence assembly using trace signals and additional sequence information.' German Conference on Bioinformatics. 1999.
Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.
Chi, W. et al. Upregulated IL-23 and IL-17 in Behçet patients with active uveitis. Invest Ophthalmol Vis Sci. Jul. 2008;49(7):3058-64. doi: 10.1167/iovs.07-1390.
Chiu, et al., Monocolonization of germ-free mice with bacteroides fragilis protects against dectran sulfate sodium-induced acute colitis. Biomed Research International 2014. vol. 2014. Article ID 675786. 9 Pages. May 29, 2014.
Choji Kaneuchi et al., "*Clostridium coccoides*, a New Species from the Feces of Mice", International Journal of Systematic Bacteriology, vol. 26, No. 4, Oct. 1976, p. 482-486.
Chothia et al. The relation between the divergence of sequence and structure in proteins. EMBO Journal. 1986, 5(4):823-826.
Christiaen, S.E., O'Connell Motherway, M., Bottacini, F., Lanigan, N., Casey, P.G., Huys, G., et al. (2014). Autoinducer-2 plays a crucial role in gut colonization and probiotic functionality of Bifidobacterium breve UCC2003. PLoS One 9(5), e98111. doi: 10.1371/journal.pone.0098111. Published: May 28, 2014.
Christmann, et al., Human seroreactivity to gut microbiota antigens. J Allergy Clin Immunol 136(5):1378-1386; available online May 23, 2015.
Christou (1994) "Genetic engineering of crop legumes and cereals: current status and recent advances," Agro-Food Industry Hi-Tech. pp. 17-27.
Chung et al. 'Microbiota-stimulated immune mechanisms to maintain gut homeostasis.' Current Opinion in Immunology. 2010, vol. 22, No. 4, pp. 455-460. Epub Jul. 23, 2010.
Cintas LM, Casaus MP, Herranz C, Nes IF, Hernandez PE. Review: bacteriocins of lactic acid bacteria (2001). Food Sci Technol 7(4):281-305.
Claesson, et al. Gut microbiota composition correlates with diet and health in the elderly. 2012. Nature, 488, 178-184. Published: Jul. 13, 2012.
Clarridge III, J.E. Impact of 16S rRNA gene sequence analysis for identification of bacteria on clinical microbiology and infectious diseases (2004). Clinical Microbiology Reviews, 17 (4), pp. 840-862.
Clinical Trials for Thetanix, EU Clinical Trials Register, Date of commencement of clinical trial: Oct. 16, 2015. Available at: https://clinicaltrialsregister.eu/ctr-search/search?query=Thetanix.
Coakley M et al: Intestinal bifidobacteria that produce trans-9, trans-11 conjugated linoleicacid: A fatty acid with antiproliferative activity against human colon SW480and HT-29 cancer cells, Nutrition and Cancer, Taylor & Francis Group, US vol. 56, No. 1, Jan. 1, 2006 (Jan. 1, 2006), pp. 95-102, XP008087265, ISSN: 0163-5581, DOI:10.1207/515327914NC5601 13 cf. abstract, p. 101, last para. of the right-hand col.
Colin, et al., GIC-1001, a Clinical Stage, Orally Administered Colonic Analgesic Drug Proposed as a Cost-Effective Alternative to I.V. Sedation Used in Colonoscopy. Canadian Digestive Diseases Week, 2014; 2 pages.
Collins, M.D., et al., *Enterococcus avium* nom. rev., comb, nov.; *E. casseliflavus* nom. rev., comb, nov.; *E. durans* nom. rev., comb, nov.; *E. gallinarum* comb, nov.; and *E. malodoratus* sp. nov. (1984) Int J Syst Evol Microbiol. 34: 220-223. First Published: Apr. 1, 1984.
Constantinescu, Cris S et al. "Experimental autoimmune encephalomyelitis (EAE) as a model for multiple sclerosis (MS)." British journal of pharmacology vol. 164,4 (2011): 1079-106. doi:10.1111/j.1476-5381.2011.01302.x.
Co-pending U.S. Appl. No. 15/359,144, filed Nov. 22, 2016.
Co-pending U.S. Appl. No. 15/916,205, filed Mar. 8, 2018.
Co-pending U.S. Appl. No. 16/206,250, filed Nov. 30, 2018.
Co-pending U.S. Appl. No. 16/240,644, filed Jan. 4, 2019.
Co-pending U.S. Appl. No. 16/247,834, filed Jan. 15, 2019.
Cotter, P.O., Hill, C., Ross, R.P. Food microbiology: Bacteriocins: Developing imlate immunity for food (2005). Nature Reviews Microbiology, 3 (10), pp. 777-788.
Coughenour LL et al., "A new device for the rapid measurement of impaired motor function in mice", Pharmacol Biochem Behav. Mar. 1977;6(3):351-3.
Crawley, Jacqueline N. "Translational animal models of autism and neurodevelopmental disorders." Dialogues in clinical neuroscience vol. 14,3 (2012): 293-305. . Sep. 2012.
Crellin et al. (2005) "Human CD4+ T cells express TLR5 and its ligand ftagellin enhances the suppressive capacity and expression of FOXP3 in CD4+CD25+ T regulatory cells," Journal of Immunology. 175(12):8051-8059.
Cronin, M., Knobel, M., O'Connell-Motherway, M., Fitzgerald, G.F., and van Sinderen, D. (2007). Molecular Dissection of a Bifidobacterial Replicon. Applied and Environmental Microbiology 73(24), 7858-7866.
Cryan JF and Mombereau C., "In search of a depressed mouse: utility of models for studying depression-related behavior in genetically modified mice", Mol Psychiatry. Apr. 2004;9(4):326-57.
Cryan, John F, and Timothy G Dinan. "More than a gut feeling: the microbiota regulates neurodevelopment and behavior." Neuropsychopharmacology : official publication of the American College of Neuropsychopharmacology vol. 40,1 (2015): 241-2. doi:10.1038/npp.2014.224. Jan. 2015.
Cummings, M., Breitling, R., and Takano, E. (2014). Steps towards the synthetic biology of polyketide biosynthesis. Fems Microbiology Letters 351(2), 116-125. doi: 10.1111/1574-6968.12365. Epub Jan. 7, 2014.
Dahya V. et al., Clostridium ramosum Osteomyelitis in an immunocompetent patient after traumatic injury, Infectious Diseases in Clinical Practice 20150312 Lippincott Williams and Wilkins USA, vol. 23, No. 2, Mar. 12, 2015, pp. 102-104, XP009193312, ISSN: 1056-9103 the whole document.
Daniel Garrido et al., "Utilization of galactooligosaccharides by *Bifidobacterium longum* subsp. *infantis* isolates", Food Microbiology, 33 (2013) 262-270. Published online Oct. 22, 2012.
Daniele, Stefano G et al. "Activation of MyD88-dependent TLR1/2 signaling by misfolded α-synuclein, a protein linked to neurodegenerative disorders." Science signaling vol. 8,376 ra45. May 12, 2015, doi:10.1126/scisignal.2005965.
Darfeuille-Michaud et al. High prevalence of adherent-invasive *Escherichia coli* associated with ileal mucosa in Crohn's disease. .2004. Gastroenterology 127(2):412-21.
Darlington, G.J., Liver Cell Lines. (1987) Meth Enzymol. 151:19-38.
Database UniProt [Online] Jun. 1, 2003 (Jun. 1, 2003), "subname:Full= possible pirin family protein {ECO:0000313|EMBL:AAO75294. 1};", XP00275366,retrieved from EBI accession No. UNIPROT:Q8ABC3 Database accession No. Q8ABC3.
Database WPI, Week Jan. 2018, Thomson Scientific, London, GB; AN 2017-834299, XP002787097, & WO 2017/209156 Al (Morinaga Milk Ind Co. LTD) Dec. 7, 2017 (Dec. 7, 2017) * abstract * of WO2017/2019156, Kobayashi, Youdai et al.

(56) References Cited

OTHER PUBLICATIONS

Database WPI,Week Jan. 2018, Thomson Scientific, London, GB; AN 2017-834299, XP002787097,& WO 2017/209156 Al (Morinaga Milk Ind Co Ltd) Dec. 7, 2017 (Dec. 7, 2017) * abstract*.
Davis et al. (1970) "Genetic and Microbiological Research Technqiues," Methods Enzymol. 17A:79-143.
Day, John G., McLellan, Mark R., "Cryopreservation and Freeze-Drying Protocols" Methods in Molecular Biology, 2007.
De Paepe et al. 'Trade-off between bile resistance and nutritional competence drives *Escherichia coli* diversification in the mouse gut.' PLoS Genetics. 2011, vol. 7, No. 6, e1002107. Published: Jun. 16, 2011.
De Ruyter, P.G., Kuipers, O.P., and de Vos, W.M. (1996). Controlled gene expression systems for Lactococcus lactis with the food-grade inducer nisin. Applied and Environmental Microbiology 62(10), 3662-3667.
Deangelis, M., et al., Selection of potential probiotic lactobacilli from pig feces to be used as additives in pelleted feeding (2006). Research in Microbiology, 157 (8), pp. 792-801. Epub Jun. 23, 2006.
Delgado, S., Ruiz, L., Hevia, A., Ruas-Madiedo, P., Margolles, A., and Sánchez, B. (2018). "Evidence of the In Vitro and In Vivo Immunological Relevance of Bifidobacteria," in the Bifidobacteria and Related Organisms.), 295-305.
Demarche, et al., Detailed analysis of sputum and systemic inflammation in asthma phenotypes: are paucigranulocytic asthmatics really non-inflammatory?, BMC Pulmonary Medicine, 2016; (16)46: 1-13. Published: Apr. 5, 2016.
Dennis et al. 'DAVID: database for annotation, visualization, and integrated discovery.' Genome Bioi. 2003, vol. 4, No. 5, pp. 3. Published: Aug. 14, 2003.
Desbonnet L et al., "Gut microbiota depletion from early adolescence in mice: Implications for brain and behaviour", Brain Behav Immun. Aug. 2015;48:165-73. doi: 10.1016/j.bbi.2015.04.004. Epub Apr. 10, 2015.
Dheeraj Mohania et al., "Modulation of expression of Programmed Death-1 by administration of probiotic Dahi in DMH-induced colorectal carcinogenesis in rats", Acta Biomed 2013; 84:102-109.
Distrutti, et al., 5-Amino-2-hydroxybenzoic Acid 4-(5-Thioxo-5H-[1,2]dithiol-3yl)-phenyl Ester (ATB-429), a Hydrogen Sulfide-Releasing Derivative of Mesalamine, Exerts Antinociceptive Effects in a Model of Postinflammatory Hypersensitivity. The Journal of pharmacology and experimental therapeutics, 2006;319(1):447-458. Epub Jul. 19, 2006.
Distrutti, et al., Gut Microbiota role in irritable bowel syndrome: New therapeutic strategies. World Journal of Gastroenterology. Feb. 21, 2016; 22(7): p. 2219-2241, XP002769875.
Distrutti, et al., Hydrogen sulphide induces u opioid receptor-dependent analgesia in a rodent model of visceral pain. Molecular Pain, 2010; 6(36):1-16.
Divyashri et al. Probiotic attributes, antioxidant, anti-inflammatory and neuromodulatory effects of Enterococcus faecium CFR 3003: in vitro and in vivo evidence. (2015) J Med Microbiol, doi: 10.1099/jmm.0.000184. Dec. 2015;64(12):1527-1540. Epub Oct. 7, 2015.
DMSZ: Opening of Ampoules and Rehydration of Dried Cultures; (http://web.archive.org/web/20000 52411541 O/www.dsmz.de/open. htm); updated of website on Mar. 2000.
Dong, H., Rowland I Fau—Yaqoob, P., and Yaqoob, P. (2012). Comparative effects of six probiotic strains on immune function in vitro. Br J Nutr 108(3), 459-470. doi: 10.1017/S0007114511005824. Epub Nov. 7, 2011.
Dong-Hyun Kim and Young-Ho Jin, "Intestinal Bacterial B-Glucuronidase Activity of Patients with Colon Cancer", Arch Pharm Res vol. 24, No. 6, 564-567, 2001.
Drago, Lorenzo et al., Immunodulatory Effects of Lactobucillus salivarius LS01 and Bifidobacterium breve, Alone and in Combination on Peripheral Blood Mononuclear Cells of Allergic Asthmatics; Allergy Asthma Immunol. Res. Jul. 2015: 7(4):409-413. Published online Mar. 18, 2015.
Duck et al. 'Isolation of flagellated bacteria implicated in Crohn's disease.' Inflammatory Bowel Diseases. 2007, vol. 13, No. 10, pp. 1191-1201.
Duncan et al. (2002) "*Roseburia intestinalis* sp. nov., a novel saccharolytic, butyrate-producing bacterium from human faeces," International Journal Systematic Evolutionary Microbiology. 52:1615-1620.
Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441. First Published: Oct. 1, 2006.
Duncan et al. "Lactate-utilizing bacteria, isolated from human feces, that produce butyrate as a major fermentation product" Applied and environmental microbiology. 2004, vol. 70, No. 10, pp. 5810-5817.
Duncan, et al. *Roseburia intestinalis* sp. nov., a novel saccharolytic, butyrate-producing bacterium from human faeces. Int J Syst Evol Microbiol. Sep. 2002;52(Pt 5):1615-20.
Durand et al., "Reductive Acetogenesis in Animal and Human Gut." Physiological and Clinical Aspects of Short-Chain Fatty Acids, 1995. pp. 107-117, XP000979817 Cambridge University Press ISBN 0-521-44048-3.
Eckburg, PB. et al., Diversity of the human intestinal microbial flora.Science. Jun. 10, 2005;308(5728):1635-8. Epub Apr. 14, 2005.
Elhenawy et al., Preferential packing of acidic glycosidases and proteases into bacteroides Outer membrane vesicles. mBio 5:e00909-14, pp. 1-12, 2014.
Elkins et al. 'Genes encoding bile salt hydrolases and conjugated bile salt transporters in Lactobacillus johnsonii 100-100 and other *Lactobacillus* species.' Microbiology. 2001, vol. 147, No. 12, pp. 3403-3412.
Elmadfa, 1., Klein, P., Meyer, AL. Immune-stimulating effects oflactic acid bacteria in vivo and in vitro (2010). Proceedings of the Nutrition Society, 69 (3), pp. 416-420. Epub Jun. 16, 2010.
Ely et al. (2000) "A family of six flagellin genes contributes to the Caulobacter crescentus flagellar filament," Journal of Bacteriology. 182(17):5001-5004.
Embl sequence AAO75294.1 (2003)—provided within the Office Action dated Feb. 16, 2018 in U.S. Appl. No. 15/631,952. 2 Pages.
Eren, A. Murat et al., "A single genus in the gut microbiome reflects host preference and specificity," The ISME Journal (2015) 9, 9-100 (2015).
ESR Dated Dec. 17, 2018, Appl. 18189521.0.
Estelle Devillard et al., Metabolism of Linoleic Acid by Human Gut Bacteria: Different Routes for Biosynthesis of Conjugated Linoleic Acid, Journal of Bacteriology, Mar. 2007, vol. 189, No. 6, pp. 2566-2570. Epub Jan. 5, 2007.
European Communication dated Jun. 14, 2017 for EP Application No. 15817513.3.
Evelo Biosciences, Inc. Clinical Trials (Rank 1): A Study of EDP1503 in Patients With Colorectal Cancer, Breast Cancer, and Checkpoint Inhibitor Relapsed Tumors, https://clinicaltrials.gov/ct2/show/NCT03775850?spons=evelo&rank=1, 2018, accessed on Feb. 4, 2019.
Evelo Biosciences, Inc. Clinical Trials (Rank 2): A Study of EDP1815 in Healthy Participants and Participants With Mild to Moderate Psoriasis and Atopic Dermatitis, https://clinicaltrials.gov/ct2/show/NCT03733353?spons=evelo&rank=2, 2018, accessed on Feb. 4, 2019.
Evelo Biosciences, Inc. Clinical Trials (Rank 3): A Study of EDP1066 in Healthy Participants and Participants With Mild to Moderate Psoriasis and Atopic Dermatitis, https://clinicaltrials.gov/ct2/show/NCT03542994?spons=evelo&rank=3, 2018, accessed Feb. 4, 2019.
Evelo Biosciences, Inc. Clinical Trials (Rank 4): Pembrolizumab and EDP1503 in Advanced Melanoma, https://clinicaltrials.gov/ct2/show/NCT03595683?spons=evelo&rank=4, 2018, accessed Feb. 4, 2019.
Evelo Biosciences, Inc. Portfolio: https://evelobio.com/portfolio/, accessed Feb. 4, 2019.
Evelo Biosciences, Inc. website: https://evelobio.com/science/, accessed Feb. 4, 2019.

(56) References Cited

OTHER PUBLICATIONS

Extended European search report and opinion dated Aug. 23, 2016 for EP Application No. 16166001.4.
Fabro, A. et al., The Th17 pathway in the peripheral lung microenvironment interacts with expression of collagen V in the late state of experimental pulmonary fibrosis. (2015) Immunobiology. 220(1):124-35. Epub Aug. 18, 2014.
Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.
Fahy, J.V. Eosinophilic and neutrophilic inflammation in asthma: insights from clinical studies. Proc Am Thorac Soc. May 1, 2009;6(3):256-9. doi: 10.1513/pats.200808-087RM.
Faith et al. Identifying gut microbe-host phenotype relationships using combinatorial communities in gnotobiotic mice. Sci Transl Med 6(220):220ra11 (2014).
Faith et al. The long-term stability of the human gut microbiota. 2013. Science, 341(6141): 1237439.
Falony, et al., Coculture Fermentations of *Bifidobacterium* species and bacteroides thetaiotaomicron Reveal a mechanistic insight into the prebiotic effect of inulin-type Fructans. Applied and environmental microbiology, Apr. 2009;75(8):2312-2319. Epub Feb. 27, 2009.
Falony et al. In vitro kinetics of prebiotic inulin-type fructan fermentation by butyrate-producing colon bacteria: Implementation of online gas chromatography for quantitative analysis of carbon dioxide and hydrogen gas production. Applied and Environmental Microbiology. 2009, vol. 75, No. 18, pp. 5884-5892. Epub Jul. 24, 2009.
Fanning, S., Hall, L.J., Cronin, M., Zomer, A., MacSharry, J., Goulding, D., et al. (2012). Bifidobacterial surface-exopolysaccharide facilitates commensal-host interaction through immune modulation and pathogen protection. Proc Natl Acad Sci U S A 109(6), 2108-2113. doi: 10.1073/pnas.1115621109. Epub Jan. 23, 2012.
Farmer, et al., Gut pain & visceral hypersensitivity. British journal of pain, 2013;7(1):39-47.
Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.
FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.
Federico E. Rey et al., "Dissecting the in Vivo Metabolic Potential of Two Human Gut Acetogens", The Journal of Biological Chemistry, vol. 285, No. 29, pp. 22082-22090, Jul. 16, 2010.
Fenner, et al., *Bacteroides massiliensis* sp. nov., isolated from blood culture of a newborn. International Journal of systematic and evolutionary microbiology, 2005. 55: 1335-1337.
Ferrario, C., Milani, C., Mancabelli, L., Lugli, G.A., Duranti, S., Mangifesta, M., et al. (2016). Modulation of the eps-ome transcription of bifidobacteria through simulation of human intestinal environment. FEMS Microbiol Ecol 92(4), fiw056. doi: 10.1093/femsec/fiw056. Epub Mar. 8, 2016.
Fischer A. et al., "Recovery of learning and memory is associated with chromatin remodelling", Nature. May 10, 2007;447(7141):178-82. Epub Apr. 29, 2007.
Flores-Langarica et al. (2012) "Systemic flagellin immunization stimulates mucosal CD103+ dendritic cells and drives Foxp3+ regulatory T Cell and IgA responses in the mesenteric lymph node," Journal of Immunology. 189 (12):5745-5754. Epub Nov. 14, 2012.
Foguem & Manckoundia, "Lewy Body Disease: Clinical and Pathological "Overlap Syndrome" Between Synucleinopathies (Parkinson Disease) and Tauopathies (Alzheimer Disease)", 2018, Current Neurology and Neuroscience Reports, 18:24. Apr. 8, 2018.
Fraley et al. (1986) "Genetic Transformation in Higher Plants," Critical Reviews Plant Science. 4:1-46.
Frame et al., Production of fertile transgenic maize plants by silicon carbide whisker-mediated transformation, The Plant Journal. 1994; 6:941-948. Dec. 1994.
Frank, D. et al., Molecular-phylogenetic characterization of microbial community imbalances in human inflammatory bowel diseases. 2007. PNAS. 104(34):13780-5. online Aug. 15, 2007.
Frick, et al., Identification of commensal bacterial strains that modulate Yersinia enterocolitica and Dextran sodium sulfate-induced inflammatory responses: implications for the development of probiotics. Infection and immunity, Jul. 2007;75(7):3490-3497. Epub May 7, 2007.
Gaboriau-Routhiau et al. 'The key role of segmented filamentous bacteria in the coordinated maturation of gut helper T cell responses.' Immunity. 2009, vol. 31, No. 4, pp. 677-689.
Gait, M.J., (1984) Oligonucleotide Synthesis: A Practical Approach. Irl Press, pp. vii-xiii.
Galpern & Lang, "Interface between tauopathies and synucleinopathies: A tale of two proteins" 2006, Neurological Progress 59, 3, 449-458. Mar. 2006.
GB Exam and search report dated Aug. 30, 2016 for GB Application No. 1520638.6.
GB Search and Exam report dated Mar. 31, 2016 for GB application 1510469.8.
GB Search and Exam report dated Mar. 31, 2016 for GB application 1510470.6.
GB Search and Exam report dated Apr. 15, 2016 for GB application 1510467.2.
GB Search and Exam report dated Apr. 20, 2016 for GB application 1510466.4.
GB Search and Exam report dated Apr. 20, 2016 for GB application 1510468.0.
GB Search and Exam report dated Aug. 30, 2016 for GB application No. 1520631.1.
GB Search and Exam report dated Nov. 17, 2016 for GB application 1520502.4.
GB Search and Exam report dated Sep. 13, 2016 for GB application 1520497.7.
GB1612190.7 International Search Report dated Apr. 12, 2017.
GB1809729.5 Examination Report dated Oct. 15, 2018.
GenBank Accession No. ABI48297.1 (Jul. 20, 2007) "Fia1 flagellin [Roseburia hominis]".
GenBank Accession No. ABY J02000000 (Nov. 8, 2013) Version 2. "Roseburia intestinal is L 1-82, whole genome shotgun sequencing project".
GenBank Accession No.'s ABY J02000001—ABY J02000409 search results page (Last Updated Apr. 24, 2015).
GenBank accession No. AJ312385 (Oct. 9, 2002) "Roseburia intestinalis 16S rRNA gene, strain L1-82".
GenBank Accession No. CP003040 (Aug. 5, 2011) Version 1. "Roseburia Hominis A2-183, complete genome".
GenBank Accession No. DQ789141. (Jul. 20, 2007) "Roseburia hominis Fla2 flagellin gene".
GenBank Accession No. M20983. (Apr. 26, 1993) "R.cecicola flagellin gene".
GenBank Accession No. NR_044054.1 (Feb. 3, 2015) Blautia wexlerae strain SSM 19850 16S ribosomal RNA gene, partial sequence.
GenBank Accession No. NR_117867.1 (Feb. 3, 2015) Blautia stercoris strain GAM6-1 16S ribosomal RNA gene, partial sequence.
Genbank NCBI Reference Sequence: NR-044054.1, Blautia wexlerae strain DSM 19850 16S ribosomal RNA gene, partial sequence, accessed Feb. 5, 2019.
Genbank NCBI Reference Sequence: NR_117867.1, Blautia stercoris strain GAMC6-1 16S ribosomal RNA gene, partial sequence, accessed Feb. 5, 2019.
Genbank NCBI Reference Sequence: NR_026314, Blautia hydrogenotrophica strain S5a36 16S ribosomal RNA gene, partial sequence, accessed Feb. 5, 2019.
Gennaro, A.R. "Quality Assurance and Control," from Remington: The Science and Practice of Pharmacy, 2000, Lippincott Williams & Wilkins, 20th ed., pp. 980-983.
Geraedts et al. 'Release of satiety hormones in response to specific dietary proteins is different between human and murine small

(56) References Cited

OTHER PUBLICATIONS intestinal mucosa.' Annals of Nutrition and Metabolism. 2010, vol. 56, No. 4, pp. 308-313. Epub Jun. 8, 2010.
Geuking et al. 'Intestinal bacterial colonization induces mutualistic regulatory T cell responses.' Immunity. 2011, vol. 34, No. 5, pp. 794-806. Epub May 19, 2011.
Gewirtz et al. (2001) Cutting edge: bacterial flagellin activates basolaterally expressed TLR5 to induce epithelial proinflammatory gene expression. The Journal of Immunology. 167:(4)1882-1885.
Ghadimi, D. et al., Epigenetic imprinting by commensal probiotics inhibits the IL-23/IL-17 axis in an in vitro model of the intestinal mucosal immune system. JLB. 2012;92(4):895-911. Epub Jun. 22, 2012.
Giraud et al. 'Dissecting the genetic components of adaptation of *Escherichia coli* to the mouse gut.' PLoS Genetics.2008, vol. 4, No. 1, pp. e2. Epub Nov. 27, 2007.
Goldin, B.R. et al., Clinical indications for probiotics: an overview. Clin Infect Dis. Feb. 1, 2008;46 Suppl 2:S96-100; discussion S144-51. doi: 10.1086/523333.
Gonzalez-Rodriguez, I., Sanchez, B., Ruiz, L., Turroni, F., Ventura, M., Ruas-Madiedo, P., et al. (2012). Role of extracellular transaldolase from Bifidobacterium bifidum in mucin adhesion and aggregation. Appl Environ Microbiol 78(11), 3992-3998. doi: 10.1128/AEM.08024-11. Epub Mar. 23, 2012.
Gopal, P.K., Sullivan, P.A., Smart, J.B. Utilization of galacto-oligosaccharides as selective substrates for growth by lactic acid bacteria including Bifidobacterium lactis DR10 and Lactobacillus rhamnosus DR20 (200 1 ). International Dairy Journal, 11 (1-2), pp. 19-25. Dec. 31, 2000.
Gousia, P., et al., Antimicrobial resistance of major foodborne pathogens from major meat products (20II). Foodborne Pathogens and Disease, 8 (1), pp. 27-38. Epub Nov. 1, 2010.
Gray SG. and Dangond F. "Rationale for the use of histone deacetylase inhibitors as a dual therapeutic modality in multiple sclerosis.", Epigenetics. Apr.-Jun. 2006;1(2):67-75. Epub Mar. 5, 2006.
Greenspan et al., Defining epitopes: It's not as easy as it seems. Nature Biotechnology 7: 936-937, 1999. Published: Oct. 1, 1999.
Groeger, D., O'Mahony, L., Murphy, E.F., Bourke, J.F., Dinan, T.G., Kiely, B., et al. (2013). Bifidobacterium infantis 35624 modulates host inflammatory processes beyond the gut. Gut Microbes 4(4), 325-339. doi: 10.4161/gmic.25487. Epub Jun. 21, 2013.
GT Biologies obtains FDA orphan drug designation for paediatric crohn's drug, pharmaceutical-technology.com news, Oct. 8, 2013. Available at: http://www.pharmaceutical-technology.com/news/newsgt-biologics-obtains-fda-orphan-drug-designation-for-paediatric-crohns-drug?WT.mc_id=DN_News.
Haabeth et al. A model for cancer-suppressive inflammation. (2012) OncoImmunology 1(1):1146-1152.
Hai-long Zhang et al., "Study on the Correlation of the Imbalance of TH17 Cells, Th1 Cell, Regulatory T Cells with ankylosing spondylitis Disease Activity Score", Medical Recapitulate, Dec. 2014, vol. 20, No. 24, pp. 4545-4555.
Hammerich, L. et al., Interleukins in chronic liver disease: lessons learned from experimental mouse models. (2014) Clin Exp Gastroenterol. 7:297-306. Sep. 1, 2014.
Hansen, et al., The role of mucosal immunity and host genetics in defining intestinal commensal bacteria. 2010. Curr. Opin. Gastroenterol., 26(6): 564-571.
Hapfelmeier et al. 'Reversible microbial colonization of germ-free mice reveals the dynamics of IgA immune responses.' Science. 2010, vol. 328, No. 5986, pp. 1705-1709.
Hasegawa, Satoru et al. "Intestinal Dysbiosis and Lowered Serum Lipopolysaccharide-Binding Protein in Parkinson's Disease." PloS one vol. 10,11 e0142164. Nov. 5, 2015, doi: 10.1371/journal.pone.0142164.
Hayashi et al. The innate immune response to bacterial flagellin is mediated by Toll-like receptor 5. Nature. 2001, vol. 410, No. 6832, pp. 1099-1103.
Heberle, H., Meirelles, G.V., da Silva, F.R., Telles, G.P., and Minghim, R. (2015). InteractiVenn: a web-based tool for the analysis of sets through Venn diagrams. BMC Bioinformatics 16(1), 169. doi: 10.1186/s12859-015-0611-3.
Hedayat et al. (Mar. 1, 2012) "Prophylactic and therapeutic implications of toll-like receptor ligands," Medicinal Research Reviews. 32(2):294-325. Epub Oct. 25, 2010.
Heuvelin, E., Lebreton, C., Grangette, C., Pot, B., Cerf-Bensussan, N., and Heyman, M. (2009). Mechanisms Involved in Alleviation of Intestinal Inflammation by Bifidobacterium Breve Soluble Factors. PLOS ONE 4(4), e5184. doi: 10.1371/journal.pone.0005184. Epub Apr. 17, 2009.
Hidalgo-Cantabrana, C., Lopez, P., Gueimonde, M., de Los Reyes-Gavilan, C.G., Suarez, A., Margolles, A., et al. (2012). Immune Modulation Capability of Exopolysaccharides Synthesised by Lactic Acid Bacteria and Bifidobacteria. Probiotics Antimicrob Proteins 4(4), 227-237. doi: 10.1007/s12602-012-9110-2.
Hidalgo-Cantabrana, C., Sanchez, B., Alvarez-Martin, P., Lopez, P., Martinez-Alvarez, N., Delley, M., et al. (2015). A single mutation in the gene responsible for the mucoid phenotype of *Bifidobacterium animalis* subsp. *lactis* confers surface and functional characteristics. Appl Environ Microbiol 81(23), 7960-7968. doi: 10.1128/AEM.02095-15. online Oct. 30, 2015.
Hidalgo-Cantabrana, C., Sanchez, B., Milani, C., Ventura, M., Margolles, A., and Ruas-Madiedo, P. (2014). Genomic overview and biological functions of exopolysaccharide biosynthesis in *Bifidobacterium* spp. Appl Environ Microbiol 80(1), 9-18. doi: 10.1128/AEM.02977-13. Epub Oct. 11, 2013.
Higgins, et al. CLUSTAL: A Package for Performing Multiple Sequence Alignment on a Microcomputer. Gene. 73 (1988): 237-244.
Hinchliffe (1993) "Yeast as a vehicle for the expression of heterologous genes," Yeasts. 2nd edition. Rose, A. R.; Harrison, J. H.: Eds. Academic Press Ltd. 5(9). pp. 325-356.
Hinnen et al., Transformation of yeast, Proc. Natl. Acad. Sci. USA. Apr. 1978; 75:1929-1933.
Hoarau, Cyrille et al., Supernatant from Bifidobacterium Differentially Modulates Transduction Signaling Pathways for Biological Functions of Human Dendritic Cells, PLOS ONE, Public Library of Science, US, vol. 3, No. 7, Jul. 1, 2008 (Jul. 1, 2008), pp. e2753-1, XP009139666,ISSN: 1932-6203 *cf. abstract and conclusion, furthermore discussion part at p. 3, col. at the right side*.
Hoarau et al: "TLR2 Activation by Supernatant From Bifidobacterium Breve Modulates Maturation and Survival of Human DCs via Differential Effects on PI3Kinase, p38 and ERK Pathways",Journal of Allergy and Clinical Immuno, Elsevier, Amsterdam, NL, vol. 119, No. 1, Jan. 1, 2007 (Jan. 1, 2007), p. S258, XP005756921, ISSN: 0091-6749, DOI: 10.1016/J.JACI.2006.12.377 *cf. abs.No. 1008 at p. S258*.
Hoekema (1985) The Binary Plant Vector System Offset-drukkerij Kanters BB, Alblasserdam. Chapter V. pp. 63-71.
Hold et al. 'Oligonucleotide probes that detect quantitatively significant groups of butyrate-producing bacteria in human feces.' Applied and environmental microbiology. 2003, vol. 69, No. 7, pp. 4320-4324.
Holdeman, et al., *Eubacterium contortum* (*Prevot*) comb, nov.: Emendation of description and designation of the type strain. International journal of systematic bacteriology. Oct. 1971;21(4): 304-306.
Holland et al. (1990) "Secretion of Heterologous Proteins in *Escherichia coli*," Methods Enzymology. 182:132-143.
Hollenberg et al. (1997) "Production of recombinant proteins by methulotrophic yeasts," Current Opinion Biotechnology. 8(5):554-560.
Hooper at al. 'Molecular analysis of commensal host-microbial relationships in the intestine.' Science. 2001; vol. 291, No. 5505, pp. 881-884.
Horn, et al., Synthesis of Oligonucleotides on Cellulose. Part II: Design and Synthetic Strategy to the Synthesis of 22 Oligodeoxynucleotides Coding for Gastric Inhibitory Polypeptide (GIP). 1980. Nuc Acids Res Symp Ser 225-232.

(56) References Cited

OTHER PUBLICATIONS

Horwell, et al., The 'peptoid' approach to the design of non-peptide, small molecule agonists and antagonists of neuropeptides. 1995. Trends Biotechnol. 13(4):132-134.
Hossain et al. "Flagellin, a TLR5 agonist, reduces graft-versus-host disease in allogeneic hematopoietic stem cell transplantation recipients while enhancing antiviral immunity," Journal of Immunology. Nov. 2011; 187(10): p. 5130-5140. Nov. 15, 2011.
Hougee, et al., Oral treatment with probiotics reduces allergic symptoms in ovalbumin-sensitized mice:a bacterial strain comparative study. Int Arch Allergy Immunol. 2010; 151:107-117. Epub Sep. 15, 2009.
Hoyles L. et al. Gastrointestinal Tract, Chapter 56. Handbook of Hydrocarbon and Lipid Microbiology Springer Verlag Berlin 2010, 3120-32.
Hsiao, Elaine Y et al. "Microbiota modulate behavioral and physiological abnormalities associated with neurodevelopmental disorders." Cell vol. 155,7 (2013): 1451-63. doi: 10.1016/j.cell.2013.11.024. Epub Dec. 5, 2013.
Hughes, K.R., Harnisch, L.C., Alcon-Giner, C., Mitra, S., Wright, C.J., Ketskemety, J., et al. (2017). Bifidobacterium breve reduces apoptotic epithelial cell shedding in an exopolysaccharide and MyD88-dependent manner. Open Biol 7(1). doi: 10.1098/rsob.160155.
Humira 20 mg/ 0.2 ml Solution for Injection in Pre-Filled Syringe—Summary of Product Characteristics, https://www.medicines.org.uk/emc/product/9080/smpc/print, accessed on Oct. 25, 2019, 30 pages.
Huycke, M M et al. "Multiple-drug resistant enterococci: the nature of the problem and an agenda for the future." Emerging infectious diseases vol. 4,2 (1998): 239-49. doi: 10.3201/eid0402.980211. Apr.-Jun. 1998.
Hyland and Cox, "The regulation of veratridine-stimulated electrogenic ion transport in mouse colon by neuropeptide Y (NPY), Y1 and Y2 receptors", 2005, British Journal of Pharmacology,146(5), 712-722. Nov. 2005.
Hytönen, J., Haataja, S., and Finne, J. (2003). *Streptococcus pyogenes* Glycoprotein-Binding Strepadhesin Activity Is Mediated by a Surface-Associated Carbohydrate-Degrading Enzyme, Pullulanase. Infection and Immunity 71(2), 784-793.
Hytonen, J., Haataja, S., and Finne, J. (2006). Use of flow cytometry for the adhesion analysis of *Streptococcus pyogenes* mutant strains to epithelial cells: investigation of the possible role of surface pullulanase and cysteine protease, and the transcriptional regulator Rgg. BMC Microbiol 6, 18. doi: 10.1186/1471-2180-6-18. Published online Feb. 24, 2006.
Ibrahim et al., "Method for the isolation of highly purified *Salmonella flagellins*," Journal of Clinical Microbiology. Dec. 1985; 22(6):1040-1044.
Inaba et al., "Generation of large numbers of dendritic cells from mouse bone marrow cultures supplemented with granulocyte/macrophage colony-stimulating factor," J. Exp. Med. Dec. 1992; 176(6):1693-1702.
International Search Report for International Application No. PCT/GB2012/052495, dated Mar. 25, 2013.
International Preliminary Report dated Mar. 1, 2017 for International Application No. PCT/GB2015/054113.
International Preliminary Report on Patentability corresponding to International Patent Application No. PCT/GB2014/051123, dated Oct. 13, 2015.
International Preliminary Report on Patentability dated Sep. 17, 2019 for International Application Serial No. PCT/EP2018/065809, (13 pages).
International Preliminary Report on Patentability for International Application No. PCT/GB2012/051686 dated Jan. 14, 2014.
International Search Report dated Jan. 27, 2017 for International Application No. PCT/GB2016/053622.
International Search Report dated Feb. 10, 2016 for International Application No. PCT/GB2015/054113.
International Search Report dated Feb. 17, 2017 for International Application No. PCT/GB2016/053676.
International Search Report dated Mar. 7, 2016 for International Application No. PCT/GB2015/054112.
International Search report dated Mar. 15, 2003 for International Application No. PCT/GB2002/05255.
International Search Report dated Aug. 21, 2014 for International Application No. PCT/GB2014/051123.
International Search Report dated Aug. 26, 2016 for International application No. PCT/GB2016/051774.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International Search Report dated Aug. 24, 2018 for International Application Serial No. PCT/EP2018/065809, (6 pages).
International Search Report for International Application No. PCT/GB2012/051686 dated Jan. 31, 2013.
International search report with written opinion dated Feb. 26, 2018 for PCT/GB2017/053722.
International search report with written opinion dated Jun. 8, 2017 for GB Application No. 1616016.
International search report with written opinion dated Sep. 29, 2017 for GB Application No. 1621123.
International search report with written opinion dated Oct. 16, 2017 for PCT/GB2017/052076.
Inturri, R., Molinaro, A., Di Lorenzo, F., Blandino, G., Tomasello, B., Hidalgo-Cantabrana, C., et al. (2017). Chemical and biological properties of the novel exopolysaccharide produced by a probiotic strain of Bifidobacterium longum. Carbohydr Polym 174, 1172-1180. doi: 10.1016/j.carbpol.2017.07.039. Epub Jul. 19, 2017.
Ishikawa, et al., Effect of bifidobacteria to suppress Th17, Food Science and technology institute, 2008, 5 Pages.
Ispirli, H. et al., Characterization of functional properties of Enterococcus faecium strains isolated from human gut. Can. J. Microbiol. 61: 861-870 (2015) dx.doi.org/10.1139/cjm-2015-0446.
Israel, E. et al., Supplementary Appendix, Severe and difficult-to-treat asthma in adults. N. Engl J Med 2017;p. 377:965-76. DOI: 10.1056/NEJMra1608969.
Israel, et al., Severe and difficult-to-treat asthma in adults, The New England Journal of Medicine, Sep. 2017; 377(10):965-976.
Issue Notification dated Feb. 20, 2019 for Co-Pending U.S. Appl. No. 15/631,945.
Ito et al. (1983) "Transformation of Intact Yeast Cells Treated with Alkali Cations," J. Bacteriology. 153:163-168.
Ivanov, D., Emonet, C., Foata, F., Affolter, M., Delley, M., Fisseha, M., et al. (2006). A serpin from the gut bacterium Bifidobacterium longum inhibits eukaryotic elastase-like serine proteases. J Biol Chem 281 (25), 17246-17252. doi: 10.1074/jbc.M601678200. Epub Apr. 20, 2006.
Ivanov et al. 'Induction of intestinal Th17 cells by segmented filamentous bacteria.' Cell. 2009, vol. 139, No. 3, pp. 485-498. available in PMC Apr. 30, 2010.
Jackson MS, Bird AR, McOrist AL. Comparison of two selective media for the detection and enumeration of Lactobacilli in human faeces (2002). J Microbial Methods. 51 (3), pp. 313-321.
Jacobs, S. A., Huang, F., Tsien, J. Z. and Wei, W. (2016). Social Recognition Memory Test in Rodents. Bio-protocol 6(9): e1804. DOI:10.21769/BioProtoc.1804. May 5, 2016.
Jagveer Singh et al., "Bifidobacterium longum, a lactic acid-producing intestinal bacterium inhibits colon cancer and modulates the intermediate biomarkers of colon carcinogenesis", Carcinogenesis vol. 18 No. 4 pp. 833-841, 1997. Apr. 1997.
Jarchum et al., "Toll-Like Receptor 5 Stimulation Protects Mice from Acute Clostridium difficile Colitis," Infection and Immunity. Apr. 2011; 79(4):1498-1503.

(56) References Cited

OTHER PUBLICATIONS

Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jenq, Robert R., Intestinal Bluatia is associated with reduced death from graft versus-host disease, Bio Blood Marro Transplant. Aug. 2015; 21(8): 1373-1383. doi:10.1016/j.bbmt.2015.04.016.
Jeon, S.G., Kayama, H., Ueda, Y., Takahashi, T., Asahara, T., Tsuji, H., et al. (2012). Probiotic Bifidobacterium breve induces IL-10-producing Tr1 cells in the colon. PLoS Pathog 8(5), e1002714. doi: 10.1371/journal.ppat.1002714. Epub May 31, 2012.
Jiao et al., Blockade of Notch Signaling Ameliorates Murine Collagen-Induced Arthritis via Suppressing Th1 and Th17 Cell Responses. 2014; Pathology, 184(4):1085-1093. Epub Feb. 1, 2014.
Joblin K N., "Ruminal Acetogens and Their Potential to Lower Remnant Methane Emissions." Australian Journal of Agricultural Research. vol. 50. No. 8. 1999, pp. 1307-1313. XP001010439.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. Gastroenterology, 2005;128: p. A281, XP009193489.
Kang and Kim, 2015, "Suppression of NMDA receptor function in mice prenatally exposed to valproic acid improves social deficits and repetitive behaviors", Frontiers in Molecular Neuroscience, 2015, 8:(17), 1-9. May 27, 2015.
Kang, S. et al. (2010) "Dysbiosis of fecal microbiota in Crohn's disease patients as revealed by a custom phylogenetic microarray," Inflammatory Bowel Diseases. Dec. 2010;16(12):2034-2042. doi: 10.1002/ibd.21319.
Kantak PA et al., "Obsessive-compulsive-like behaviors in house mice are attenuated by a probiotic (Lactobacillus rhamnosus GG)", Behav Pharmacol. Feb. 2014;25(1):71-9. doi: 10.1097/FBP.0000000000000013.
Karaffova, et al., Interaction of TGF-B4 and IL-17 with IgA secretion in the intestine of chickens fed with E. faecium AL41 and challenged with S. Enteritidis. Research in Veterinary science. 2015:75-79. Epub Apr. 17, 2015.
Kari Shoaf et al., "Prebiotic Galactooligosaccharides Reduce Adherence of Enteropathogenic *Escherichia coli* to Tissue Culture Cells", Infection and Immunity, Dec. 2006, vol. 74. No. 12, p. 6920-6928. Published online Sep. 18, 2006.
Karin, M. Nuclear factor-kappaB in cancer development and progression. Nature. May 25, 2006;441(7092):431-6.
Keller et al.. "DNA Probes", 1994. Stockton Press. New York. XP002158943 108660 pp. 594-596.
Kelly et al. 'Commensal anaerobic gut bacteria attenuate inflammation by regulating nuclear-cytoplasmic shuttling of PPAR-y and ReiA.' Nature Immunology. 2003, vol. 5, No. 1, pp. 104-112. Epub Dec. 21, 2003.
Kelly, et al., Commensal gut bacteria: mechanisms of immune modulation. TRENDS in immunology, 2005;26(6):326-333.
Kingsley M. A Personalized Approach to Managing 18D. Gastroenterology and Hepatology 12(5)308-315, May 2016.
Kinnebrew et al., Interleukin 23 production by intestinal CD1 03(+)CD11 b(+) dendritic cells in response to Interleukin 23 production by intestinal CD1 03(+ )CD11 b(+) dendritic cells in response to bacterial flagellin enhances mucosal innate immune defense, Immunity. 2012; 36(2): 276-287. Epub Feb. 2, 2012.
Kinoshita, H., Uchida, H., Kawai, Y., Kawasaki, T., Wakahara, N., Matsuo, H., et al. (2008). Cell surface Lactobacillus plantarum LA 318 glyceraldehyde-3-phosphate dehydrogenase (GAPDH) adheres to human colonic mucin. J Appl Microbiol 104(6), 1667-1674. doi: 10.1111/j.1365-2672.2007.03679.x. Epub Jan. 9, 2008.
Kirsty Minton: Mucosal immunology: The ins and outs of gut inflammation, The journal of immunology, 4(2), Feb. 1, 2004: pp. 81-81, XP055252701.
Kishimoto, M., Nomoto, R., Mizuno, M., and Osawa, R. (2017). An in vitro investigation of immunomodulatory properties of Lactobacillus plantarum and L. delbrueckii cells and their extracellular polysaccharides. Bioscience of Microbiota, Food and Health 36(3), 101-110. doi: 10.12938/bmfh.17-001. Epub Mar. 22, 2017.
Kitahara, M. et al., *Bacteroides plebeius* sp. nov. and *Bacteroides coprocola* sp. nov., isolated from human faeces, 2005; Int J Syst Ev Microbiol 55: 2143-47. DOI 10.1099/ijs.063788.0. First Published: Sep. 1, 2005.
Koenders, M.I. et al., Interleukin-17 Acts Independently of TNF-a under Arthritic Conditions. (2006) J. Immunol. 176:6262-6269.
Kogyo, S. Lactic Acid Bacteria, Intestinal Flora ad Health II; Physiological effects of heat-treated lactococcus "EF-2001" and application to food. Mar. 30, 2001, vol. 44, No. 6, pp. 35-39.
Koh, Gar Yee et al., Parabacteroides distasonis attenuate toll-like receptor 4 signaling and Akt activation and blocks colon tumor formulation in high-fat-diet-fed azoxymethane-treated mice, International Journal of Cancer, 2018, 143, 1797-1805. pp. 1-30. Accepted Article, doi: 10.1002/ijc.31559. Apr. 26, 2018.
Kondziella, W, "A New Method for the Measurement of Muscle Relaxation in White Mice" Arch Int Pharmacodyn Ther. Dec. 1, 1964;152:277-84.
Korhonen, J.M., Sclivagnotis, Y., Von Wright, A Characterization of dominant cultivable lactobacilli and their antibiotic resistance profiles from faecal samples of weaning piglets (2007). Journal of Applied Microbiology, 103 (6), pp. 2496-2503.
Kumolosasi, E., Salim, E., Jantan, I., and Ahmad, W. (2014). Kinetics of Intracellular, Extracellular and Production of Pro-Inflammatory Cytokines in Lipopolysaccharide-Stimulated Human Peripheral Blood Mononuclear Cells. Tropical Journal of Pharmaceutical Research 13(4), 536-543. doi: 10.4314/tjpr.v13i4.8.
Kverka, M. et al., Oral administration of Parabacteroides distasonis antigens attenuates experimental murine colitis through modulation of immunity and microbiota composition. Clinical & Experimental Immunology. 2010; 163:250-259. Epub Nov. 19, 2010.
Laetitia Rodes et al., "Microencapsulated *Bifidobacterium longum* subsp. *infantis* ATCC 15697 Favorably Modulates Gut Microbiota and Reduces Circulating Endotoxins in F344 Rats", BioMed Research International, vol. 2014, Article ID 602832, 11 pages. Published May 22, 2014.
Lahteinen, T., et al., A Pro biotic properties of Lactobacillus isolates originating from porcine intestine and feces (20 10) Anaerobe, 16 (3), pp. 293-300. Epub Aug. 18, 2009.
Lakhdari, et al. Identification of NF-KB Modulation Capabilities within Human Intestinal Commensal Bacteria. J Biomed Biotechnol. 2011; 2011: 282356. Published Jun. 14, 2011.
Lapadula, G. et al., "Adalimumab in the Treatment of Immune-Mediated Diseases", International Journal of Immunopathology and Pharmacology, 2014, vol. 27, No. 1(s), 33-48. Jan.-Mar. 2014.
Laukova, A. et al. Benefits of Combinative Application of Probiotic, Enterocin M-Producing Strain Enterococcus Faecium AL41 and Eleutherococcus Senticosus in Rabbits. Folia Microbiol (Praha) 61 (2), 169-177. Sep. 9, 2015.
Laureen Crouzet et al., "The altered gut microbiota of IBS patients plays a key role in visceral hypersensitivity: specific role of sulphate-reducing bacteria", INRA Symposium, 2012.
Lavallie et al. (1995) "Gene fusion expression systems in *Escherichia coli*," Current Opinion Biotechnology. 6 (5):501-506.
Law, J., Buist, G., Haandrikman, A., Kok, J., Venema, G., and Leenhouts, K. (1995). A system to generate chromosomal mutations in Lactococcus lactis which allows fast analysis of targeted genes. Journal of Bacteriology 177(24), 7011-7018.
Lebeer, S., Claes, I.J., Verhoeven, T.L., Vanderleyden, J., and De Keersmaecker, S.C. (2011). Exopolysaccharides of Lactobacillus rhamnosus GG form a protective shield against innate immune factors in the intestine. Microb Biotechnol 4(3), 368-374. doi: 10.1111/j.1751-7915.2010.00199.x. Epub Aug. 17, 2010.
Lebeer, S., Verhoeven, T.L., Francius, G., Schoofs, G., Lambrichts, I., Dufrene, Y., et al. (2009). Identification of a Gene Cluster for the Biosynthesis of a Long, Galactose-Rich Exopolysaccharide in

(56) References Cited

OTHER PUBLICATIONS

Lactobacillus rhamnosus GG and Functional Analysis of the Priming Glycosyltransferase. Appl Environ Microbiol 75(11), 3554-3563. doi: 10.1128/AEM.02919-08. Published online Apr. 3, 2009.

Lee Do Yeon et al., "Kynurenic acid attenuates MPP-induced dopaminergic neuronal cell death via a Bax-mediated mitochondrial pathway",2008, European Journal of Cell Biology 87:389-397. Epub May 6, 2008.

Lee, et al. Intestinal microbiota in pathophysiology and management of irritable bowel syndrome . 2014. World J Gastroenterol. 20(27): 8886-8897.

Lejeune et al. Efficiency of Recombinant Human TNF in Human Cancer Therapy. Cancer Immun. 6:6 (2006).

Leser et al. 'Culture-independent analysis of gut bacteria: the pig gastrointestinal tract microbiota revisited'. Applied and Environmental Microbiology. 2002, vol. 68, No. 2, pp. 673-690.

Leslie, et al., Trehalose and sucrose protect both membranes and proteins in intact bacteria during drying. (1995) Appl. Environ. Microbiol. 61, 3592-3597.

Letran et al. 'TLR5-deficient mice lack basal inflammatory and metabolic defects but exhibit impaired CD4 T cell responses to a flagellated pathogen.' The Journal of Immunology. 2011, vol. 186, No. 9, pp. 5406-5412. Published online Mar. 30, 2011.

Li, C.Y., Lin Hc Fau—Lai, C.-H., Lai Ch Fau—Lu, J.J.-Y., Lu Jj Fau—Wu, S.-F., Wu Sf Fau—Fang, S.-H., and Fang, S.H. (2011). Immunomodulatory effects of lactobacillus and Bifidobacterium on both murine and human mitogen-activated T cells. Int Arch Allergy Immunol 156(2), 128-136. doi: 10.1159/000322350.

Li, et al,. Screening and Identification of Lactobacillus animalis strain and characteristics of its bacteriostatic protein, Weishengwuxue Tongbao 2009; 36(7): 1001-1007.

Li Q et al., "The microbiota-gut-brain axis and its potential therapeutic role in autism spectrum disorder", Neuroscience. Jun. 2, 2016;324:131-9. doi: 10.1016/j.neuroscience.2016.03.013. Epub Mar. 8, 2016.

Lilley et al., Methods in Enzymology; DNA Structure Part A: Synthesis and Physical Analysis of DNA. 1992; vol. 2011. pp. v-vii.

Liu, Chang-jian et al., Antioxidant and Cholesterol-Reducing Properties of Enterococcus gallinarum m661, Bioengineering (Food Science), vol. 34, No. 7, Dec. 31, 2013, pp. 157-161.

Liu et al. Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb, nov., *Blautia hansenii* comb, nov., *Blautia hydrogenotrophica* comb, nov., *Blautia luti* comb, nov., *Blautia producta* comb, nov., *Blautia schinkii* comb. nov. and description of *Blautia wexlerae* sp. nov., isolated from human faeces. 2008. Int J Syst Evol Microbiol 58,1896-1902.

Liu, Y., et al., Human-derived probiotic Lactobacillus reuteri strains differentially reduce intestinal inflammation (2010). American Journal of Physiology—Gastrointestinal and Liver Physiology, 299 (5), pp. G1087-G1096. Epub Aug. 26, 2010.

Ljungh, A, Wadstrorn, T. Lactic acid bacteria as probiotics (2006). Current Issues in Intestinal Microbiology, 7 (2), pp. 73-90.

Lodemann, U. et al., Effects of the Probiotic enterococcus faecium and pathogenic *Escherichia coli* strains in a pig and human epithelial intestinal cell model. Hindawi publishing corporation scientifica. 2015(235184) 10 pages. Epub Mar. 26, 2015.

Lopetuso et al. Commensal Clostridia: leading players in the maintenance of gut homeostasis. 2013. Gut Pathogens, 5: 23.

Lopez, P., Gonzalez-Rodriguez, I., Sanchez, B., Ruas-Madiedo, P., Suarez, A., Margolles, A., et al. (2012). Interaction of Bifidobacterium bifidum LMG13195 with HT29 cells influences regulatory-T-cell-associated chemokine receptor expression. Appl Environ Microbiol 78(8), 2850-2857. doi: 10.1128/AEM.07581-11. Epub Feb. 17, 2012.

Lopez-Boado, Y. S. et al., Bacterial Exposure Induces and Activates Matrilysin in Mucosal Epithelial Cells. J Cell Biol148, 1305-1315 (2000).

Louis et al. 'Diversity, metabolism and microbial ecology of butyrate-producing bacteria from the human large Intestine.' FEMS Microbiology Letters. 2009, vol. 294, No. 1, pp. 1-8. Epub Feb. 13, 2009.

Louis et al. 'Diversity of human colonic butyrate-producing bacteria revealed by analysis of the butyryl—GoA: acetate GoA—transferase gene.' Environmental Microbiology. 2010, vol. 12, No. 2, pp. 304-314. Epub Oct. 5, 2009.

Louis et al. 'Organization of butyrate synthetic genes in human colonic bacteria: phylogenetic conservation and horizontal gene transfer.' FEMS Microbiology Letters. 2007, vol. 269, No. 2, pp. 240-247. Published: Apr. 1, 2007.

Lozupone. Diversity, stability and resilience of the human gut microbiota. 2012. Nature. Sep. 13, 2012; 489 (7415): 220-230.

López, P., González-Rodríguez, I., Gueimonde, M., Margolles, A., and Suárez, A. (2011). Immune Response to Bifidobacterium bifidum Strains Support Treg/Th17 Plasticity. PLOS ONE 6(9), e24776. doi: 10.1371/journal.pone.0024776. Sep. 22, 2011.

López, P., Gueimonde, M., Margolles, A., and Suárez, A. (2010). Distinct Bifidobacterium strains drive different immune responses in vitro. International Journal of Food Microbiology 138(1), 157-165. doi: https://doi.org/10.1016/j.ijfoodmicro.2009.12.023. Epub Jan. 4, 2010.

Ludolph, A C et al. "Tauopathies with parkinsonism: clinical spectrum, neuropathologic basis, biological markers, and treatment options." European journal of neurology vol. 16,3 (2009): 297-309. doi: 10.1111/j.1468-1331.2008.02513.x.

Luger, D. and Caspi, R.R., New perspectives on effector mechanisms in uveitis. (2008) Semin. Immunopathol. 30(2): 135-143. Published online Mar. 4, 2008.

Álvarez-Martín, P., O'Connell-Motherway, M., van Sinderen, D., and Mayo, B. (2007). Functional analysis of the pBC1 replicon from Bifidobacterium catenulatum L48. Applied Microbiology and Biotechnology 76(6), 1395. doi: 10.1007/s00253-007-1115-5. Aug. 17, 2007.

Lyons, et al., Bacterial strain-specific induction of Foxp3 T regulatory cells is protective in murine allergy models. Clinical & Experimental Allergy. 2010; 40:811-819. Epub Jan. 11, 2010.

Machiels, et al., Predominant dysbiosis in patients with ulcerative colitis is different from Crohn's disease patients, Inflammatory Bowel Diseases, Microbiology 2012. 8th Congress of ECCO. (This Abstract is in 7th Congress 2012).

Machiels, K. A decrease of the butyrate-producing species *Roseburia hominis* and *Faecalibacterium prausnitzii* defines dysbiosis in patients with ulcerative colitis.Gut. Aug. 2014;63(8):1275-83. doi: 10.1136/gutjnl-2013-304833. Epub Sep. 10, 2013.

MacPherson, AJ et al., IgA responses in the intestinal mucosa against pathogenic and non-pathogenic microorganisms. Oct. 2001. 3(12). 1021-1035.

MacPherson, AJ., et al., The functions of mucosal T cells in containing the indigenous commensal flora of the intestine. Cell Mol Life Sci. Dec. 2002;59(12):2088-96.

MacPherson et al. 'IgA adaptation to the presence of commensal bacteria in the intestine.' Gut-Associated Lymphoid Tissues. Springer Berlin Heidelberg, 2006. 117-136.

MacSharry et al., Immunomodulatory effects of feeding with bifidobacterium longum on allergen-induced lung inflammation in the mouse. Pulmonary pharmacology & Therapeutics. 2012; 25:325-334. Epub Jun. 13, 2012.

Mahowald et al. 'Characterizing a model human gut microbiota composed of members of its two dominant bacterial phyla.' Proceedings of the National Academy of Sciences. 2009, vol. 106, No. 14, pp. 5859-5864. Epub Mar. 24, 2009.

Maintaining Cultures for Biotechnology and Industry (1996) Jennie C. Hunter-Cevera, Academic Press.

Mallya et al. 'Characterization of the five novel Ly—6 superfamily members encoded in the MHC, and detection of cells expressing their potential ligands.' Protein Science. 2006, vol. 15, No. 10, pp. 2244-2256. Oct. 2006.

Manni et al., A tale of two cytokines: IL-17 and IL-22 in asthma and infection. Expert Rev Respir Med. Feb. 2014 ; 8(1): 25-42. doi:10.1586/17476348.2014.854167. Published online Dec. 10, 2013.

(56) References Cited

OTHER PUBLICATIONS

Mansour et al. Isolation of Enterococcus faecium NM113, Enterococcus faecium NM213 and Lactobacillus casei NM512 as novel probiotics with immunomodulatory properties. (2014) Microbiol Immunol. 58(10):559-69.
Martin et al., Cloning, Nucleotide Sequence, and Taxonomic Implications of the Flagellin Gene of *Roseburia cecicola*, Journal of Bacteriology. Jun. 1988; 170(6):2612-2617.
Martin R. et al., Isolation of lactobacilli from sow milk and evaluation of their probiotic potential. J of dairy research 76(4)418-425. Nov. 2009. Epub Jul. 29, 2009.
Masco, L., et al., Identification of *Bifidobacterium* Species Using rep-PCR Fingerprinting. Systematic and Applied Microbiology 26(4):557-63 • Nov. 2003.
Matsuda F et al: Evaluation of a probiotics,BBG-01, for enhancement of immunogenicity of an oral inactivated cholera vaccine and safety: A randomized, double-blind, placebo-controlled trial in Bangladeshi children under 5 years of age, Vaccine, Elsevier, Amsterdam, NL, vol. 29, No. 10, Dec. 26, 2010 (Dec. 26, 2010), pp. 1855-1858, XP028147184, ISSN: 0264-410X, DOI: 10.1016/J.VACCINE.2010.12.133 [retrieved on Jan. 7, 2011] *cf. abstract*.
Matthes, et al., Simultaneous rapid chemical synthesis of over one hundred oligonucleotides on a microscale. Apr. 1984. EMBO Journal, 3(4): p. 801-805.
Maya, J.R. et al., Emerging Therapies for Noninfectious Uveitis: What May Be Coming to the Clinics. (2014) J. Ophthalmology. 310329. Epub Apr. 24, 2014.
Mayer, Emeran A. et al., "Gut Microbes and the Brain: Paradigm Shift in Neuroscience", Journal of Neuroscience Nov. 12, 2014, 34 (46) 15490-15496; DOI: https://doi.org/10.1523/JNEUROSCI.3299-14.2014.
Mazmanian et al. 'An immunomodulatory molecule of symbiotic bacteria directs maturation of the host immune system.' Cell. Jul. 15, 2005; vol. 122, No. 1, pp. 107-118.
McCarville, J.L., Dong, J., Caminero, A., Bermudez-Brito, M., Jury, J., Murray, J.A., et al. (2017). A Commensal Bifidobacterium longum Strain Prevents Gluten-Related Immunopathology in Mice through Expression of a Serine Protease Inhibitor. Applied and Environmental Microbiology 83(19), e01323-01317. doi: 10.1128/AEM.01323-17. Print Oct. 1, 2017.
McClymont, S.A., Putnam Al Fau—Lee, M.R., Lee Mr Fau—Esensten, J.H., Esensten Jh Fau—Liu, W., Liu W Fau—Hulme, M.A., Hulme Ma Fau—Hoffmuller, U., et al. (2011). Plasticity of human regulatory T cells in healthy subjects and patients with type 1 diabetes. Journal of Immunology 186(7), 3918-3926. doi: 10.4049/jimmunol.1003099.
McIntosh et al. 'Mechanism of conjugated linoleic acid and vaccenic acid formation in human faecal suspensions and pure cultures of intestinal bacteria.' Microbiology. 2009, vol. 155, No. 1, pp. 285-294.
McLaughlin., "McLaughlin et al. Fatty acid chain length determines cholecystokinin secretion and effect on human gastric motility. Gastroenterology. 1999, vol. 116, No. 1, pp. 46-53".
Menard, S., Laharie D Fau—Asensio, C., Asensio C Fau—Vidal-Martinez, T., Vidal-Martinez T Fau—Candalh, C., Candalh C Fau—Rullier, A., Rullier A Fau—Zerbib, F., et al. (2005). Bifidobacterium breve and *Streptococcus thermophilus* secretion products enhance T helper 1 immune response and intestinal barrier in mice. Experimental Biology and Medicine (Maywood) 230(10), 749-756.
Meyer et al. (1992) "The use of cassava mosaic virus as a vector system for plants," Gene. 110:213-217.
Meyza, et al. The BTBR mouse model of idiopathic autism—Current view on mechanisms. 2017. Neurosci Biobehav Rev.;76(Pt A):99-110. Epub Feb. 3, 2017.
Mikayama, et al., Molecular cloning and functional expression of a cDNA encoding glycosylation-inhibiting factor. Proc.Nati.Acad. Sci. USA, Nov. 1993; vol. 90: 10056-10060.
Milani, C., Mangifesta, M., Mancabelli, L., Lugli, G.A., Mancino, W., Viappiani, A., et al. (2017). The Sortase-Dependent Fimbriome of the Genus *Bifidobacterium*: Extracellular Structures with Potential to Modulate Microbe-Host Dialogue. Appl Environ Microbiol 83(19). doi: 10.1128/AEM.01295-17.
Mincheol Kim et al., "Towards a taxonomic coherence between average nucleotide identity and 16S rRNA gene sequence similarity for species demarcation of prokaryotes", International Journal of Systematic and Evolutionary Microbiology (2014), 64, 346-351. Feb. 1, 2014.
Miossec, P. et al., Targeting IL-17 and TH17 cells in chronic inflammation, Oct. 2012; Nature Rev Drug Discovery 11(10):763-776. doi: 10.1038/nrd3794.
Miraglia Del Giudice, M., Indolfi, C., Capasso, M., Maiello, N., Decimo, F., and Ciprandi, G. (2017). Bifidobacterium mixture (B longum BB536, B infantis M-63, B breve M-16V) treatment in children with seasonal allergic rhinitis and intermittent asthma. Italian Journal of Pediatrics 43(1), 25. doi: 10.1186/s13052-017-0340-5.
Mitropoulou, G. et al. Immobilization Technologies in Probiotic Food Production. (2013) Journal Nutr Metab. (2013) 716861. Published Oct. 28, 2013.
Miyake, T. et al., Phylogenetic analysis of the genus *Bifidobacterium* and related genera based on 16S rDNA sequences. Microbiol. Immunol. 1998; 42(10): 661-667.
Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques, 1st edition. An intensive laboratory course. 1998.
Monteleone et al., IL-10-dependent partial refractoriness to Toll-like receptor stimulation modulates gut mucosal dendritic cell function, European Journal of Immunology. 2008; 38(6):1533-1547.
Monteleone, I. et al., Th17-related cytokines: new players in the control of chronic intestinal inflammation. (2011) BMC Medicine. 2011,9:122. Published: Nov. 15, 2011.
Mortaz, E. et, al., Anti-Inflammatory Effects of Lactobacillus Rahmosus and Bifidobacterium Breve on Cigarette Smoke Activated Human Mcrophiages, PLoS ONE, Apr. 21, 20i15, 10(8):e0136455.DOI:10.1371, Journal.pone.0136455.
Mucientes, A. et al., Specific association of IL17A genetic variants with panuveitis. (2015) Br J Ophthalmol. 99(4):566-70. Epub Jan. 16, 2015.
Mukai et al., SH3BP2 Gain-Of-Function Mutation Exacerbates Inflammation and Bone Loss in a Murine Collagen-Induced Arthritis Model, 2014 PLoS ONE 9(8): e105518. Aug. 21, 2014.
Mulder et al. 'Environmentally-acquired bacteria influence microbial diversity and natural innate immune responses at gut surfaces'. Bmc Biology. 2009, vol. 7, No. 1, pp. 79 . Published: Nov. 20, 2009.
Murofushi, Y., Villena, J., Morie, K., Kanmani, P., Tohno, M., Shimazu, T., et al. (2015). The toll-like receptor family protein RP105/MD1 complex is involved in the immunoregulatory effect of exopolysaccharides from Lactobacillus plantarum N14. Mol Immunol 64(1), 63-75. doi: 10.1016/j.molimm.2014.10.027. Epub Nov. 13, 2014.
Narushima, et al., Characterization of the 17 strains of regulatory T cell-inducing human-derived Clostridia. Gut Microbes Mar. 18, 2014; 5:3, 333-339.
Naughton PJ; Grant G. (2005) Modelling of salmonellosis In: Microbial Ecology of the Growing Animal Holzapfel WH, Naughton PJ. (Eds). London, Elsevier, pp. 235-257.
NCBI Reference Sequence: NR_026314.1, Blautia hydrogenotrophica strain S5a36 16S ribosomal RNA gene, partial sequence (Feb. 3, 2015), 3 pages.
NCBI Reference Sequence: NR_041278.1, Bacteroids coprocola strain M16165 ribosomal RNA gene, partial sequence. Aug. 8, 2011 National Center for Biotechnology Information, NIH.
Neeser, J.R., et al., Lactobacillus johnsonii Lal shares carbohydrate-binding specificities with several enteropathogenic bacteria (2000). Glycobiology, 10 (11), pp. II93-II99.
Neish, A. S. et al., Prokaryotic Regulation of Epithelial Responses by Inhibition of IKB-α Ubiquitination. Science 289, 1560 (2000).

(56) References Cited

OTHER PUBLICATIONS

Neish et al., TLRS in the Gut. II. Flagellin-induced inflammation and antiapoptosis, American Journal of Physiology-Gastrointestinal and Liver Physiology. 2007;292:G462-466.
Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274. Epub Oct. 12, 2006.
Neville, B.A., Functional genomics of motile commensal intestinal bacteria. PhD Thesis. University College Cork. 2013. 281 Pages.
Neville, et al., Characterization of pro-inflammatory flagellin proteins produced by Lactobacillus ruminis and related motile Lactobacilli. PloS one. Jul. 2012;7(7):e40592. Published online Jul. 10, 2012.
Neyrinck et al. 'Dietary modulation of clostridial cluster XIVa gut bacteria (*Roseburia* spp.) by chitin-glucan fiber improves host metabolic alterations induced by high-fat diet in mice.' The Journal of Nutritional Biochemistry. 2012, vol. 23, No. 1, pp. 51-59. Epub Mar. 15, 2011.
Ng et al., Archaeal flagella, bacterial flagella and type IV pili: a comparison of genes and posttranslation modification, Journal of Molecular Microbiology and Biotechnology. 2006;11:167-191.
Nicolau, D.P. Current challenges in the management of the infected patient (2011). Current Opinion in Infectious Diseases, 24 (Suppll), pp. SI-S10.
Non-Final Office Action dated Oct. 8, 2019 for U.S. Appl. No. 16/265,238.
Non-Final Office Action dated Oct. 9, 2019 for U.S. Appl. No. 15/969,543.
Notice of Allowance dated Feb. 3, 2016 for U.S. Appl. No. 14/349,907.
Notice of Allowance dated Mar. 6, 2017 for U.S. Appl. No. 14/249,710.
Notice of Allowance dated Mar. 30, 2011 for U.S. Appl. No. 10/285,224.
Notice of Allowance dated Apr. 25, 2016 for U.S. Appl. No. 14/232,475.
Notice of allowance dated Jun. 16, 2017 for U.S. Appl. No. 14/249,710.
Notice of Allowance dated Aug. 23, 2016 for U.S. Appl. No. 14/232,475.
Notice of allowance dated Sep. 1, 2017 for U.S. Appl. No. 15/357,850.
Notice of allowance dated Sep. 6, 2017 for U.S. Appl. No. 14/249,710.
Notice of Allowance dated Nov. 17, 2016 for U.S. Appl. No. 14/249,710.
Notice of Allowance dated Nov. 22, 2017 for U.S. Appl. No. 15/359,988.
Notice of Allowance dated Nov. 24, 2017 for U.S. Appl. No. 15/070,605.
Notice of Publication dated Dec. 27, 2018 for U.S. Appl. No. 16/022,256.
Nuala Moran: 'Microbial wealth', chemistry and industry, 78(6), Jun. 1, 2014, pp. 20-23, XP055252922.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189. Nov. 1, 2005.
Numasaki, M. et al., Interleukin-17 promotes angiogenesis and tumor growth. Blood. Apr. 1, 2003;101(7):2620-7. Epub Oct. 31, 2002.
Nutsch et al., T cell tolerance and immunity to commensal bacteria. Current Opinion in Immunology. Aug. 2012; 24 (4):385-391. Epub May 19, 2012.
O'Connell Motherway, M., Kinsella, M., Fitzgerald, G.F., and Sinderen, D. (2013). Transcriptional and functional characterization of genetic elements involved in galacto-oligosaccharide utilization by Bifidobacterium breve UCC2003. Microbial biotechnology 6(1), 67-79. doi: 10.1111/1751-7915.12011. Epub Dec. 2, 2012.
O'Connell Motherway, M., O'Driscoll, J., Fitzgerald Gerald, F., and Van Sinderen, D. (2009). Overcoming the restriction barrier to plasmid transformation and targeted mutagenesis in Bifidobacterium breve UCC2003. Microbial Biotechnology 2(3), 321-332. doi: 10.1111/j.1751-7915.2008.00071.x. Published online Apr. 17, 2009.
O'Connell Motherway, M., Zomer, A., Leahy, S.C., Reunanen, J., Bottacini, F., Claesson, M.J., et al. (2011). Functional genome analysis of Bifidobacterium breve UCC2003 reveals type IVb tight adherence (Tad) pili as an essential and conserved host-colonization factor. Proc Natl Acad Sci U S A 108(27), 11217-11222. doi: 10.1073/pnas.1105380108. Epub Jun. 20, 2011.
Odamaki, Toshitaka et al., "Age-related changes in gut microbiota composition from newborn to centenarian: a cross-sectional study," BMC Microbiology (2016) 16:90, pp. 1-12, DOI 10.1186/S12866-016-0708-5. Published: May 25, 2016.
Odile Menard et al., "Gnotobiotic Mouse Immune Response Induced by *Bifidobacterium* sp. Strains Isolated from Infants", Applied and Environmental Microbiology, Feb. 2008, p. 660-666.
Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Office Action dated Mar. 19, 2019 for U.S. Appl. No. 16/031,024.
Ohashi, Y., Ushida, K. Health-beneficial effects of probiotics: Its mode of action (2009). Animal Science Journal, 80 (4), pp. 361-371.
Oladipo, et al., Bioprotective potential of bacteriocinogenic enterococcus gallinarum strains isolated from some Nigerian fermented foods, and of their bacteriocins. Polish Journal of Microbiology. 2014; 63(4): 415-422.
Olivares, M., Castillejo, G., Varea, V., and Sanz, Y. (2014). Double-blind, randomised, placebo-controlled intervention trial to evaluate the effects of Bifidobacterium longum CECT 7347 in children with newly diagnosed coeliac disease. British Journal of Nutrition 112(1), 30-40. doi: 10.1017/S0007114514000609. Epub Apr. 28, 2014.
Olivera et al. 'Nutritional and physiological responses of young growing rats to diets containing raw cowpea seed meal, protein isolate (globulins), or starch.' Journal of agricultural and food chemistry. 2003, vol. 51, No. 1, pp. 319-325. Publication Date: Dec. 3, 2002.
O'Sullivan et al., "Bacterial Supplementation in the Irritable Bowel Syndrome. A Randomised Double-Blind Placebo-Controlled Cross-over Study", Digest Liver Dis. 2000. pp. 294-301.
Overbeek, R., Begley, T., Butler, R.M., Choudhuri, J.V., Chuang, H.-Y., Cohoon, M., et al. (2005). The Subsystems Approach to Genome Annotation and its Use in the Project to Annotate 1000 Genomes. Nucleic Acids Research 33(17), 5691-5702. doi: 10.1093/nar/gki866.

(56) References Cited

OTHER PUBLICATIONS

Overstreet et al. 'Dysbiosis Characterized by Reduced Abundance of Roseburia is Associated With Increased Severity of Colitis in IL-10-/- Mice'. Gastroenterology. 2011, vol. 140, No. 5, Suppl. 1, pp. S-696.
Pace et al. Macrophage activiation: Priming activity from a T-cell hybridoma is attributable to interferon. (1983) PNAS. 80:3782-6.
Package leaflet: Information for the patient; Humira 20 mg solution for injection in pre-filled syringe, adalimumab, last revised Mar. 2019, 18 pages.
Package leaflet: Information for the user, Remicade 100 mg powder for concentrate for solution for infusion, infliximab, last revised in Mar. 2019, 12 pages.
Package Leaflet: Information for the user, Simponi 100 mg solution for injection in pre-filled pen, golimumab, last revised in Apr. 2019,17 pages.
Pal Rishi et al., "Role of neuroinflammation and latent transcription factors in pathogenesis of Parkinson's disease", Neurological Research, 2016, 38(12), 1111-1122. Epub Nov. 3, 2016.
Pang, et al., Crystal structure of human pirin: an iron-binding nuclear protein and transcription cofactor. Journal of Biological Chemistry, 279(2); Jan. 9, 2004:1491-1498. Epub Oct. 22, 2003.
Parabacteroides distasonis (Eggerth and Gagnon) Sakamoto and Benno (ATCC 8503). Sep. 19, 2017. 2 Pages.
Parfenov A.I., "Pain syndrome in the practice of a gastroenterologist", RMJ Breast Cancer, 2008; 0: 32.
Park, S.K. et al., *Blautia stercoris* sp. nov., isolated from human faeces. International journal of systematic and evolutionary microbiology. 2012; 62(4): 776-779. Epub May 13, 2011.
Patel., R. et al., Determination of 16S rRNA sequences of enterococci and application to species identification of nonmotile enterococcus gallinarum isolates. Journal of clinical microbiology, 1998; 36(11):3399-3407.
Paustian, C., Taylor, P., Johnson, T., Xu, M., Ramirez, N., Rosenthal, K.S., et al. (2013). Extracellular ATP and Toll-like receptor 2 agonists trigger in human monocytes an activation program that favors T helper 17. PLoS One 8(1), e54804. doi: 10.1371/journal.pone.0054804. Epub Jan. 31, 2013.
PCR (Introduction to Biotechniques Series), 2nd ed. (Newton & Graham eds., 1997, Springer Verlag).
PCT/EP2017/025038 International Preliminary Report on Patentability dated Jun. 6, 2018, 8 Pages.
PCT/EP2017/025038 International Search Report and Written Report dated Jun. 12, 2017.
PCT/EP2017/025038 Written Opinion of the International Preliminary Examining Authority dated Jan. 1, 2018.
PCT/EP2017/025038 Written Opinion of the International Preliminary Examining Authority dated Jan. 25, 2018.
PCT/GB2017/052076 Written Opinion of the International Preliminary Examining Authority dated Jun. 21, 2018, 11 Pages.
PCT/GB2017/052077 International Search Report dated Oct. 16, 2017.
PCT/GB2017/052077 Written Opinion dated Oct. 16, 2017.
PCT/GB2017/052077 Written Opinion of the International Preliminary Examining Authority dated Jun. 21, 2018, 10 Pages.
Pearson, WR. An introduction to sequence similarity ("Homology") searching. Current protocols in bioinformatics/editorial board, Andreas D Baxevanis. [et al]. 2013; 0 3:10. 1002/0471250953.bi0301s42. doi:10.1002/0471250953.bi0301s42.
Pedro Berraondo et al., "Cytokines in clinical cancer immunotherapy", British Journal of Cancer, 2019, 120:6-15. Epub Nov. 9, 2018.
Petersen et al. Intestinal colonization with phylogenetic group B2 *Escherichia coli* related to inflammatory bowel disease: a systematic review and meta-analysis. 2015. Scand J Gastroenterol. ;50(10):1199-207. Epub Apr. 24, 2015.
Peterson et al. 'Catecholamines increase conjugative gene transfer between enteric bacteria.' Microbial Pathogensis. 2011, vol. 51, No. 1, pp. 1-8. Epub Mar. 22, 2011.
Petsuriyawong et al. 'Screening of probiotic lactic acid bacteria from piglet feces'. Nature Science. 2011, vol. 45, pp. 245-253.
Ping Dong et al., "The role of intestinal bifidobacteria on immune system development in young rats", Early Human Development 86 (2010) 51-58.
Pinto-Sánchez, M.I., Smecuol, E.C., Temprano, M.P., Sugai, E., González, A., Moreno, M.L., et al. (2017). Bifidobacterium infantis NLS Super Strain Reduces the Expression of α-Defensin-5, a Marker of Innate Immunity, in the Mucosa of Active Celiac Disease Patients. Journal of Clinical Gastroenterology 51(9), 814-817. doi: 10.1097/mcg.0000000000000687.
Pirooznia, Sheila K, and Felice Elefant. "Targeting specific HATs for neurodegenerative disease treatment: translating basic biology to therapeutic possibilities." Frontiers in cellular neuroscience vol. 7 30. Mar. 28, 2013, doi:10.3389/fncel.2013.00030.
Polak J.M. and McGee J.O., In Situ Hybridization: Principles and Practice, Oxford University Press. 1990; pp. vii-viii.
Potrykus (1991) "Gene Transfer to Plants: Assessment of Published Approaches and Results," Annu. Rev. Plant Physiol. Plant Mol. Bioi. 42:205-225.
Prakash, et al., Complete genome sequences of rat and mouse segmented filamentous bacteria, a potent inducer of th17 cell differentiation. Cell Host & Microbe. Sep. 2011;10(3):273-284.
Prospective Studies Collaboration, "Cholesterol, diastolic blood pressure, and stroke: 13,000 strokes in 450,000 people in 45 prospective cohorts. Prospective studies collaboration", Lancet. Dec. 23-30, 1995;346(8991-8992):1647-53.
Pryde et al. 'The microbiology of butyrate formation in the human colon.' FEMS Microbiology Letters. 2002. vol. 217,No. 2, pp. 133-139.
Psaty BM et al, "Health outcomes associated with various antihypertensive therapies used as first-line agents: a network meta-analysis." JAMA. May 21, 2003;289(19):2534-44.
Punt et al. (2002) "Filamentous fungi as cell factories for heterologous protein production," Trends Biotechnol. 20 (5):200-206.
Qin et al. 'A human gut microbial gene catalogue established by metagenomic sequencing.' Nature. 2010, vol. 464, No. 7285, pp. 59-65.
Rajilic-Stojanovic, et al. The first 1000 cultures species of the human gastrointestinal microbiota. FEMS MIcriobiol Rev, vol. 38, 2014. pp. 996-1047. Epub Jun. 27, 2014.
Reddy, K.B.P.K., et al., Role of cryoprotectants on the viability and functional properties of probiotic lactic acid bacteria during freeze drying (2009). Food Biotechnology, 23 (3), pp. 243-265. Published online: Aug. 3, 2009.
Reiff,C. and Kelly,D. Inflammatory bowel disease, gut bacteria and probiotic therapy. International journal of medical microbiology, 2010;300:25-33. Epub Oct. 2, 2009.
Remicade 100mg powder for concentrate for solution for infusion—Summary of Product Characteristics, accessed Oct. 25, 2019, 28 pages.
Reuter, G. (2001). The Lactobacillus and Bifidobacterium microflora of the human intestine: composition and succession. Current Issues in Intestinal Microbiology 2(2), 43-53.
Rhee et al. Toll-Like Receptor 5 Engagement Modulates Tumor Development and Growth in a Mouse Xenograft Model of Human Colon Cancer. Gastroenterology. Aug. 2008;135(2):518-528. Epub Apr. 23, 2008.
Rhee, Young-Kyung et al.., Antitumor Activity of *Bifidobacterium* Spp. isolated from a healthy Korean, Arch Pharm Res vol. 23, No. t, 482-487 2000. Oct. 2000.
Riquelme. Will 4D Pharma be UK's next Microbiome leader? Feb. 2, 2015, LABIOTECH.eu [online].
Robertson, J.M.C., et al., Lack of flagella disadvantages *Salmonella enterica serovar Enteritidis* during the early stages of infection in the rat (2003). Journal of Medical Microbiology, 52 (1), pp. 91-99.
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Roe, et al., DNA Isolation and Sequencing: Essential Techniques. John Wiley & Sons, New York, New York. 1996; pp. v-vii.
Rong, Y., Dong, Z., Hong, Z., Jin, Y., Zhang, W., Zhang, B., et al. (2017). Reactivity toward Bifidobacterium longum and Enterococ-

(56) References Cited

OTHER PUBLICATIONS cus hirae demonstrate robust CD8(+) T cell response and better prognosis in HBV-related hepatocellular carcinoma. Experimental Cell Research 358(2), 352-359. doi: 10.1016/j.yexcr.2017.07.009. Epub Jul. 8, 2017.

Roseburia. Ubiome, 2018. Accessed on Jun. 25, 2018; Available at: https://shop.ubiome.com/pages/roseburia-1.

Round et al. 'The Toll-like receptor 2 pathway establishes colonization by a commensal of the human microbiota.' Science. 2011, vol. 332, No. 6032, pp. 974-977. Epub Apr. 21, 2011.

Rudinger J, "Characteristics of the amino acids as components of a peptide hormone sequence," Peptide Hormones, JA Parsons Edition, University Park Press, Jun. 1976, pp. 1-7.

Ruiz, L., Delgado, S., Ruas-Madiedo, P., Margolles, A., and Sanchez, B. (2016). Proteinaceous Molecules Mediating Bifidobacterium-Host Interactions. Front Microbiol 7, 1193. doi: 10.3389/fmicb.2016.01193. Published online Aug. 3, 2016.

Ruiz, P.A., Hoffmann, M., Szcesny, S., Blaut, M., and Haller, D. (2005). Innate mechanisms for Bifidobacterium lactis to activate transient pro-inflammatory host responses in intestinal epithelial cells after the colonization of germ-free rats. Immunology 115(4), 441-450. doi: 10.1111/j.1365-2567.2005.02176.x.

Russell et al. 'High-protein, reduced-carbohydrate weight-loss diets promote metabolite profiles likely to be detrimental to colonic health.' The American Journal of Clinical Nutrition. 2011, vol. 93, No. 5, pp. 1062-1072. Epub Mar. 9, 2011.

Sagar, et al., Bifidobacterium breve and lactobacillus rhamnosus treatment is as effective as budesonide at reducing inflammation in a murine model for chronic asthma. Respiratory Research. 2014; 15(46):1-17. Published: Apr. 16, 2014.

Saiki, et al., Primer-directed enzymatic amplification of DNA with a thermostable DNA polymerase. 1988. Science, 239. pp. 487-491. Jan. 29, 1988.

Sakamato, et al., *Parabacteroides faecis* sp. nov., isolated from human faeces. International Journal of Systematic and Evolutionary Microbiology (2015), 65, 1342-1346. Epub Feb. 9, 2015.

Sakamoto, et al., *Parabacteroides gordonii* sp. nov., isolated from human blood cultures. International Journal of Systematic and Evolutionary Microbiology (2009), 59, 2843-2847. Epub Jul. 23, 2009.

Sakamoto, et al., *Parabacteroides johnsonii* sp. nov., isolated from human faeces. International Journal of Systematic and Evolutionary Microbiology (2007), 57, 293-296.

Sakamoto, M. et al., Reclassification of *Bacteroides distasonis, Bacteroides goldsteinii and Bacteroides merdae as Parabacteroides distasonis* gen. nov., comb, nov., *Parabacteroides goldsteinii* comb. nov. and *Parabacteroides merdae* comb. nov. International journal of systematic and evolutionary microbiology. 2006; 56: 1599-1605. DOI 10.1099/ijs.0.0641920.

Salix Pharmaceuticals, Inc. FDA Highlights of Prescribing Information—XIFAXAN (rifaximin tablet). Revised Nov. 2015.

Salminen et al. 'Probiotics: how should they be defined?.' Trends in Food Science & Technology. 1999, vol. 10, No. 3, pp. 107-110.

Salonen et al., Gastrointestinal microbia in irritable bowel syndrome: present state and perspectives. Microbiology. 2010; 156: 3205-3215. Epub Aug. 12, 2010.

Savignac HM et al., "Bifidobacteria exert strain-specific effects on stress-related behavior and physiology in BALB/c mice.", Neurogastroenterol Motil. Nov. 2014;26(11):1615-27. doi: 10.1111/nmo.12427. Epub Sep. 24, 2014.

Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.

Scher et al., Expansion of intestinal Prevotella copri correlates with enhanced susceptibility to arthritis. 2013; eLIFE 2, e01202, 20 Pages.

Schiavi, E., Gleinser, M., Molloy, E., Groeger, D., Frei, R., Ferstl, R., et al. (2016). The Surface-Associated Exopolysaccharide of Bifidobacterium longum 35624 Plays an Essential Role in Dampening Host Proinflammatory Responses and Repressing Local TH17 Responses. Appl Environ Microbiol 82(24), 7185-7196. doi: 10.1128/AEM.02238-16.

Schiavi, E., Plattner, S., Rodriguez-Perez, N., Barcik, W., Frei, R., Ferstl, R., et al. (2018). Exopolysaccharide from *Bifidobacterium longum* subsp. *longum* 35624 modulates murine allergic airway responses. Benef Microbes, 1-14. doi: 10.3920/BM2017.0180. Epub May 4, 2018.

Schieck, M. et al., Genetic variation in TH17 pathway genes, childhood asthma, and total serum IgE levels.(2014) J Allergy Clin Immunol. 133(3):888-91. Epub Nov. 1, 2013.

Schleifer, K.H. et al., Transfer of *Streptococcus faecalis* and *Streptococcus faecium* to the Genus *Enterococcus* nom. rev. as *Enterococcus faecalis* comb. nov. and *Enterococcus faecium* comb. nov. Int J Syst Evol Microbiol, Jan. 1984 34: 31-34, doi:10.1099/00207713-34-1-31 . Jan. 1, 1984.

Schmitz, S. et al., A prospective, randomized, blinded, placebo-controlled pilot study on the effect of Enterococcus faecium on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.

Schouten, et al., Cow milk allergy symptoms are reduced in mice fed dietary synbiotics during oral sensitization with whey. J Nutr. Nutritional Immunology. Jul. 2009; 139(7): 1398-403. Epub May 27, 2009.

Schreiber, O, et al., Lactobacillus reuteri prevents colitis by reducing P-selectin-associated leukocyte- and plateletendothelial cell interactions (2009). American Journal of Physiology-Gastrointestinal and Liver Physiology, 296 (3), pp. G534-G542. Epub Jan. 15, 2009.

Schulke et al. (Aug. 26, 2011) "A fusion protein of flagellin and ovalbumin suppresses the 25 TH2 response and prevents murine intestinal allergy," The Journal of Allergy and Clinical Immunology. 128(6):1340-1348.

Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.

Scott et al. 'Substrate-driven gene expression in Roseburia inulinivorans: importance of inducible enzymes in the utilization of inulin and starch.' Proceedings of the National Academy of Sciences. 2011, vol. 108, Supp. 1, pp. 4672-4679. Epub Aug. 2, 2010.

Scuotto, Angelo et al., In silico mining and characterization of bifidobacterial lipoprotein with CHHP domain secreted in an aggregated form, International J. of Biol. Macromolecutes 82(2016), 653-662. Oct. 12, 2015.

Sczesnak, et al., The genome of th17 cell-inducing segmented filamentous bacteria reveals extensive auxotrophy and adaptations to the intestinal environment. Cell Host Microbe. Sep. 2011;10 (3):260-272.

Severijnen, A. J. et al., Chronic Arthritis Induced in Rats by Cell Wall Fragments of *Eubacterium* Species from the Human Intestinal Flora. Infection and Immunity, Feb. 1990, vol. 58, No. 2, 523-528.

Sgadari, C. et al., Interferon-inducible protein-10 identified as a mediator of tumor necrosis in vivo. (1996) PNAS. 93:13791-6. Nov. 26, 1996.

Sgadari et al. Mig, the Monokine Induced by Interferon-g, Promotes Tumor Necrosis In Vivo. (1997) Blood. 89:2635-43.

Shabgah, A.G. et al., Interleukin-17 in human inflammatory diseases. Postepy Dermatol Alergol. Aug. 2014; 31(4): 256-261. Epub Sep. 8, 2014.

Shevach et al., Current Protocols in Immunology. John Wiley & Sons. New York, New York. 1992. Table of Contents only, as accessed online at URL: http://www.4ulr.com/products/currentprotocols/immunology_toc.html. [Last Accessed Jun. 18, 2015].

Simon, et al., Peptoids: A modular approach to drug discover, Oct. 1992. PNAS, 89(20):9367-9371.

Simponi 100 mg solution for injection in pre-filled pen—Summary of Product Characteristics, https://www.medicines.org.uk/emc/products/5133/smpc/print, accessed Oct. 25, 2019, 21 pages.

Simpson-Herren, L. et al., Kinetic parameters and growth curves for experimental tumor systems. Cancer Chemother Rep. Jun. 1970;54(3):143-74.

(56) References Cited

OTHER PUBLICATIONS

Sisson, G. et al., Randomised clinical trial: a liquid multi-strain probiotic vs. placebo in the irritable bowel syndrome—a 12 week double-blind study. Aliment Pharmacol Ther. 2014; 40: 51-62. Epub May 11, 2014.
Sivan, A., Corrales, L., Hubert, N., Williams, J.B., Aquino-Michaels, K., Earley, Z.M., et al. (2015). Commensal Bifidobacterium promotes antitumor immunity and facilitates anti-PD-L1 efficacy. Science 350(6264), 1084-1089. doi: 10.1126/science.aac4255. Epub Nov. 5, 2015.
Sivieri, K. et al., Probiotic enterococcus faecium CRL 183 inhibit chemically induced colon cancer in male wistar rats. Eur Food Res Technol. 2008; 228:231-237.
Skolnick, et al. From genes to protein structure and function: novel applications of computational approaches in the genomic era. Trends Biotechnol. Jan. 2000;18(1):34-9. Review.
Skountzou, et al., *Salmonella flagellins* are potent adjuvants for intranasally administered whole inactivated influenza vaccine. Vaccine. May 2010; 28(24):4103-4112.
Smith and Waterman, "Comparison of biosequences", Advances in Applied Mathematics, vol. 2, Issue 4, Dec. 1981, pp. 482-489.
Smith, C.L., et al., Lactobacillus fermentum BRII and fructo-oligosaccharide partially reduce jejunal inflammation in a model of intestinal mucositis in rats (2008). Nutrition and Cancer, 60(6), pp. 757-767.
Sokol et al. 'Faecalibacterium prausnitzii is an anti-inflammatory commensal bacterium identified by gut microbiota analysis of Crohn disease patients.' Proceedings of the National Academy of Sciences. 2008, vol. 105, No. 43, pp. 6731-16736. Epub Oct. 20, 2008.
Sokol et al. 'Low counts of Faecalibacterium prausnitzii in colitis microbiota.' Inflammatory bowel diseases. 2009, vol. 15, No. 8, pp. 1183-1189. Feb. 23, 2009.
Song et al., Impact of Schistosoma japonicum Infection on Collagen-Induced Arthritis in DBA/1 Mice: A Murine Model of Human Rheumatoid Arthritis. 2011; PLoS ONE 6, e23453, 10 pages. Epub Aug. 8, 2011.
Song, Yuli et al., *Bacteroides goldsteinii* sp. nov. Isolated from Clinical Specimens of Human Intestinal Origin, J. Clinical Microbiology, Sep. 2005, p. 4522-4527. DOI:10.1128/JCM.43.9.4522-4527.2005.
Sonnenburg, et al., Genomic and Metabolic Studies of the Impact of Probiotics on a Model Gut Symbiont and Host. PLoS Biol, 2006, 4(12): e413. https://doi.org/10.1371/journal.pbio.0040413.
Spor, A. et al., Unravelling the effects of the environment and host genotype on the gut microbiome. Nat Rev Microbiol. Apr. 2011;9(4):279-90. doi: 10.1038/nrmicro2540.
Srutkova, D. et al., Efficiency of PCR-based methods in discriminating *Bifidobacterium longum* ssp. *longum* and *Bifidobacterium longum* ssp. infantis strains of human origin. J Microbiol Methods. Oct. 2011;87(1):10-6. doi: 10.1016/j.mimet.2011.06.014. Epub Jul. 2, 2011.
Stanton et al. (1983) "*Roseburia cecicola* gen. nov., sp. nov., a Motile, Obligately Anaerobic Bacterium from a Mouse Cecum," Int. J. Syst. Bacterial. 33:618-627.
Stokholm, et al., Maturation of the gut microbiome and risk of asthma in childhood. Nature Communications, 2018; 9(141): 1-10.
Stoll et al., Altered microbiota associated with abnormal humoral immune responses to commensal organisms in enthesitis-related arthritis, 2014; Arthritis Res Ther. 16:486.
Strasser, S. et al., Influence of lyophilization, fluidized bed drying, addition of protectants, and storage on the viability of lactic acid bacteria (2009). Journal of Applied Microbiology, 107(1), pp. 167-177. Epub Mar. 3, 2009.
Strickertsson, J.A. et al., Enterococcus faecalis Infection and Reactive *Oxygen* Species Down-Regulates the miR-17-92 Cluster in Gastric Adenocarcinoma Cell Culture. Genes 2014, 5(3), 726-738.
Strobel, H.J. Basic laboratory culture methods for anaerobic bacteria. Methods Mol Biol. 2009;581:247-61. doi: 10.1007/978-1-60761-214-8_16.
Strus et al. Distinct effects of Lactobacillus plantarum KL30B and *Escherichia coli* 3A1 on the induction and development of acute and chronic inflammation. 2015. Cent Eur J Immunol.40(4):420-30. Epub Jan. 15, 2016.
Sudha B. Singh and Henry C. Lin, "Hydrogen Sulfide in Physiology and Diseases of the Digestive Tract", Microorganisms 2015, 3, 866-889; doi:10.3390/microorganisms3040866.
Sun, D. et al., The role of Th17-associated cytokines in the pathogenesis of experimental autoimmune uveitis (EAU). (2015) Cytokine. 74(1):76-80. Epub Mar. 2, 2015.
Sun, et al., Exploring gut microbes in human health and disease: Pushing the envelope. Genes Dis. Dec. 2014; 1(2):132-139.doi:10.1016/j.gendis.2014.08.001. Published online Aug. 10, 2014.
Supplement to: Israel, et al., Severe and difficult-to-treat asthma in adults. N Engl J Med 2017; 377:965-76.
Suzanne L. Topalian et al., "Survival, Durable Tumor Remission, and Long-Term Safety in Patients With Advanced Melanoma Receiving Nivolumab", Journal of Clinical Oncology, vol. 32, No. 10, Apr. 1, 2014, pp. 1-12.
Tahoun, A., Masutani, H., El-Sharkawy, H., Gillespie, T., Honda, R.P., Kuwata, K., et al. (2017). Capsular polysaccharide inhibits adhesion of Bifidobacterium longum 105-A to enterocyte-like Caco-2 cells and phagocytosis by macrophages. Gut Pathog 9, 27. doi: 10.1186/s13099-017-0177-x.
Takashi Nakamura et al., "Evaluation of the Effects of Dietary Organic Germanium, Ge-132, and Raffinose Supplementation on Caecal Flora in Rats", Bioscience of Microbiota, Food and Health vol. 31 (2), 37-45, 2012. Published online Apr. 20, 2012.
Tamanai-Shacoori, et al., *Roseburia* spp.: a marker of health?. Future Microbiology Review 12(2), 157-170 (2017). Feb. 2017.
Tan, Hai-Qin et al., *Parabacteroides chartae* sp. nov., an obligately anaerobic species from wastewater of a paper mill, International Journal of systematic and Evolutionary Microbiology (2012), 62-2613-2617, DOI 10.1099/ijs.0.038000-0.
Tanaka, K. and Watanabe, K., In Vitro tebipenem activity against anaerobic bacteria. Japanese Journal of Chemotherapy. Mar. 2009. vol. 57 S-1.
Tang, Ying et al., "Inhibiting Histone Deacetylase 2 (HDAC2) Promotes Functional Recovery From Stroke" 2017, Journal of the American Heart Association, 6(10), 1-28. Oct. 5, 2017.
Tang,PhD, Jiaqi et al., "Prenatal Hypoxia Induced Dysfunction in Cerebral Arteries of Offspring Rats" 2017, Journal of the American Heart Association, 6(10), 1-12. Oct. 3, 2017.
Tap et al. Towards the human intestinal microbiota phylogenetic core. 2009. Environ Microbiol, 11 (10):2574-84. Epub Jul. 6, 2009.
Tatusova, et al., Erratum to BLAST 2 Sequences, a new tool for comparing protein and nucleotide sequences [FEMS Microbiol. 174 (1999) 247-250], FEMS Microbial. Lett. 1999;177(1):187-188.
Tatusova et al. (1999) "BLAST 2 Sequences, a new tool for comparing protein and nucleotide sequences," FEMS Microbial. Lett. 174(2):247-250.
Teng, L. J. et al., PCR Assay for Species-Specific Identification of Bacteroides the taiotaomicron. J Clin Microbiol38, 1672-1675 (2000).
Terciz, Janos et al., Inflammation and Colon Cancer, Gastroenterology, 2010: 138: 2101-2114.
Tesmer, LA. et al., Th17 cells in human disease. Immunol Rev. 2008;223:87-113.
Tilg, et al., Roseburia hominis: a novel guilty player in ulcerative colitis pathogenesis? Gut, Oct. 14, 2013;63(8)1204-1205. Epub Oct. 14, 2013.
Tomas, M.S.J., et al., Stability of freeze-dried vaginal Lactobacillus strains in the presence of different lyoprotectors (2009). Canadian Journal of Microbiology, 55 (5), pp. 544-552.
Tomosada, Y., Villena, J., Murata, K., Chiba, E., Shimazu, T., Aso, H., et al. (2013). Immunoregulatory Effect of Bifidobacteria Strains in Porcine Intestinal Epithelial Cells through Modulation of Ubiquitin-Editing Enzyme A20 Expression. PLOS ONE 8(3), e59259. doi: 10.1371/journal.pone.0059259. Epub Mar. 26, 2013.
Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670. Epub May 14, 2014.

(56) References Cited

OTHER PUBLICATIONS

Travis, et al. Complete genome sequence of the human gut symbiont Roseburia hominis. Genome announcements. 2015; 3(6):e01286-15. Published online Nov. 5, 2015.
Tremaroli, et al., A role for the gut microbiota in energy harvesting? Gut. Dec. 2010; 59(12):1589-1590.
Trueman (1995) "Heterologous Expression in Yeast," Methods Molecular Biology. 49:341-354.
Tsukinowa, et al., Fecal microbiota of a dugong (Dugong dugong) in captivity at Toba Aquarium. J. Gen. Appl. Microbiol., 54, 25-38 (2008).
Turnbaugh et al. A core gut microbiome in obese and lean twins. Jan. 22, 2009. Nature, 457(7228): 480-484. Epub Nov. 30, 2008.
Turnbaugh, et al., An obesity-associated gut microbiome with increased capacity for energy harvest. Nature. Dec. 2006;444(7122):1027-1031.
Turnbaugh et al., Diet-induced obesity is linked to marked but reversible alterations in the mouse distal gut microbiome. Cell Host & Microbe. Apr. 2008;3(4):213-223.
Turner (1994) "Vectors for genetic manipulation," In; Martinelli, S.D.; Kinghorn J. R.: Eds. Aspergillus: 50 years on. Progress in industrial microbiology. vol. 29. Elsevier. Amserdam, The Netherlands. pp. 641-666.
Turroni, F., Taverniti V Fau—Ruas-Madiedo, P., Ruas-Madiedo P Fau—Duranti, S., Duranti S Fau—Guglielmetti, S., Guglielmetti S Fau—Lugli, G.A., Lugli Ga Fau—Gioiosa, L., et al. (2014). Bifidobacterium bifidum PRL2010 modulates the host innate immune response. Appl Environ Microbiol 80(1098-5336 (Electronic)), 730-740.
Tzortzis, G., et al., Modulation of anti-pathogenic activity in canine-derived *Lactobacillus* species by carbohydrate growth substrate (2004). Journal of Applied Microbiology, 96 (3), pp. 552-559.
Udayappan, et al., Oral treatment with Eubacterium hallii improves insulin sensitivity in db/db mice. NPJ Biofilms and microbiomes, vol. 2, Jul. 6, 2016; p. 16009.
Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.
Ukena, et al., Probiotic *Escherichia coli* Nissle 1917 inhibits leaky gut by enhancing mucosal integrity, PloS one. Dec. 2007;2(12):e1308.
Untergasser, A., Nijveen, H., Rao, X., Bisseling, T., Geurts, R., and Leunissen, J.A. (2007). Primer3Plus, an enhanced web interface to Primer3. Nucleic Acids Res 35(Web Server issue), W71-74. doi: 10.1093/nar/gkm306. Epub May 7, 2007.
U.S. Appl. No. 15/357,936 Notice of Allowance dated Apr. 18, 2018.
U.S. Appl. No. 15/359,144 Notice of Allowance dated Sep. 4, 2018.
U.S. Appl. No. 15/359,972 Notice of Allowance dated Aug. 8, 2018.
U.S. Appl. No. 15/359,988 Notice of Allowance dated Mar. 2, 2018.
U.S. Appl. No. 15/359,988 Notice of Allowance dated Mar. 16, 2018.
U.S. Appl. No. 15/592,178 Notice of Allowance dated Apr. 12, 2018.
U.S. Appl. No. 15/592,178 Notice of Allowance dated Jul. 12, 2018.
U.S. Appl. No. 15/631,945 Notice of Allowance dated Oct. 18, 2018.
U.S. Appl. No. 15/700,007 Notice of Allowance dated Oct. 17, 2018.
U.S. Appl. No. 15/915,885 Notice of Allowance dated May 23, 2018.
U.S. Appl. No. 15/915,889 Notice of Allowance dated Jun. 4, 2018.
U.S. Appl. No. 15/916,167 Notice of Allowance dated May 31, 2018.
U.S. Appl. No. 15/916,202 Notice of Allowance dated Jun. 11, 2018.
U.S. Appl. No. 15/916,205 Notice of Allowance dated May 30, 2018.
U.S. Appl. No. 15/359,144 Office Action dated Apr. 10, 2018.
U.S. Appl. No. 15/359,972 Office Action dated Apr. 4, 2018.
U.S. Appl. No. 15/431,393 Office Action dated Jul. 30, 2018.
U.S. Appl. No. 15/631,945 Office Action dated Jul. 5, 2018.
U.S. Appl. No. 15/631,945 Office Action dated May 15, 2018.
U.S. Appl. No. 15/631,952 Office Action dated Feb. 16, 2018.
U.S. Appl. No. 15/631,952 Office Action dated Jul. 19, 2018.
U.S. Appl. No. 15/673,270 Office Action dated Apr. 10, 2018.
U.S. Appl. No. 15/679,857 Office Action dated Aug. 6, 2018.
U.S. Appl. No. 15/679,857 Office Action dated Feb. 14, 2018.
U.S. Appl. No. 15/700,007 Non-Final Office Action dated Jun. 10, 2019.
U.S. Appl. No. 15/700,007 Office Action dated Jun. 1, 2018.
U.S. Appl. No. 15/704,245 Non-Final Office Action dated Jul. 3, 2019.
U.S. Appl. No. 15/704,245 Non-Office Action dated Dec. 16, 2019.
U.S. Appl. No. 15/704,245 Office Action dated Sep. 17, 2018.
U.S. Appl. No. 15/803,723 Notice of Allowance dated Feb. 13, 2018.
U.S. Appl. No. 15/842,635 Office Action dated Aug. 27, 2018.
U.S. Appl. No. 16/100,349 Final Office Action dated May 1, 2019.
U.S. Appl. No. 15/842,635 Non-Final Office Action Dated May 29, 2019.
U.S. Appl. No. 16/022,577 Non-Final Office Action dated Jul. 9, 2019.
Van De Bogert, et al., Immunomodulatory properties of *Streptococcus* and veillonella isolates from the human small intestine microbiota, PLOS One, Dec. 2014: 1-20, DOI:10.1371/journal.pone.0114277.
Van de Pol, M.A. et al., Synbiotics reduce allergen-induced T-helper 2 respond and improve peak expiatory flow in allergic asthmatics, Allergy 2011;66:39-47. Epub Aug. 17, 2010.
Van De Veerdonk, et al., The Anti-CD20 antibody rituximab reduces the Th17 cell response. Arthritis & Rheumatism. Jun. 2011; 63(6):1507-1516.
Van Immerseel et al. 'Butyric acid-producing anaerobic bacteria as a novel probiotic treatment approach for inflammatory bowel disease.' Journal of medical microbiology. 2010, vol. 59, No. 2, pp. 141-143. Epub Nov. 26, 2009.
Van Nevel et al., "Control of Rumen Methanogenesis." Environmental Monitoring and Assessment, vol. 42, 1996, pp. 73097, XP000979267.
Van Tilburg, M. Can we treat visceral hypersensitivity in functional abdominal pain? Lancet Gastroenterolhepatol, 2017; 2 Pages. 2(10):694-695. doi: 10.1016/S2468-1253(17)30258-3. Epub Aug. 18, 2017.
Verheijden, K.A.T. et al., The development of allergic inflammation in a murine house dust mite asthma is suppressed by symbiotic mixtures of non-digestible oligosaccharides and Bifidobacterium breve M-16V; Eur. J. Nut. (2016) 55: 1141-1151, DOI 10.1007, 500394-015-0928-8. Epub May 24, 2015.
Vetrovsky, T. and Baldrian, P., The variability of the 16S rRNA gene in bacterial genomes and its consequences for bacterial community analyses. Plos One. Feb. 2013; 8(2): e57923. Epub Feb. 27, 2013.
Viaud, Sophie et al. "The intestinal microbiota modulates the anticancer immune effects of cyclophosphamide." Science (New York, N.Y.) vol. 342,6161 (2013): 971-6. doi:10.1126/science.1240537. Nov. 22, 2013.
Vijay-Kumar, et al., Deletion of TLR5 results in 10 spontaneous colitis in mice. The Journal of Clinical Investigation. Dec. 2007;117(12):3909-3921.
Vijay-Kumar et al., Flagellin Treatment Protects against Chemicals, Bacteria, Viruses, and Radiation. The Journal of Immunology. 2008;180(12):8280-8285.
Vorstman, Jacob A S et al. "Proline affects brain function in 22q11DS children with the low activity COMT 158 allele." Neuropsychopharmacology : official publication of the American College of Neuropsychopharmacology vol. 34,3 (2009): 739-46. doi:10.1038/npp.2008.132. Epub Sep. 3, 2008.
Waisman, Ari et al., "The role of IL-17 in CNS diseases", Acta Neuropathologica, Springer Verlag, Berlin, DE, 2015, vol. 129, No. 5, 625-637. Epub Feb. 26, 2015.
Walker et al. 'Dominant and diet-responsive groups of bacteria within the human colonic microbiota.' The ISME Journal. 2010, vol. 5, No. 2, pp. 220-230. Epub Aug. 5, 2010.

(56) References Cited

OTHER PUBLICATIONS

Wang, Chun-Sai-Er, et al., VSL#3 can prevent ulcerative colitis-associated carcinogenesis in mice, Oct. 7, 2018, vol. 24, Issue 37, pp. 4254-4262.
Wang et al. 16S rRNA gene-based analysis of fecal microbiota from preterm infants with and without necrotizing enterocolitis. 2009. ISME J. 3(8): 944-954. Epub Apr. 16, 2009.
Wang, Feng, Bifidobacterium can mitigate intestinal immunopathology in the context of CTLA-4 blockade, PNA, Jan. 2, 2018 vol. 115, No. 1, pp. 157-161. Epub Dec. 18, 2017.
Wang, G., Xia, Y., Cui, J., Gu, Z., Song, Y., Q., C.Y., et al. (2014). The Roles of Moonlighting Proteins in Bacteria. Current Issues in Molecular Biology 16, 15-22. Epub Jul. 22, 2013.
Wang, Huiying et al. “Effect of Probiotics on Central Nervous System Functions in Animals and Humans: A Systematic Review.” Journal of neurogastroenterology and motility vol. 22,4 (2016): 589-605. doi:10.5056/jnm16018. Oct. 30, 2016.
Wang, R.F., and Kushner, S.R. (1991). Construction of versatile low-copy-number vectors for cloning, sequencing and gene expression in *Escherichia coli*. Gene 100, 195-199. doi: https://doi.org/10.1016/0378-1119(91)90366-J.
Wang W., Lyophilization and development of solid protein pharmaceuticals. International J. Pharmaceutics 203: 1-60, 2000.
Wang, Yan, and Lloyd H Kasper. “The role of microbiome in central nervous system disorders.” Brain, behavior, and immunity vol. 38 (2014): 1-12. doi:10.1016/j.bbi.2013.12.015. May 2014.
Watson, et al., Signal transduction in Campylobacter jejuni-induced cytokine production. Cellular Microbiology. 2005;7(5):655-665.
Wei, X., Yan, X., Chen, X., Yang, Z., Li, H., Zou, D., et al. (2014). Proteomic analysis of the interaction of Bifidobacterium longum NCC2705 with the intestine cells Caco-2 and identification of plasminogen receptors. J Proteomics 108, 89-98. doi: 10.1016/j.jprot.2014.04.038. Epub May 17, 2014.
Weigel, et al., Comparative analysis of murine marrow-derived dendritic cells generated by Flt3L or GMCSF/IL-4 and matured with immune stimulatory agents on the in vivo induction of antileukemia responses. Blood. Dec. 2002;100(12):4169-4176. Epub Aug. 8, 2002.
Welman, A.D., and Maddox, I.S. (2003). Exopolysaccharides from lactic acid bacteria: perspectives and challenges. Trends in Biotechnology 21(6), 269-274. doi: https://doi.org/10.1016/S0167-7799(03)00107-0.
Wendler, et al., Identification of a pirin, a novel highly conserved nuclear protein. J. Biol Chem. Mar. 28, 1997; 272(13):8482-9.
Wenzel, S.E., Asthma phenotypes: the evolution from clinical to molecular approaches, Nature medicine, May 2012; 18(5):716-725.
Werth, et al., The transcription factor grainyhead-like 2 regulates the molecular composition of the epithelial apical junctional complex. Development. 2010;37(22):3835-3845.
Westermann, C., Gleinser, M., Corr, S.C., and Riedel, C.U. (2016). A Critical Evaluation of Bifidobacterial Adhesion to the Host Tissue. Front Microbiol 7, 1220. doi: 10.3389/fmicb.2016.01220. Aug. 5, 2016.
Williams, N.T. Probiotics (2010). American Journal of Health-System Pharmacy, 67 (6), pp. 449-458. Mar. 15, 2010.
Wilson, et al., The TLR5 ligand flagellin promotes asthma by priming allergic responses to indoor allergens. Nature Medicine. Nov. 2012;18(11):1705-1710.
Workman et al. Guidelines for the welfare and use of animals in cancer research (2010) Br. J. Cancer. 102:1555-77.
Written Opinion for PCT/US17/066709 dated Jun. 4, 2018 (Published as WO2018112363) owned by Evelo Biosciences, Inc.
Written Opinion for PCT/US2017/066713 dated Aug. 13, 2018 (Published as WO2018/112365) owned by Evelo Biosciences, Inc.
Wrzosek, et al., Bacteroides thetaiotaomicron and Faecalibacterium prausnitzii influence the production of mucus glycans and the development of globlet cells in the colonic epithelium of a gnotobiotic model rodent. BMC biology, 2013;11(61):1-13. Published: May 21, 2013.
Wunderlich, P.F. et al., Double-blind report on the efficacy of lactic acid-producing enterococcus SF68 in the prevention of antibiotic-associated diarrhoea and in the treatment of acute diarrhoea. The journal of international medical research. 1989; 17: 333-338.
Xie et al. Short communication: Modulation of the small intestinal microbial community composition over short-term or long-term administration with Lactobacillus plantarum ZDY2013. 2016. Journal Dairy Sci. 99:6913-6921 . Epub Jun. 16, 2016.
Xu, et al., A genomic view of the human-Bacteroides thetaiotaomicron symbiosis. Science. Mar. 28, 2003; 299(5615):2074-6.
Xu, et al., Differential development of murine dendritic cells by GM-CSF versus Flt3 ligand has implications for inflammation and trafficking. J. Immunology. 2007;179(11):7577-7584.
Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.
Xu, J. et al., “Message from a human gut symbiont: sensitivity is a prerequisite for sharing”, Trends in microbiology, 12(1), Jan. 1, 2004: pp. 21-28, XP055253932.
Yang, Changa et al., Non-invasive imaging of toll-like receptor 5 expressing using 131 labelled mAb in the mice bearing H22 tumors, Oncol. Lett. 2014., 7(6).1919-1924., Published online Apr. 2014.il2. DOI: 10.3892/ol.2014.2025.
Yang, Changya et al., Non-invasive imaging of Toll-like receptor 5 expression using 131l-labeled mAb in the mice bearing H22 tumors, Oncology Letters, 7: 1919-1924, 2014, DOI: 10.3892/oo.2014.2025.
Yang, Fang, “The clinical significance of the imbalance of TH17 and Treg cells and their related cytokines in peripheral blood of Parkinson’s disease patients”, International Journal of clinical and experimental medicine, 2016, vol. 9, No. 9, 17946-17951.
Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.
Yao, W., et al., Cultivation-Independent Analysis of the Development of the *Lactobacillus* spp. Community in the Intestinal Tract of Newborn Piglets (2011)Agricultural Sciences in China, 10(3), pp. 438-447.
Ye, X. et al., The Role of IL-23/Th17 Pathway in Patients with Primary Immune Thrombocytopenia. (2015) PLoS One. 10(1):e0117704. Jan. 26, 2015.
Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.
Yoon, et al., Structural basis of TLR5-flagellin recognition and signaling. Science. Feb. 2012; 335(6070):859-864. Feb. 17, 2012.
Yoshinori Kohwi et al., “Antitumor Effect of Bifidobacterium Infant’s in Mice”, Gann, 69, 613-618; Oct. 1978.
Yq et al. Therapeutic Modulation of the Gut Microbiota in IBD—More Questions to Be Answered. (2016). J. Dig. Dis., Oct. 15, 1751-2980, 12422, First published:Oct. 15, 2016.
Yu, Dah-Shyong et al., Bacille Calmette-Guerin can induce cellular apoptosis of urothelial cancer directly through toll-like receptor 7 activation, Kaohsiung Journal of Medical Sciences (2015) 31,391-397.
Yu, et al., Utilization of major fucosylated and sialylated human milk oligosaccharides by isolated human gut microbes. Glycobiology, 2013; 23(11):1281-1292. Epub Sep. 7, 2013.
Yu, N.Y., Wagner, J.R., Laird, M.R., Melli, G., Rey, S., Lo, R., et al. (2010a). PSORTb 3.0: improved protein subcellular localization prediction with refined localization subcategories and predictive capabilities for all prokaryotes. Bioinformatics 26(13), 1608-1615. doi: 10.1093/bioinformatics/btq249. Epub May 13, 2010.
Yun, J.H., et al., Isolation and characterization of potential pro biotic lactobacilli from pig feces (2009). Journal of Basic Microbiology, 49 (2), pp. 220-226.
Yurdusev, N. et al., Antagonistic Effect Exerted by Three Strictly Anaerobic Strains Against Various Strains of Clostridium Perfringens in Gnotobiotic Rodent Intestines. Can J Microbiol 33, 226-231 (1987).
Yurdusev, N. et al., InfectInunun 57,724-731 (1989).

(56) References Cited

OTHER PUBLICATIONS

Yutin, N. and Galperin, M.Y., A genomic update on clostridial phylogeny:Gram-negative spore formers and other misplaced clostridia. Environmental microbiology. Oct. 2013; 15(10): 2631-2641. Epub Jul. 9, 2013.

Zadori, Denes et al., "Kynurenines in Parkinson's disease: therapeutic perspectives", 2012, Journal of Neural Transmission, 119, 2, 275-283. Epub Aug. 20, 2011.

Zhang, B. et al., Oral administration of enterococcus faecalis FK-23 suppresses Th17 cell development and attenuates allergic airway responses in mice. International journal of molecular medicine. 2012; 30:248-254. Epub May 24, 2012.

Zhang, B. et al., The Prevalence of Th17 Cells in Patients With Gastric Cancer. 2008. Biochem Biophys Res Commun 374 (3), 533-537. Epub Jul. 23, 2008.

Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.

Zheng, B. et al., Bifidobacterium breve attenuates murine dextran sodium sulfate-induced colitis and increases regulatory T cell responses. PLOS one. May 2014; 9(5). May 2, 2014.

Zheng, B., van Bergenhenegouwen, J., Overbeek, S., van de Kant, H.J., Garssen, J., Folkerts, G., et al. (2014). Bifidobacterium breve attenuates murine dextran sodium sulfate-induced colitis and increases regulatory T cell responses. PLoS One 9(5), e95441. doi: 10.1371/journal.pone.0095441. May 2, 2014.

Zheng, Bin et al., Bifidobacterium breve Attenuates Murine Dextran Sodium Sulfate-Induced Colitis and Increases Regulatory T Cell Responses, PLOS ONE, vol. 9, Issue 5, e95441, May 2, 2014.

Zheng, Zhen et al. "Peripheral brain-derived neurotrophic factor in autism spectrum disorder: a systematic review and meta-analysis", 2016, Scientific Reports, 6(31241) 1-8.

Zhongyuan, T. et al., The inflammation regulation effects of enterococcus faecium HDRsEf1 on human enterocyte-like HT-29 cells. Animal cells and systems. Mar. 22, 2016;20(2):70-76.

Zhou et al. Central and peripheral hypersensitivity in the irritable bowel syndrome. 2010. Pain. 148(3): 454-461. Epub Jan. 13, 2010.

Zhou, Linghong, and Jane A Foster. "Psychobiotics and the gut-brain axis: in the pursuit of happiness." Neuropsychiatric disease and treatment vol. 11 715-23. Mar. 16, 2015, doi:10.2147/NDT.S61997.

Zhu, S. and Qian, Y., IL-17/IL-17 receptor system in autoimmune disease: mechanisms and therapeutic potential. Clinical Science (2012) 122, 487-511.

Zitomersky, N. et al., Characterization of Adherent Bacteroidales from Intestinal Biopsies of Children and Young Adults with Inflammatory Bowel Disease. PLOS one. 2013; 8(6). e63686. Published online Jun. 11, 2013.

Zitvogel, et al., Type I interferons in anticancer immunity. Nature Reviews. Jul. 2015:405-414. Epub Jun. 1, 2015.

Johnson, J.S. et al., Evaluation of 16S rRNA gene sequencing for species and strain-level microbiome analysis, Nature Communications, 2019; 10:5029: 1-11.

Kyrpides et al., Genomic Encyclopedia of Bacteria and Archaea: Sequencing a Myriad of Type Strains, PLoS Biol, 2014, vol. 12, Issue 8, pp. 1-7.

Schiel-Benglesdorf et al., Pathway engineering and synthetic biology using acetogens, FEBS Letters, 2012, vol. 586, Issue 15, pp. 2191-2198.

* cited by examiner

Impact of BH lyophilisate on microbiota fermentation – caecal sulphides

COMPOSITIONS COMPRISING BACTERIAL STRAINS

CROSS-REFERENCE

This application is a continuation of U.S. application Ser. No. 16/022,484, filed Jun. 28, 2018, now U.S. Pat. No. 10,583,158, issued Mar. 10, 2020, which is a continuation of U.S. application Ser. No. 15/916,202, filed Mar. 8, 2018, now U.S. Pat. No. 10,086,023, issued Oct. 2, 2018, which is a continuation of International Application No. PCT/EP2017/025038, filed Mar. 6, 2017, which claims priority to: Great Britain Application No. 1603817.6, filed Mar. 4, 2016; Great Britain Application No. 1612191.5, filed Jul. 13, 2016; and Great Britain Application No. 1616022.8, filed Sep. 20, 2016; all of which are hereby incorporated by reference in their entirety. Further, all publications, patents, and patent applications mentioned in this specification are herein incorporated by reference in their entirety to the same extent as if each individual publication, patent, or patent application was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Dec. 13, 2019, is named 49455-718.304-Seq Listing and is 9,843 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 1500 different phylotypes dominated in abundance levels by two major bacterial divisions (phyla), the Bacteroidetes and the Firmicutes [2-3]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host and additional health benefits. Similarly, the immunological importance of the gut microbiota is well-recognized and is exemplified in germfree animals which have an impaired immune system that is functionally reconstituted following the introduction of commensal bacteria [4-6].

Dramatic changes in microbiota composition have been documented in gastrointestinal disorders such as inflammatory bowel disease (IBD). For example, the levels of *Clostridium* cluster XIVa and *Clostridium* cluster XI (*F. prausnitzii*) bacteria are reduced in IBD patients whilst numbers of *E. coli* are increased, suggesting a shift in the balance of symbionts and pathobionts within the gut [7-11].

In recognition of the potential positive effect that certain bacterial strains may have on the animal gut, various strains have been proposed for use in the treatment of various diseases (see, for example, [12-15]). A number of strains, including mostly *Lactobacillus* and *Bifidobacterium* strains, have been proposed for use in treating various bowel disorders (see [16] for a review). Strains of the genus *Blautia* have also been proposed for use in modulating the microbial balance of the digestive ecosystem (WO 01/85187). However, the relationship between different bacterial strains and different diseases, and the precise effects of particular bacterial strains on the gut and at a systemic level and on any particular types of diseases, are poorly characterised.

There is a requirement for the potential effects of gut bacteria to be characterised so that new therapies using gut bacteria can be developed.

SUMMARY OF THE INVENTION

The inventors have developed new therapies for treating and preventing visceral hypersensitivity. In particular, the inventors have identified that bacterial strains from the genus *Blautia* can be effective for reducing visceral hypersensitivity. As described in the examples, oral administration of compositions comprising *Blautia hydrogenotrophica* may reduce visceral hypersensitivity in rat models of visceral hypersensitivity and irritable bowel syndrome (IBS). Therefore, in a first embodiment, the invention provides a composition comprising a bacterial strain of the genus *Blautia*, for use in a method of treating or preventing visceral hypersensitivity.

In preferred embodiments, the invention provides a composition comprising a bacterial strain of the genus *Blautia*, for use in a method of treating or preventing visceral hypersensitivity in a subject diagnosed with Crohn's disease, ulcerative colitis, functional dyspepsia or, more preferably, IBS. In other preferred embodiments, the invention provides a composition comprising a bacterial strain of the genus *Blautia*, for use in a method of treating or preventing visceral hypersensitivity in a subject diagnosed with Crohn's disease, ulcerative colitis, functional dyspepsia, infantile colic or, more preferably, IBS.

In further preferred embodiments, the invention provides a composition comprising a bacterial strain of the genus *Blautia*, for use in treating or preventing visceral hypersensitivity in the abdomen, preferably in the gastrointestinal tract, and most preferably in the lower gastrointestinal tract. In further embodiments, the compositions of the invention are for use in treating or preventing visceral hypersensitivity in the caecum, colon or rectum.

In preferred embodiments of the invention, the bacterial strain in the composition is of *Blautia hydrogenotrophica*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Blautia hydrogenotrophica*. Preferably, the bacterial strain has a 16s rRNA sequence that is at least 95%, 96%, 97%, 98%, 99%, 99.5% or 99.9% identical to SEQ ID NO:5. Most preferably, the bacterial strain in the composition is the *Blautia hydrogenotrophica* strain deposited under accession number DSM 10507/14294.

In further embodiments of the invention, the bacterial strain in the composition is of *Blautia stercoris*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Blautia stercoris*. Preferably, the bacterial strain has a 16s rRNA sequence that is at least 95%, 96%, 97%, 98%, 99%, 99.5% or 99.9% identical to SEQ ID NO:1 or 3. Preferably, the sequence identity is to SEQ ID NO:3. Preferably, the bacterial strain for use in the invention has the 16s rRNA sequence represented by SEQ ID NO:3.

In further embodiments of the invention, the bacterial strain in the composition is of *Blautia wexlerae*. Closely related strains may also be used, such as bacterial strains that have a 16s rRNA sequence that is at least 95%, 96%, 97%, 98%, 99%, 99.5% or 99.9% identical to the 16s rRNA sequence of a bacterial strain of *Blautia wexlerae*. Preferably, the bacterial strain has a 16s rRNA sequence that is at least 95%, 96%, 97%, 98%, 99%, 99.5% or 99.9% identical to SEQ ID NO:2 or 4. Preferably, the sequence identity is to SEQ ID NO:4. Preferably, the bacterial strain for use in the invention has the 16s rRNA sequence represented by SEQ ID NO:4.

In certain embodiments, the composition of the invention is for oral administration. Oral administration of the strains of the invention can be effective for treating visceral hypersensitivity. Also, oral administration is convenient for patients and practitioners and allows delivery to and/or partial or total colonisation of the intestine.

In certain embodiments, the composition of the invention comprises one or more pharmaceutically acceptable excipients or carriers.

In certain embodiments, the composition of the invention comprises a bacterial strain that has been lyophilised. Lyophilisation is an effective and convenient technique for preparing stable compositions that allow delivery of bacteria, and is shown to provide effective compositions in the examples.

In certain embodiments, the invention provides a food product comprising the composition as described above.

In certain embodiments, the invention provides a vaccine composition comprising the composition as described above.

Additionally, the invention provides a method of treating or preventing visceral hypersensitivity, comprising administering a composition comprising a bacterial strain of the genus *Blautia*.

BRIEF DESCRIPTION OF DRAWINGS

FIG. 9A illustrates a scatter plot of the rat $H_2S$ MIH IBS+BH data. FIG. 9B illustrates a bar graph of the rat $H_2S$ MIH IBS+BH data.

FIG. 10A illustrates a scatter plot of the rat MIH IBS+BH data. FIG. 10B illustrates a bar graph of the rat sulphide levels for the MIH IBS+BH data.

FIG. 23A shows concentration of total SCFA. FIG. 23B shows concentration of Acetic acid, Propionic acid and Butyric acid.

DISCLOSURE OF THE INVENTION

Bacterial Strains

Figure 1:
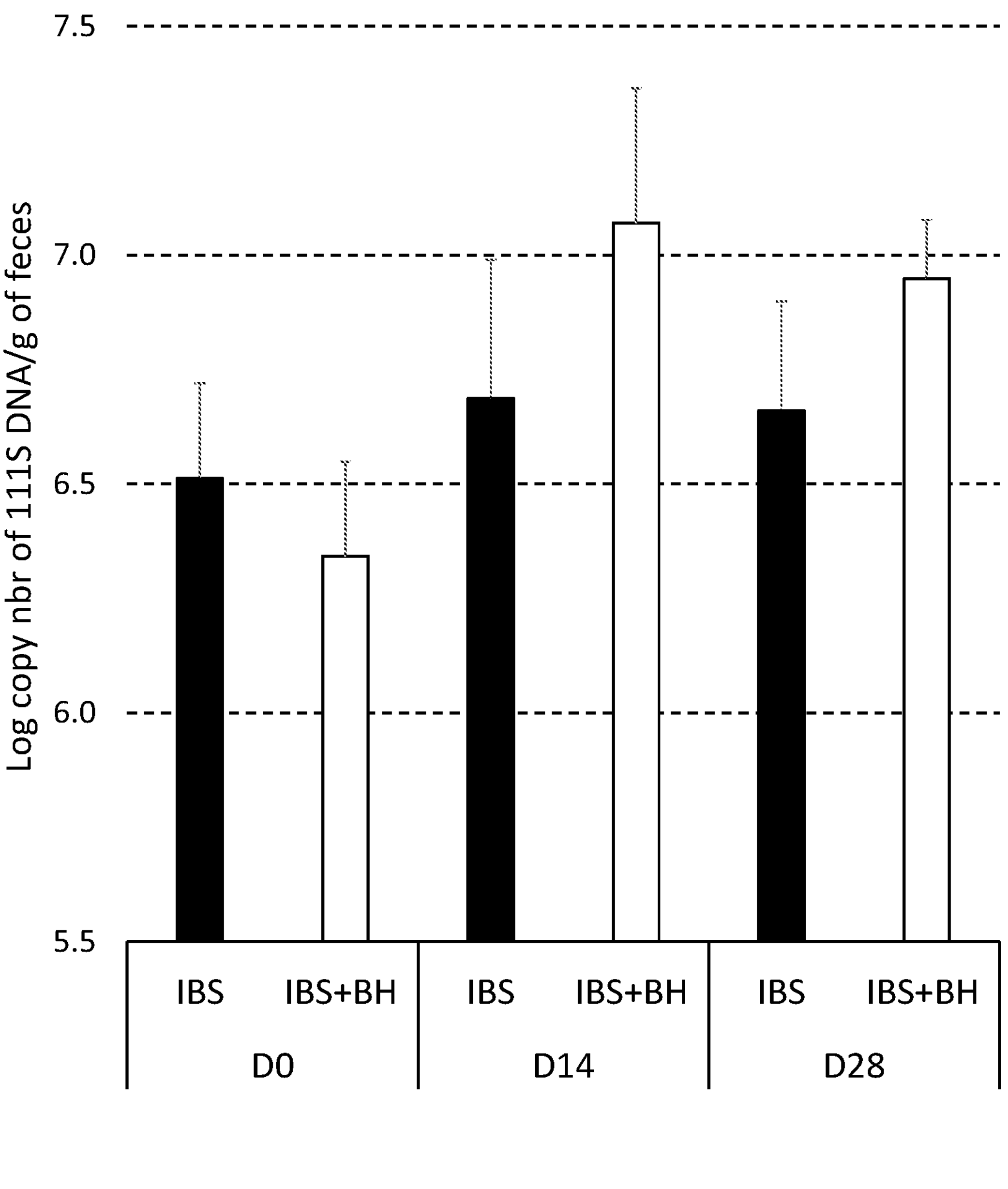
FIG. 1: Measurement of BH population by qPCR, showing an increase in BH at days 14 and 28 for animals receiving the BH lyophilisate.

The compositions of the invention comprise a bacterial strain of the genus *Blautia*. The examples demonstrate that bacteria of this genus are useful for treating or preventing visceral hypersensitivity. The preferred bacterial strains are of the species *Blautia hydrogenotrophica, Blautia stercoris* and *Blautia wexlerae*. Other preferred bacterial strains for use in the invention are *Blautia producta, Blautia coccoides* and *Blautia hansenii*.

Examples of *Blautia* strains for use in the invention include *Blautia hydrogenotrophica, B. stercoris, B. faecis, B. coccoides, B. glucerasea, B. hansenii, B. luti, B. producta,*

*B. schinkii* and *B. wexlerae*. The *Blautia* species are Gram-reaction-positive, non-motile bacteria that may be either coccoid or oval and all are obligate anaerobes that produce acetic acid as the major end product of glucose fermentation [17]. *Blautia* may be isolated from the human gut, although *B. producta* was isolated from a septicaemia sample.

*Blautia hydrogenotrophica* (previously known as *Ruminococcus hydrogenotrophicus*) has been isolated from the guts of mammals, is strictly anaerobic, and metabolises $H_2/CO_2$ to acetate, which may be important for human nutrition and health. The type strain of *Blautia hydrogenotrophica* is S5a33=DSM 10507=JCM 14656. The GenBank accession number for the 16S rRNA gene sequence of *Blautia hydrogenotrophica* strain S5a36 is X95624.1 (disclosed herein as SEQ ID NO:5). This exemplary *Blautia hydrogenotrophica* strain is described in [17] and [18]. The S5a33 strain and the S5a36 strain correspond to two subclones of a strain isolated from a faecal sample of a healthy subject. They show identical morphology, physiology and metabolism and have identical 16S rRNA sequences. Thus, in some embodiments, the *Blautia hydrogenotrophica* for use in the invention has the 16S rRNA sequence of SEQ ID NO:5.

All deposits were made under the terms of the Budapest Treaty. Maintenance of a viable culture is assured for 30 years from the date of the deposit. All restrictions on the availability to the public of the deposited microorganisms will be irrevocably removed upon the granting of a patent for this application.

The *Blautia hydrogenotrophica* bacterium deposited under accession number DSM 10507 and also under accession number DSM 14294 was tested in the Examples and is also referred to herein as strain BH. Strain BH was deposited with the Deutsche Sammlung von Mikroorganismen [German Microorganism Collection] (Mascheroder Weg 1b, 38124 Braunschweig, Germany) in January 1996 as "*Ruminococcus hydrogenotrophicus*" under accession number DSM 10507 and also under accession number DSM 14294 as "S5a33" on 10 May 2001. The depositor was INRA Laboratoire de Microbiologie CR de Clermont-Ferrand/Theix 63122 Saint Genes Champanelle, France. Ownership of the deposits has passed to 4D Pharma Plc by way of assignment.

The GenBank accession number for the 16S rRNA gene sequence of *Blautia stercoris* strain GAM6-$1^T$ is HM626177 (disclosed herein as SEQ ID NO:1). An exemplary *Blautia stercoris* strain is described in [19]. The type strain of *Blautia wexlerae* is WAL 14507=ATCC BAA-1564=DSM 19850 [17]. The GenBank accession number for the 16S rRNA gene sequence of *Blautia wexlerae* strain WAL 14507 T is EF036467 (disclosed herein as SEQ ID NO:2). This exemplary *Blautia wexlerae* strain is described in [17].

A preferred *Blautia stercoris* strain is the strain deposited under accession number NCIMB 42381, which is also referred to herein as strain 830. A 16S rRNA sequence for the 830 strain is provided in SEQ ID NO:3. Strain 830 was deposited with the international depositary authority NCIMB, Ltd. (Ferguson Building, Aberdeen, AB21 9YA, Scotland) by GT Biologics Ltd. (Life Sciences Innovation Building, Aberdeen, AB25 2ZS, Scotland) on 12 Mar. 2015 as "*Blautia stercoris* 830" and was assigned accession number NCIMB 42381. GT Biologics Ltd. subsequently changed its name to 4D Pharma Research Limited.

A preferred *Blautia wexlerae* strain is the strain deposited under accession number NCIMB 42486, which is also referred to herein as strain MRX008. A 16S rRNA sequence for the MRX008 strain is provided in SEQ ID NO:4. Strain MRX008 was deposited with the international depositary authority NCIMB, Ltd. (Ferguson Building, Aberdeen, AB21 9YA, Scotland) by 4D Pharma Research Ltd. (Life Sciences Innovation Building, Aberdeen, AB25 2ZS, Scotland) on 16 Nov. 2015 as "*Blaqutia/Ruminococcus* MRx0008" and was assigned accession number NCIMB 42486.

Bacterial strains closely related to the strain tested in the examples are also expected to be effective for treating or preventing visceral hypersensitivity. In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Blautia hydrogenotrophica*. Preferably, the bacterial strain for use in the invention has a 16s rRNA sequence that is at least 95%, 96%, 97%, 98%, 99%, 99.5% or 99.9% identical to SEQ ID NO:5.

In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Blautia stercoris*. Preferably, the bacterial strain for use in the invention has a 16s rRNA sequence that is at least 95%, 96%, 97%, 98%, 99%, 99.5% or 99.9% identical to SEQ ID NO:1 or SEQ ID NO:3. Preferably, the sequence identity is to SEQ ID NO:3. Preferably, the bacterial strain for use in the invention has the 16s rRNA sequence represented by SEQ ID NO:3. In certain embodiments, the bacterial strain for use in the invention has a 16s rRNA sequence that is at least 95%, 96%, 97%, 98%, 99%, 99.5% or 99.9% identical to the 16s rRNA sequence of a bacterial strain of *Blautia wexlerae*. Preferably, the bacterial strain for use in the invention has a 16s rRNA sequence that is at least 95%, 96%, 97%, 98%, 99%, 99.5% or 99.9% identical to SEQ ID NO:2 or SEQ ID NO:4. Preferably, the sequence identity is to SEQ ID NO:4. Preferably, the bacterial strain for use in the invention has the 16s rRNA sequence represented by SEQ ID NO:4.

Bacterial strains that are biotypes of the bacterium deposited under accession number DSM 10507/14294 or biotypes of the bacteria deposited under accession numbers NCIMB 42381 and NCIMB 42486 are also expected to be effective for treating or preventing visceral hypersensitivity. A biotype is a closely related strain that has the same or very similar physiological and biochemical characteristics.

Strains that are biotypes of a bacterium deposited under accession number DSM 10507/14294, NCIMB 42381 or NCIMB 42486 and that are suitable for use in the invention may be identified by sequencing other nucleotide sequences for a bacterium deposited under accession number DSM 10507/14294, NCIMB 42381 or NCIMB 42486. For example, substantially the whole genome may be sequenced and a biotype strain for use in the invention may have at least 95%, 96%, 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, $(GTG)_5$, or REP or [20]. Biotype strains may have sequences with at least 95%, 96%, 97%, 98%, 99%, 99.5% or 99.9% sequence identity to the corresponding sequence of a bacterium deposited under accession number DSM 10507/14294, NCIMB 42381 or NCIMB 42486. In some embodiments, a biotype strain has a sequence with at least 97%, 98%, 99%, 99.5% or 99.9% sequence identity to the corresponding sequence of the *Blautia hydrogenotrophica* strain deposited as DSM 10507/14294 and comprises a 16S rRNA sequence that is at least 99% identical (e.g. at least 99.5% or at least 99.9% identical) to SEQ ID NO:5. In some embodiments, a biotype strain has a sequence with at least 97%, 98%, 99%, 99.5% or 99.9% sequence identity to the corresponding sequence of the *Blautia hydrogenotrophica* strain deposited as DSM 10507/14294 and has the 16S rRNA sequence of SEQ ID NO:5.

Alternatively, strains that are biotypes of a bacterium deposited under accession number DSM 10507/14294, NCIMB 42381 or NCIMB 42486 and that are suitable for use in the invention may be identified by using the accession number DSM 10507/14294 deposit, the accession number NCIMB 42381 deposit, or the accession number NCIMB 42486 deposit, and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing. In preferred embodiments, such techniques may be used to identify other *Blautia hydrogenotrophica, Blautia stercoris* or *Blautia wexlerae* strains.

In certain embodiments, strains that are biotypes of a bacterium deposited under accession number DSM 10507/14294, NCIMB 42381 or NCIMB 42486 and that are suitable for use in the invention are strains that provide the same pattern as a bacterium deposited under accession number DSM 10507/14294, NCIMB 42381 or NCIMB 42486 when analysed by amplified ribosomal DNA restriction analysis (ARDRA), for example when using Sau3AI restriction enzyme (for exemplary methods and guidance see, for example, [21]). Alternatively, biotype strains are identified as strains that have the same carbohydrate fermentation patterns as a bacterium deposited under accession number DSM 10507/14294, NCIMB 42381 or NCIMB 42486.

Other *Blautia* strains that are useful in the compositions and methods of the invention, such as biotypes of a bacterium deposited under accession number DSM 10507/14294, NCIMB 42381 or NCIMB 42486, may be identified using any appropriate method or strategy, including the assays described in the examples. For instance, strains for use in the invention may be identified by culturing bacteria and administering to rats to test in the distension assay. In particular, bacterial strains that have similar growth patterns, metabolic type and/or surface antigens to a bacterium deposited under accession number DSM 10507/14294, NCIMB 42381 or NCIMB 42486 may be useful in the invention. A useful strain will have comparable microbiota modulatory activity to the DSM 10507/14294, NCIMB 42381 or NCIMB 42486 strain. In particular, a biotype strain will elicit comparable effects on the visceral hypersensitivity model to the effects shown in the Examples, which may be identified by using the culturing and administration protocols described in the Examples.

A particularly preferred strain of the invention is the *Blautia hydrogenotrophica* strain deposited under accession number DSM 10507/14294. This is the exemplary BH strain tested in the examples and shown to be effective for treating disease. Therefore, the invention provides a cell, such as an isolated cell, of the *Blautia hydrogenotrophica* strain deposited under accession number DSM 10507/14294, or a derivative thereof, for use in therapy, in particular for the diseases described herein.

A derivative of the strain deposited under accession number DSM 10507/14294, NCIMB 42381 or NCIMB 42486 may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable microbiota modulatory activity to the original DSM 10507/14294, NCIMB 42381 or NCIMB 42486 strain. In particular, a derivative strain will elicit comparable effects on the visceral hypersensitivity model to the effects shown in the Examples, which may be identified by using the culturing and administration protocols described in the Examples. A derivative of the DSM 10507/14294 strain will generally be a biotype of the DSM 10507/14294 strain. A derivative of the NCIMB 42381 strain will generally be a biotype of the NCIMB 42381 strain. A derivative of the NCIMB 42486 strain will generally be a biotype of the NCIMB 42486 strain.

References to cells of the *Blautia hydrogenotrophica* strain deposited under accession number DSM 10507/14294 encompass any cells that have the same safety and therapeutic efficacy characteristics as the strains deposited under accession number DSM 10507/14294, and such cells are encompassed by the invention. References to cells of the *Blautia stercoris* strain deposited under accession number NCIMB 42381 encompass any cells that have the same safety and therapeutic efficacy characteristics as the strains deposited under accession number NCIMB 42381, and such cells are encompassed by the invention. References to cells of the *Blautia wexlerae* strain deposited under accession number NCIMB 42486 encompass any cells that have the same safety and therapeutic efficacy characteristics as the strains deposited under accession number NCIMB 42486, and such cells are encompassed by the invention.

In preferred embodiments, the bacterial strains in the compositions of the invention are viable and capable of partially or totally colonising the intestine.

Therapeutic Uses

In preferred embodiments, the compositions of the invention are for use in treating visceral hypersensitivity. Visceral hypersensitivity is a specific type of pain characterized by a subjectively painful perception located in the abdominal area resulting from activation of nociceptors of the thoracic, pelvic, or abdominal viscera (organs). Visceral hypersensitivity is generally diffuse and difficult to localise, and therefore contrasts with somatic pain, which is generally sharper and more localised. Also, visceral hypersensitivity generally is not associated with specific structural lesions, unlike somatic pain. Visceral nociceptors are intrinsically different from cutaneous and most other non-visceral nociceptors [22].

Visceral hypersensitivity is generally experienced in the abdomen, but not all abdominal pain is visceral hypersensitivity. In contrast, there are many potential causes of abdominal pain and abdominal pain may be somatic, referred or visceral pain. In the abdomen, somatic pain may be caused by an inflamed organ and is generally sharp and localised. Abdominal pain may be caused by fibromyalgia, which is a condition of somatic (skin and muscle) hypersensitivity. Referred pain is felt in a cutaneous site distant from the diseased organ.

Visceral hypersensitivity is often associated with functional dyspepsia and irritable bowel syndrome (IBS). However, not all pain associated with functional dyspepsia and IBS is visceral hypersensitivity. Indeed, many patients with IBS also exhibit a wide variety of somatic symptoms in abdominal regions (back pain, heartburn) and non-abdominal regions (migraine headaches, dyspareunia, muscle pain in body regions somatotopically distinct from the gut) [23].

In some embodiments, the pathogenesis of the disease or condition affects the intestine. In some embodiments, the pathogenesis of the disease or condition does not affect the intestine. In some embodiments, the pathogenesis of the disease or condition is not localised at the intestine. In some embodiments, the treating or preventing occurs at a site other than at the intestine. In some embodiments, the treating or preventing occurs at the intestine and also at a site other than at the intestine. In certain embodiments, the disease or condition is systemic.

Visceral hypersensitivity is also known as visceral pain, and these two terms are used interchangeably herein.

As demonstrated in the examples, bacterial compositions of the invention may be effective for reducing visceral hypersensitivity. In particular, bacterial compositions of the invention can reduce the response to colorectal distension, which is a manifestation of visceral hypersensitivity that affects many patients. In preferred embodiments, the compositions of the invention are for use in treating or preventing visceral hypersensitivity in the abdomen, preferably in the gastrointestinal tract, and most preferably in the lower gastrointestinal tract. In further embodiments, the compositions of the invention are for use in treating or preventing visceral hypersensitivity in the caecum, colon or rectum.

In preferred embodiments, the compositions of the invention are for use in treating or preventing visceral hypersensitivity associated with Crohn's disease, ulcerative colitis, functional dyspepsia, infantile colic or, more preferably, IBS. In preferred embodiments, the compositions of the invention are for use in treating or preventing visceral hypersensitivity in a subject diagnosed with Crohn's disease, ulcerative colitis, functional dyspepsia, infantile colic, or, more preferably, IBS. In preferred embodiments the compositions of the invention are for use in treating or preventing visceral hypersensitivity in the treatment of Crohn's disease, ulcerative colitis, functional dyspepsia, infantile colic, or, more preferably, IBS.

In preferred embodiments, the compositions of the invention are for use in treating or preventing visceral hypersensitivity associated with Crohn's disease, ulcerative colitis, functional dyspepsia or, more preferably, IBS. In preferred embodiments, the compositions of the invention are for use in treating or preventing visceral hypersensitivity in a subject diagnosed with Crohn's disease, ulcerative colitis, functional dyspepsia or, more preferably, IBS. In preferred embodiments the compositions of the invention are for use in treating or preventing visceral hypersensitivity in the treatment of Crohn's disease, ulcerative colitis, functional dyspepsia or, more preferably, IBS. In certain embodiments, the compositions of the invention are for use in treating visceral hypersensitivity in a patient suffering from painful distension of the gastrointestinal tract, in particular in the colon or rectum.

Certain aspects of the discomfort and suffering associated with IBS and other bowel conditions may be caused by the excess production of gases in the gastrointestinal tract and the bulk volume of these accumulated gases. The increased volume of different gases may result in flatulence, for example. As shown in the examples, the bacterial compositions of the invention may be effective for treating a specific aspect of IBS and other bowel conditions—visceral hypersensitivity. Without wishing to be bound by any theory, the observed effect of the bacterial compositions of the invention on visceral hypersensitivity may be associated with an effect of the bacteria on a specific gas —$H_2S$, and an effect on sulphate reducing bacteria (SRB), which synthesise $H_2S$ in the gut. $H_2S$ may have important roles as a pain signalling molecule and the effect of the compositions of the invention on visceral hypersensitivity observed in the examples may be related to a reduction in the production of $H_2S$ in the bowel, which may contribute to visceral hypersensitivity by affecting pain signalling, independently from any bloating effects related to gas volume. The examples demonstrate that the bacterial compositions of the invention can be effective for reducing SRB and reducing $H_2S$. In some embodiments, the bacterial compositions of the invention reduce SRB and/or reduce $H_2S$ in the caecum. SRB are anaerobic bacteria that use sulphate reduction for the generation of energy and examples of SRB include members of the genus *Desulfovibrio*, and in particular *Desulfovibrio piger*, which is the most abundant species, and also the genera *Desulfobacter, Desulfobulbus* and *Desulfotomaculum.*

In certain embodiments, the compositions of the invention are for use in reducing colonisation of the gastrointestinal tract by SRB in the treatment of visceral hypersensitivity. In such embodiments, the composition may preferably be in the form of a bacterial culture. In such embodiments, the composition may preferably be a lyophilisate. In certain embodiments, the compositions of the invention are for use in lowering $H_2S$ levels or preventing elevated $H_2S$ levels in the gastrointestinal tract in the treatment of visceral hypersensitivity. In such embodiments, the composition may preferably be a lyophilisate.

In certain embodiments, the compositions of the invention are for use in reducing colonisation, community and/or population levels of the gastrointestinal tract by SRB in the treatment of visceral hypersensitivity. In certain embodiments, the compositions of the invention are for use in reducing colonisation, community and/or population levels of the caecum by SRB in the treatment of visceral hypersensitivity.

In preferred embodiments, the compositions of the invention are for use in reducing colonisation of the gastrointestinal tract by SRB, lowering $H_2S$ levels, or preventing elevated $H_2S$ levels in the treatment of visceral hypersensitivity associated with IBS. In further embodiments, the compositions of the invention are for use in reducing colonisation of the gastrointestinal tract by SRB, lowering $H_2S$ levels, or preventing elevated $H_2S$ levels in the treatment of visceral hypersensitivity associated with Crohn's Disease, ulcerative colitis, functional dyspepsia or infantile colic, for example in the treatment of visceral hypersensitivity associated with Crohn's Disease, ulcerative colitis or functional dyspepsia.

In preferred embodiments, the compositions of the invention are for use in reducing colonisation, community and/or population levels of the gastrointestinal tract by SRB, lowering $H_2S$ levels, or preventing elevated $H_2S$ levels in the treatment of visceral hypersensitivity associated with IBS. In further embodiments, the compositions of the invention are for use in reducing colonisation, community and/or population levels of the gastrointestinal tract by SRB, lowering $H_2S$ levels, or preventing elevated $H_2S$ levels in the treatment of visceral hypersensitivity associated with Crohn's Disease, ulcerative colitis, functional dyspepsia or infantile colic, for example, in the treatment of visceral hypersensitivity associated with Crohn's Disease, ulcerative colitis or functional dyspepsia.

In preferred embodiments, the compositions of the invention are for use in reducing colonisation of the gastrointestinal tract by SRB, lowering $H_2S$ levels, or preventing elevated $H_2S$ levels in the treatment of visceral hypersensitivity in the abdomen, preferably in the gastrointestinal tract, more preferably in the lower gastrointestinal tract, in the caecum, in the colon or in the rectum. In preferred embodiments, the compositions of the invention are for use in reducing colonisation, community and/or population levels of the gastrointestinal tract by SRB, lowering $H_2S$ levels, or preventing elevated $H_2S$ levels in the treatment of visceral hypersensitivity in the abdomen, preferably in the gastrointestinal tract, more preferably in the lower gastrointestinal tract, in the caecum, in the colon or in the rectum.

In certain embodiments, the compositions of the invention are for use in a method of treating, preventing or reducing colonisation of the gastrointestinal tract by SRB. In certain embodiments, the compositions of the invention are for use in a method of treating, preventing or reducing colonisation, community and/or population levels of the gastrointestinal tract by SRB. In certain embodiments, the compositions of the invention are for use in a method of lowering $H_2S$ levels or preventing elevated $H_2S$ levels in the gastrointestinal tract.

In certain embodiments, the compositions of the invention are for use in treating patients that exhibit, or are expected to exhibit, increased levels of SRB and/or $H_2S$ in their gastrointestinal tract, for example, when compared to a healthy subject, or a population of healthy subjects.

In certain embodiments, the compositions of the invention are for use in preventing visceral hypersensitivity in a subject that is receiving or has received antibiotic treatment or that is suffering from or has suffered from bacterial gastroenteritis. Antibiotic treatment and bacterial gastroenteritis are associated with changes in the gut microbiota that may precede visceral hypersensitivity and that may be prevented by the compositions of the invention. The compositions of the invention may be administered concurrently with an antibiotic treatment.

In preferred embodiments, treatment with compositions of the invention results in a reduction in visceral hypersensitivity, a reduction in colonisation by SRB, and/or a reduction in $H_2S$ levels.

Treatment or prevention of visceral hypersensitivity may refer to, for example, an alleviation of the severity of symptoms or a reduction in the frequency of exacerbations or the range of triggers that are a problem for the patient. For example, in some embodiments the composition of the invention is for use in treating or preventing severe visceral hypersensitivity. In some embodiments the subject having severe visceral hypersensitivity is a subject diagnosed with Crohn's disease, ulcerative colitis, functional dyspepsia, infantile colic, or, more preferably, IBS. In some embodiments the subject having severe visceral hypersensitivity is a subject diagnosed with Crohn's disease, ulcerative colitis, functional dyspepsia or, more preferably, IBS.

Modes of Administration

Preferably, the compositions of the invention are to be administered to the gastrointestinal tract in order to enable delivery to and/or partial or total colonisation of the intestine with the bacterial strain of the invention. Generally, the compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a theobroma oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily. The examples demonstrate that daily administration provides successfully colonisation and clinical benefits in the rat model of visceral hypersensitivity.

The examples also demonstrate that BH administration may not result in permanent colonisation of the intestines, so regular administration for extended periods of time may provide greater therapeutic benefits. Thus, the examples show successful delivery of the bacterial strain of the invention to the colon following daily administration.

Accordingly, in certain embodiments, the compositions of the invention are administered regularly, such as daily, every two days, or weekly, for an extended period of time, such as for at least one week, two weeks, one month, two months, six months, or one year.

In some embodiments the compositions of the invention are administered for 7 days, 14 days, 16 days, 21 days or 28 days or no more than 7 days, 14 days, 16 days, 21 days or 28 days. For example, in some embodiments the compositions of the invention are administered for 16 days.

In certain embodiments of the invention, treatment according to the invention is accompanied by assessment of the patient's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to prevent visceral hypersensitivity developing in her child in utero and/or after it is born.

The compositions of the invention may be administered to a patient that has been diagnosed with visceral hypersensitivity or a disease or condition associated with visceral hypersensitivity, or that has been identified as being at risk of visceral hypersensitivity. The compositions may also be administered as a prophylactic measure to prevent the development of visceral hypersensitivity in a healthy patient.

The compositions of the invention may be administered to a patient that has been identified as having an abnormal gut microbiota. For example, the patient may have reduced or absent colonisation by *Blautia*, and in particular *Blautia hydrogenotrophica, Blautia stercoris* or *Blautia wexlerae.*

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

In some embodiments, the subject to whom the composition is to be administered is an adult human. In some embodiments, the subject to whom the composition is to be administered is an infant human.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilised bacteria. Lyophilisation of bacteria is a well-established procedure and relevant guidance is available in, for example, references [24-26]. The examples demonstrate that lyophilisate compositions are particularly effective. In preferred embodiments, the compositions of the invention comprises lyophilised bacteria and is for the treatment of visceral hypersensitivity associated with IBS, preferably for the lowering $H_2S$ levels or preventing elevated $H_2S$ levels in the treatment of visceral hypersensitivity associated with IBS. In further preferred embodiments, the compositions of the invention comprises lyophilised bacteria and is for the treatment of visceral hypersensitivity associated with IBS, preferably for use in reducing colonisation of the gastrointestinal tract by SRB in the treatment of visceral hypersensitivity. In further preferred embodiments, the composition of the invention comprises lyophilised bacteria and is for the treatment of visceral hypersensitivity associated with IBS, preferably for use in reducing colonisation, community and/or population levels of the gastrointestinal tract by SRB in the treatment of visceral hypersensitivity.

Alternatively, the composition of the invention may comprise a live, active bacterial culture. The examples demonstrate that cultures of the bacteria of the invention are therapeutically effective.

In some embodiments, the bacterial strain in the composition of the invention has not been inactivated, for example, has not been heat-inactivated. In some embodiments, the bacterial strain in the composition of the invention has not been killed, for example, has not been heat-killed. In some embodiments, the bacterial strain in the composition of the invention has not been attenuated, for example, has not been heat-attenuated. For example, in some embodiments, the bacterial strain in the composition of the invention has not been killed, inactivated and/or attenuated. For example, in some embodiments, the bacterial strain in the composition of the invention is live. For example, in some embodiments, the bacterial strain in the composition of the invention is viable. For example, in some embodiments, the bacterial strain in the composition of the invention is capable of partially or totally colonising the intestine. For example, in some embodiments, the bacterial strain in the composition of the invention is viable and capable of partially or totally colonising the intestine.

In some embodiments, the composition comprises a mixture of live bacterial strains and bacterial strains that have been killed.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [27-28].

The composition may be administered orally and may be in the form of a tablet, capsule or powder. Encapsulated products are preferred because *Blautia* are anaerobes. Other ingredients (such as vitamin C, for example), may be included as oxygen scavengers and prebiotic substrates to improve the delivery and/or partial or total colonisation and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention. A therapeutically effective amount of a bacterial strain is sufficient to exert a beneficial effect upon a patient. A therapeutically effective amount of a bacterial strain may be sufficient to result in delivery to and/or partial or total colonisation of the patient's intestine.

A suitable daily dose of the bacteria, for example for an adult human, may be from about $1\times10^3$ to about $1\times10^{11}$ colony forming units (CFU); for example, from about $1\times10^7$ to about $1\times10^{10}$ CFU; in another example from about $1\times10^6$ to about $1\times10^{10}$ CFU; in another example from about $1\times10^7$ to about $1\times10^{11}$ CFU; in another example from about $1\times10^8$ to about $1\times10^{10}$ CFU; in another example from about $1\times10^8$ to about $1\times10^{11}$ CFU.

In certain embodiments, the dose of the bacteria is at least $10^9$ cells per day, such as at least $10^{10}$, at least $10^{11}$, or at least $10^{12}$ cells per day.

In certain embodiments, the composition contains the bacterial strain in an amount of from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [29].

Acceptable carriers or diluents for therapeutic use are well known in the pharmaceutical art and are described, for example, in reference [30]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid, cysteine and esters of p-hydroxybenzoic acid, for example, in some embodiments the preservative is selected from sodium benzoate, sorbic acid and esters of p-hydroxybenzoic acid. Antioxidants and suspending agents may be also used. A further example of a suitable carrier is saccharose. A further example of a preservative is cysteine.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

In some embodiments, the compositions of the invention comprise one or more bacterial strains of the genus *Blautia* and do not contain bacteria from any other genus, or which comprise only de minimis or biologically irrelevant amounts of bacteria from another genus.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture that is substantially free from other species of organism. In some embodiments, such compositions may be a lyophilisate that is substantially free from other species of organism.

In certain embodiments, the compositions of the invention comprise one or more bacterial strains of the genus *Blautia*, for example, a *Blautia hydrogenotrophica*, and do not contain any other bacterial genus, or which comprise only de minimis or biologically irrelevant amounts of bacteria from another genus. In certain embodiments, the compositions of the invention comprise a single species of *Blautia*, for example, a *Blautia hydrogenotrophica*, and do not contain any other bacterial species, or which comprise only de minimis or biologically irrelevant amounts of bacteria from another species. In certain embodiments, the compositions of the invention comprise a single strain of *Blautia*, for example, of *Blautia hydrogenotrophica*, and do not contain any other bacterial strains or species, or which comprise only de minimis or biologically irrelevant amounts of bacteria from another strain or species.

In some embodiments, the compositions of the invention comprise more than one bacterial strain or species. For example, in some embodiments, the compositions of the invention comprise more than one strain from within the same species (e.g. more than 1, 2, 3, 4, 5, 6, 7, 8, 9, 10, 15, 20, 25, 30, 35, 40 or 45 strains), and, optionally, do not contain bacteria from any other species. In some embodiments, the compositions of the invention comprise less than 50 strains from within the same species (e.g. less than 45, 40, 35, 30, 25, 20, 15, 12, 10, 9, 8, 7, 6, 5, 4 or 3 strains), and, optionally, do not contain bacteria from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 strains from within the same species and, optionally, do not contain bacteria from any other species. In some embodiments, the compositions of the invention comprise more than one species from within the same genus (e.g. more than 1, 2, 3, 4, 5, 6, 7, 8, 9, 10, 12, 15, 17, 20, 23, 25, 30, 35 or 40 species), and, optionally, do not contain bacteria from any other genus. In some embodiments, the compositions of the invention comprise less than 50 species from within the same genus (e.g. less than 50, 45, 40, 35, 30, 25, 20, 15, 12, 10, 8, 7, 6, 5, 4 or 3 species), and, optionally, do not contain bacteria from any other genus. In some embodiments, the compositions of the invention comprise 1-50, 1-40, 1-30, 1-20, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 species from within the same genus and, optionally, do not contain bacteria from any other genus. The invention comprises any combination of the foregoing.

In some embodiments, the composition comprises a microbial consortium. For example, in some embodiments, the composition comprises the *Blautia* bacterial strain as part of a microbial consortium. For example, in some embodiments, the *Blautia* bacterial strain is present in combination with one or more (e.g. at least 2, 3, 4, 5, 10, 15 or 20) other bacterial strains from other genera with which it can live symbiotically in vivo in the intestine. For example, in some embodiments, the composition comprises a bacterial strain of *Blautia hydrogenotrophica* in combination with a bacterial strain from a different genus. In some embodiments, the microbial consortium comprises two or more bacterial strains obtained from a faeces sample of a single organism, e.g. a human. In some embodiments, the microbial consortium is not found together in nature. For example, in some embodiments, the microbial consortium comprises bacterial strains obtained from faeces samples of at least two different organisms. In some embodiments, the two different organisms are from the same species, e.g. two different humans. In some embodiments, the two different organisms are an infant human and an adult human. In some embodiments, the two different organisms are a human and a non-human mammal.

In some embodiments, the composition of the invention additionally comprises a bacterial strain that has the same safety and therapeutic efficacy characteristics as the *Blautia hydrogenotrophica* strain deposited under accession number DSM 10507/14294, but which is not the *Blautia hydrogenotrophica* strain deposited under accession number DSM 10507/14294, or which is not a *Blautia hydrogenotrophica* or which is not a *Blautia*.

In some embodiments in which the composition of the invention comprises more than one bacterial strain, species or genus, the individual bacterial strains, species or genera may be for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strains, species or genera are stored separately but are mixed together prior to use.

In some embodiments, the bacterial strain for use in the invention is obtained from human adult faeces. In some embodiments in which the composition of the invention comprises more than one bacterial strain, all of the bacterial strains are obtained from human adult faeces or if other bacterial strains are present they are present only in de minimis amounts. The bacteria may have been cultured subsequent to being obtained from the human adult faeces and being used in a composition of the invention.

In some embodiments, the one or more *Blautia* bacterial strains is/are the only therapeutically active agent(s) in a composition of the invention. In some embodiments, the bacterial strain(s) in the composition is/are the only therapeutically active agent(s) in a composition of the invention.

The compositions for use in accordance with the invention may or may not require marketing approval.

In certain embodiments, the invention provides the above pharmaceutical composition, wherein said bacterial strain is lyophilised. In certain embodiments, the invention provides the above pharmaceutical composition, wherein said bacterial strain is spray dried. In certain embodiments, the invention provides the above pharmaceutical composition, wherein the bacterial strain is lyophilised or spray dried and wherein it is live. In certain embodiments, the invention provides the above pharmaceutical composition, wherein the bacterial strain is lyophilised or spray dried and wherein it is viable. In certain embodiments, the invention provides the above pharmaceutical composition, wherein the bacterial strain is lyophilised or spray dried and wherein it is capable of partially or totally colonising the intestine. In certain embodiments, the invention provides the above pharmaceutical composition, wherein the bacterial strain is lyophilised or spray dried and wherein it is viable and capable of partially or totally colonising the intestine.

In some cases, the lyophilised or spray dried bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is visceral hypersensitivity, such as visceral hypersensitivity associated with Crohn's disease, ulcerative colitis, functional dyspepsia, infantile colic or, more preferably, IBS.

In certain embodiments, the invention provides a pharmaceutical composition comprising: a bacterial strain of the invention; and a pharmaceutically acceptable excipient, carrier or diluent; wherein the bacterial strain is in an amount sufficient to treat a disorder when administered to a subject in need thereof; and wherein the disorder is visceral hypersensitivity, such as visceral hypersensitivity associated with Crohn's disease, ulcerative colitis, functional dyspepsia or, more preferably, IBS.

In certain embodiments, the invention provides the above pharmaceutical composition, wherein the amount of the bacterial strain is from about $1\times10^3$ to about $1\times10^{11}$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4.0 or about 25.0 and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation.

For example, the composition may be provided as a tablet or capsule. In some embodiments, the capsule is a gelatine capsule ("gel-cap").

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [31]). In some embodiments, the formulation is an intrinsically enteric capsule (for example, Vcaps® from Capsugel).

In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

Culturing Methods

The bacterial strains for use in the present invention can be cultured using standard microbiology techniques as detailed in, for example, references [32-34].

The solid or liquid medium used for culture may for example be YCFA agar or YCFA medium. YCFA medium may include (per 100 ml, approximate values): Casitone (1.0 g), yeast extract (0.25 g), $NaHCO_3$ (0.4 g), cysteine (0.1 g), $K_2HPO_4$ (0.045 g), $KH_2PO_4$ (0.045 g), NaCl (0.09 g), $(NH_4)_2SO_4$ (0.09 g), $MgSO_4.7H_2O$ (0.009 g), $CaCl_2$) (0.009 g), resazurin (0.1 mg), hemin (1 mg), biotin (1 μg), cobalamin (1 μg), p-aminobenzoic acid (3 μg), folic acid (5 μg), and pyridoxamine (15 μg).

General

The practice of the present invention will employ, unless otherwise indicated, conventional methods of chemistry, biochemistry, molecular biology, immunology and pharmacology, within the skill of the art. Such techniques are explained fully in the literature. See, e.g., references [35-42], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref [43]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. [44].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

Example 1—Efficacy of Bacterial Inocula in a Rat Model of Visceral Hypersensitivity

Summary

Rats were inoculated with the faecal microbiota from a human IBS subject exhibiting visceral hypersensitivity. The rats were then administered with compositions comprising bacterial strains according to the invention and were then tested using a distension assay to measure visceral hypersensitivity. The compositions of the invention were found to reduce the rats' response to distension, indicating a reduction in visceral hypersensitivity.

Strain

*Blautia hydrogenotrophica* (BH) strain DSM 10507/14294.

Compositions and Administration

BH culture (16H) or lyophilisate—administered by oral gavage

Control solution administered by oral gavage

Rats

Inoculated with human intestinal microbiota from an IBS subject.

Study Design

Day −14—rats inoculated with human intestinal microbiota from an IBS subject

Days 0 to 28—daily dose of BH culture or lyophilisate, or control solution

Days 0, 14 and 28—qPCR of BH population in faecal samples

Between days 14 and 28—operation to implant electrode into the abdomen (for distension assay)

Day 28—distension assay, caecal samples collected for sulphides and short chain fatty acid (SCFA) analysis, enumeration of microbiota in faecal samples on selective media Results FIG. 1 presents the results of a qPCR analysis of the BH population in faecal samples from rats administered control solution (IBS) or BH lyophilisate (IBS+BH). An increase in the BH population was seen at days 14 and 28 in rats receiving the BH lyophilisate, which confirms successful colonisation.

Figure 2:
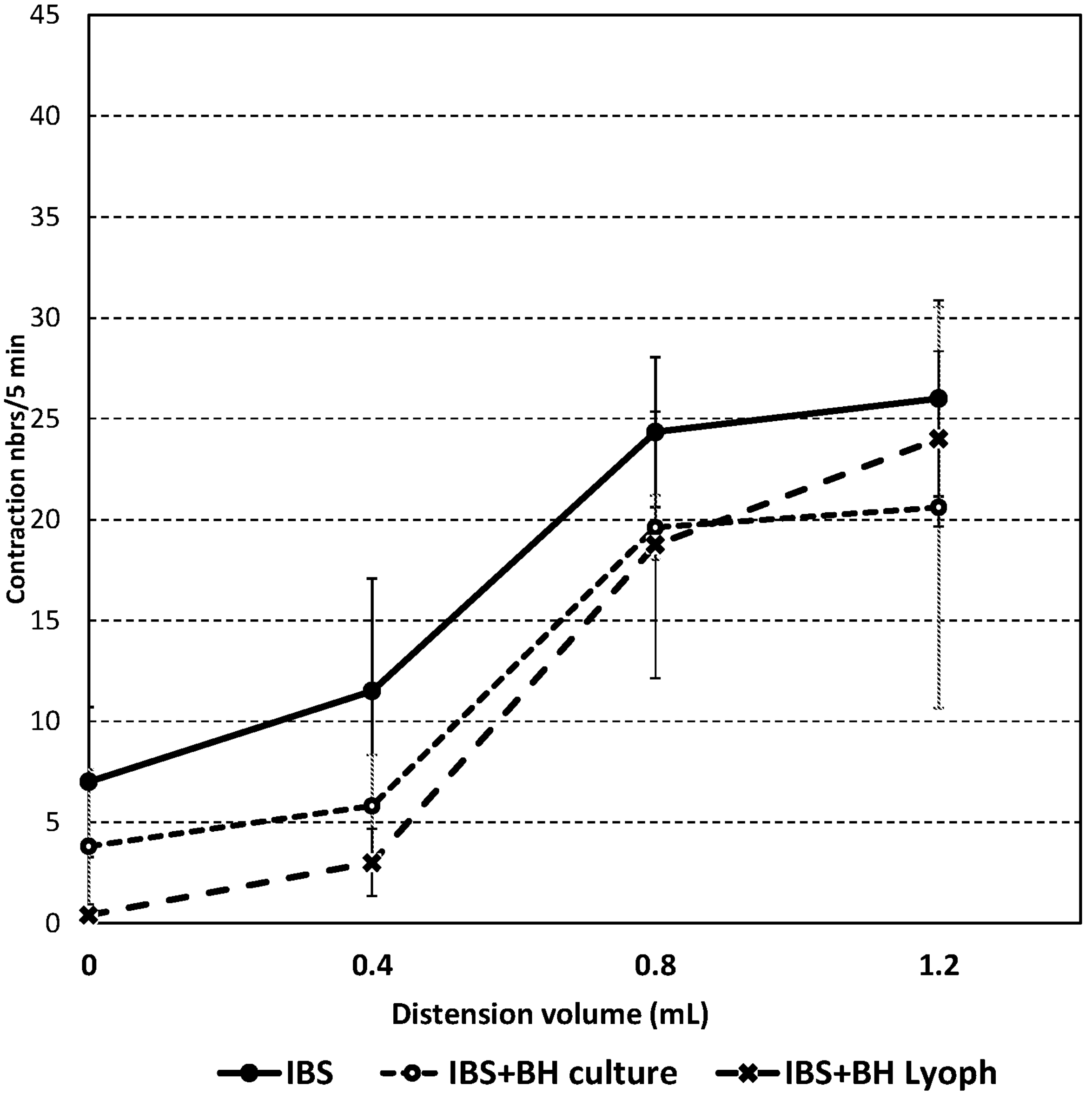
FIG. 2: Impact of BH culture and lypophilisate on animals' response to distension, showing a reduction in contractions for animals receiving BH compositions.

FIG. 2 presents the results of the distension assay. Rats were subjected to colorectal distension and the number of contractions per minute were recorded as a specific measure of visceral hypersensitivity. The rats treated with the compositions of the invention exhibited reduced contractions and reduced visceral hypersensitivity.

Figure 3:
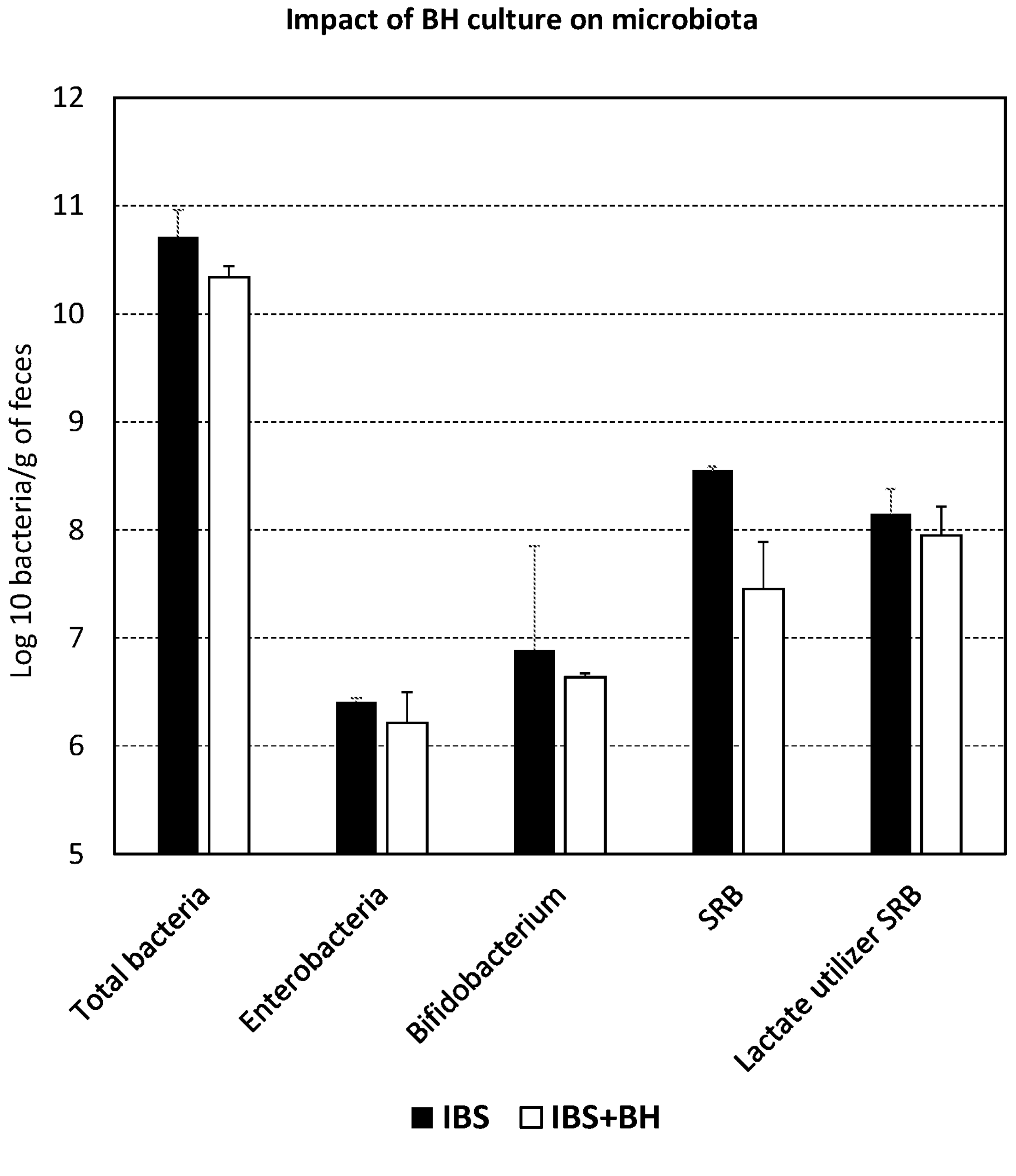
FIG. 3: Impact of BH culture on microbiota, showing a 1 log decrease in SRB in rats receiving a daily dose of BH culture.
Figure 4:
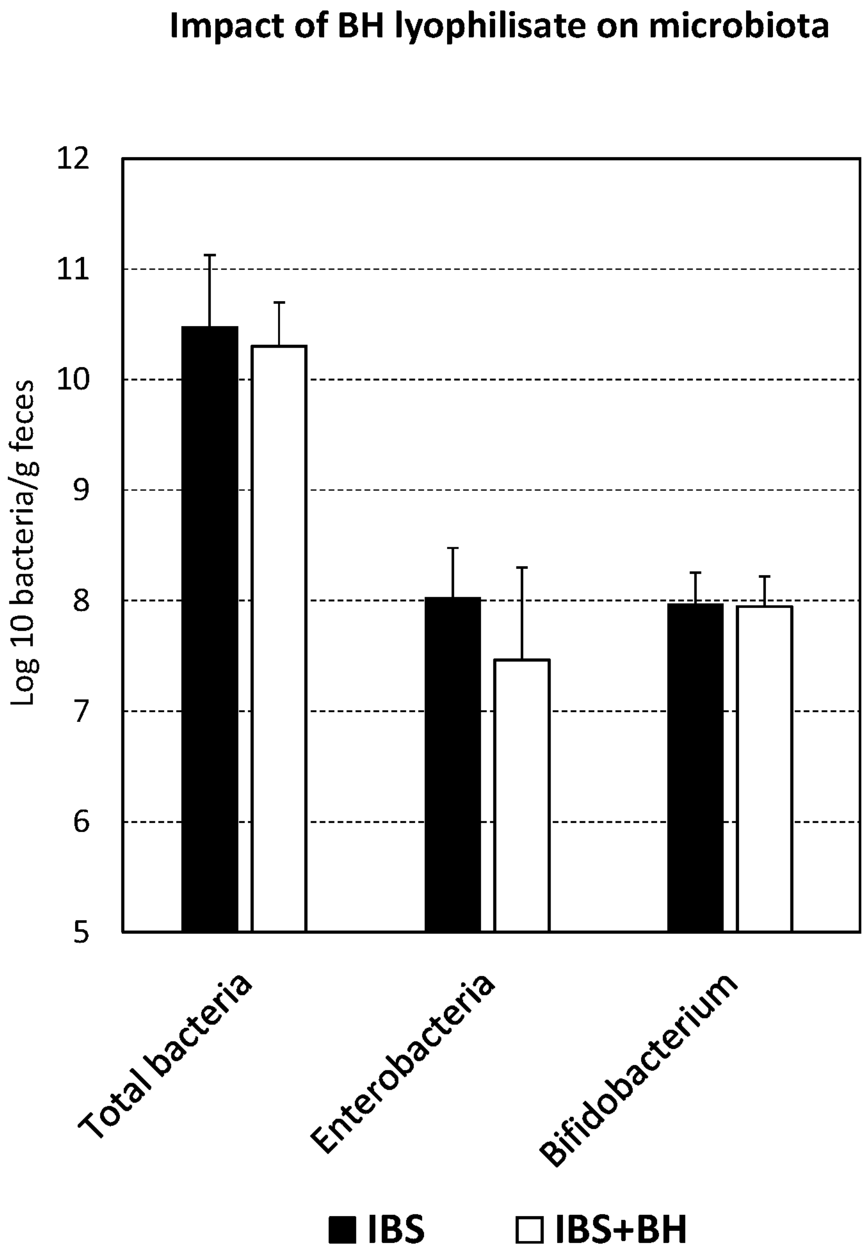
FIG. 4: Impact of BH lyophilisate on microbiota.

FIGS. 3 and 4 report on the effects of administration of BH culture and lyophilisate on the microbiota in faecal samples. Administration of BH culture resulted in a notable reduction (1 log) in sulphate reducing bacteria (SRB).

Figure 5:
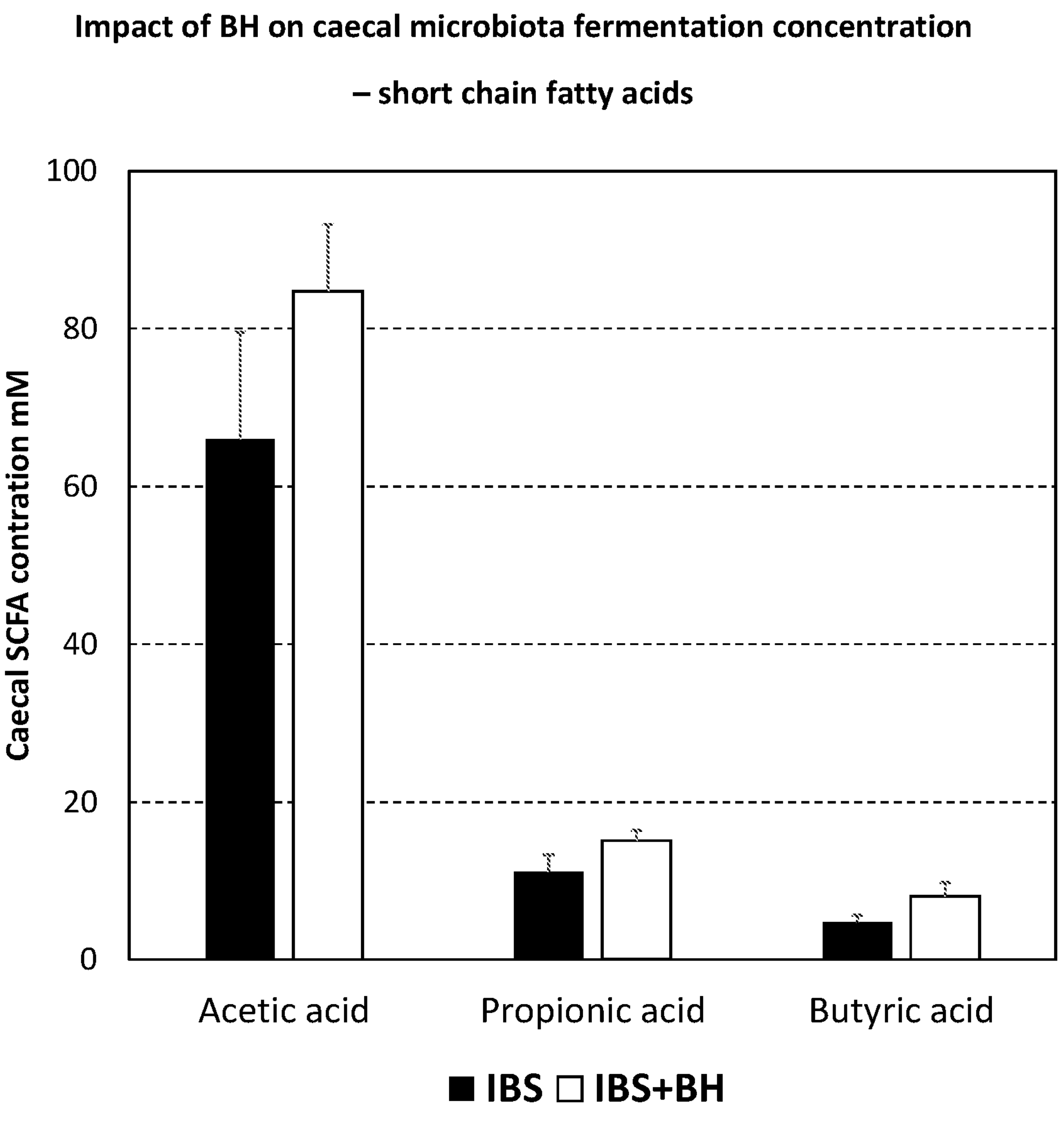
FIG. 5: Impact of BH lyophilisate on microbiota fermentation—short chain fatty acids, showing an increase in acetate production in rats treated with BH.

FIG. 5 reports on the impact of administration of BH lyophilisate on microbiota fermentation as measured by short chain fatty acid concentrations in caecal samples. Administration of BH lyophilisate resulted in an increase in acetate production.

Figure 6:
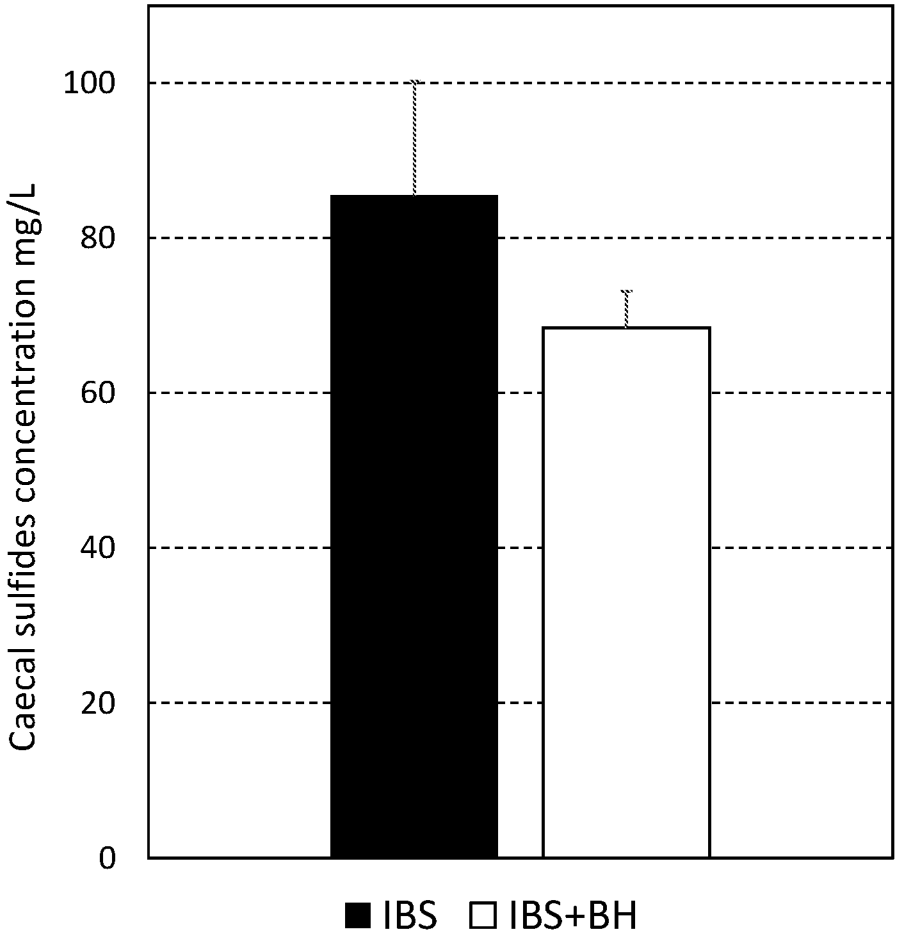
FIG. 6: Impact of BH lyophilisate on microbiota fermentation—sulphides, showing a decrease in sulphides production.

FIG. 6 reports on the impact of administration of BH lyophilisate on microbiota fermentation as measured by sulphide concentration in caecal samples ($H_2S$). Administration of BH resulted in a decrease in sulphide production.

Conclusions

Administration of compositions comprising *Blautia hydrogenotrophica* led to successful colonisation and a notable reduction in visceral hypersensitivity, as measured using the distension assay. This effect was observed when *Blautia hydrogenotrophica* was administered as a culture and as a lyophilisate. Administration of *Blautia hydrogenotrophica* also had a notable effect on microbiota constitution and fermentation, with observed reductions in SRB and sulphide production. These data indicate that *Blautia hydrogenotrophica* may be useful for reducing visceral hypersensitivity, and in particular visceral hypersensitivity associated with IBS. The reductions in visceral hypersensitivity may be associated with the observed reductions in SRB and sulphide production.

Figure 7:
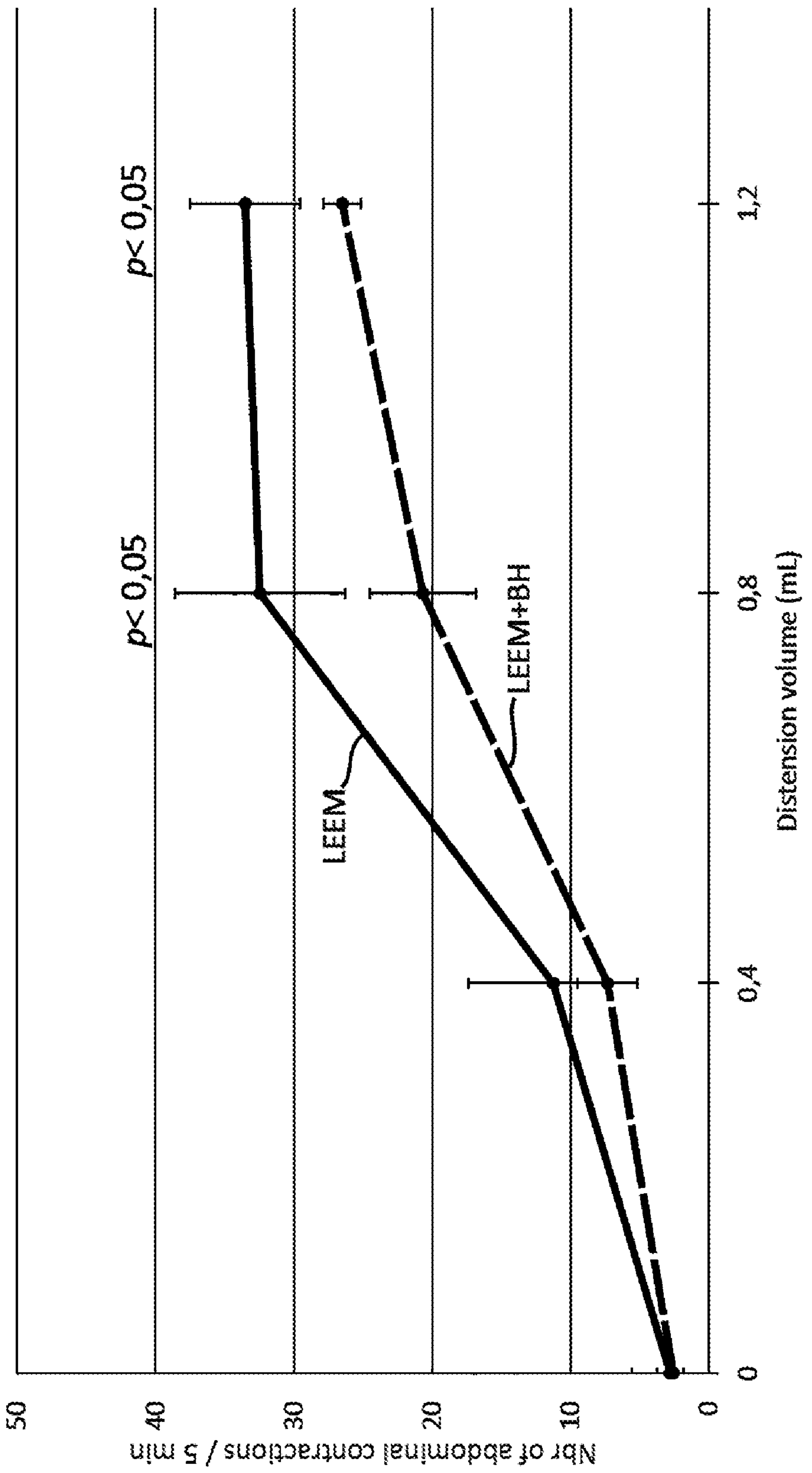
FIG. 7: Impact of BH lyophilisate on animals' response to distension. Rats MIH IBS+BH: CRD test.
Figure 8:
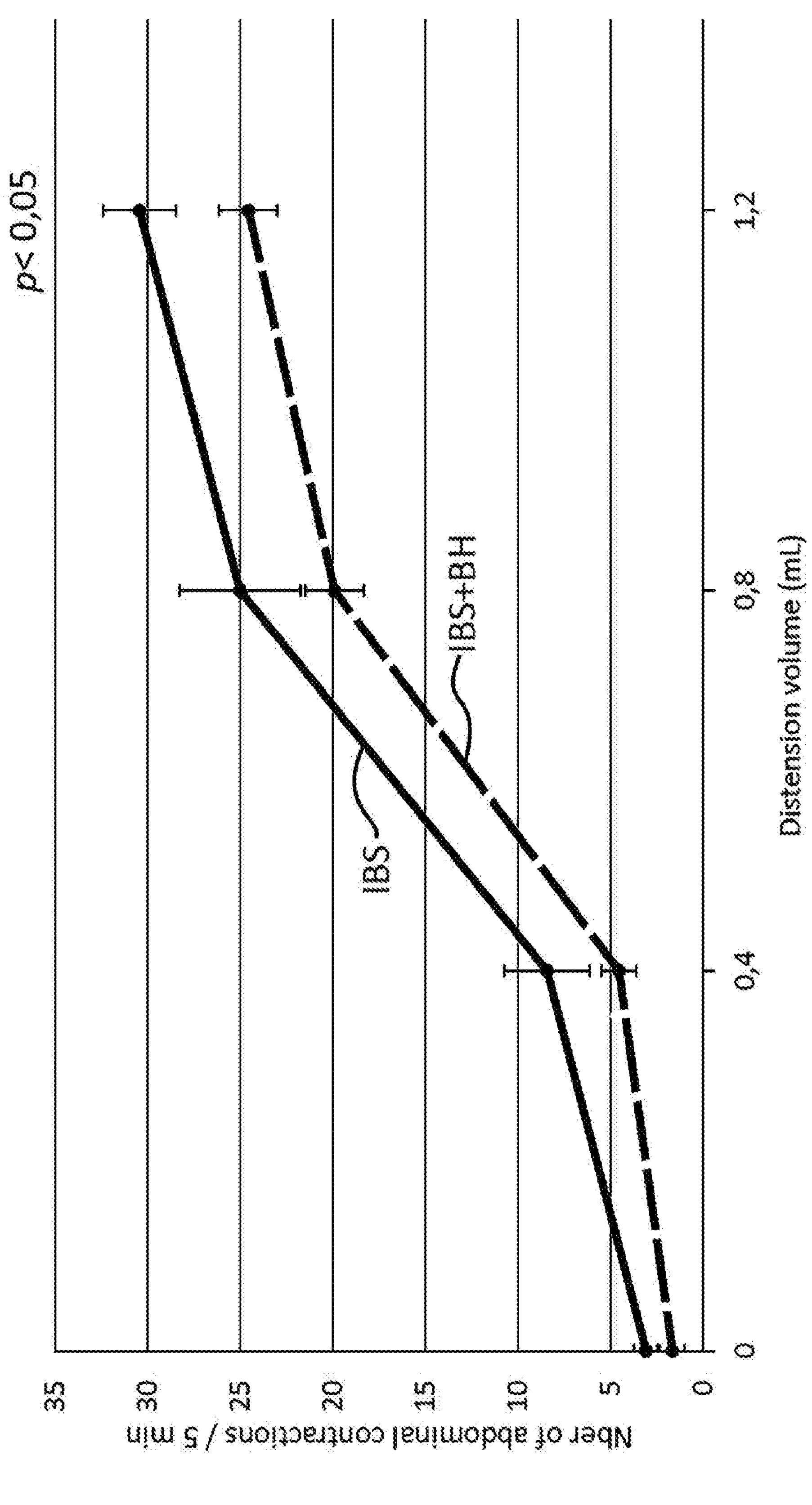
FIG. 8: Impact of BH lyophilisate on animals' response to distension. Rats MIH IBS+BH: All data—CRD test.
Figure 9A:
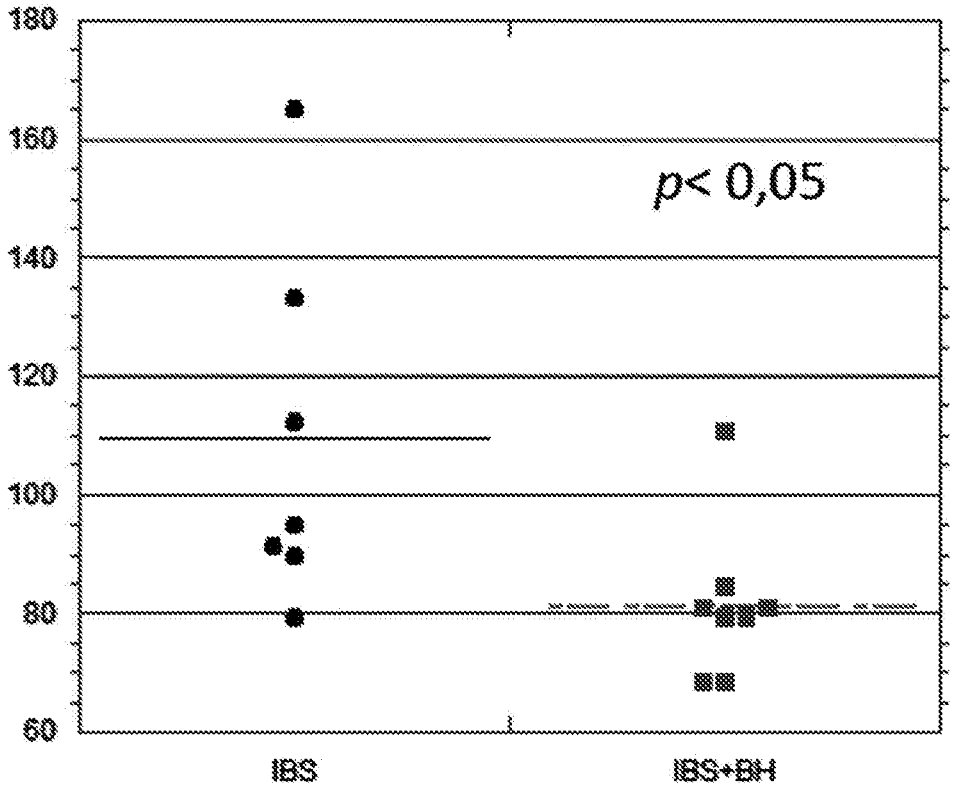
FIGS. 9A-9B: Impact of BH lyophilisate on sulphides. Rats MIH IBS+BH: Sulphides concentrations (mg/L).
Figure 9B:
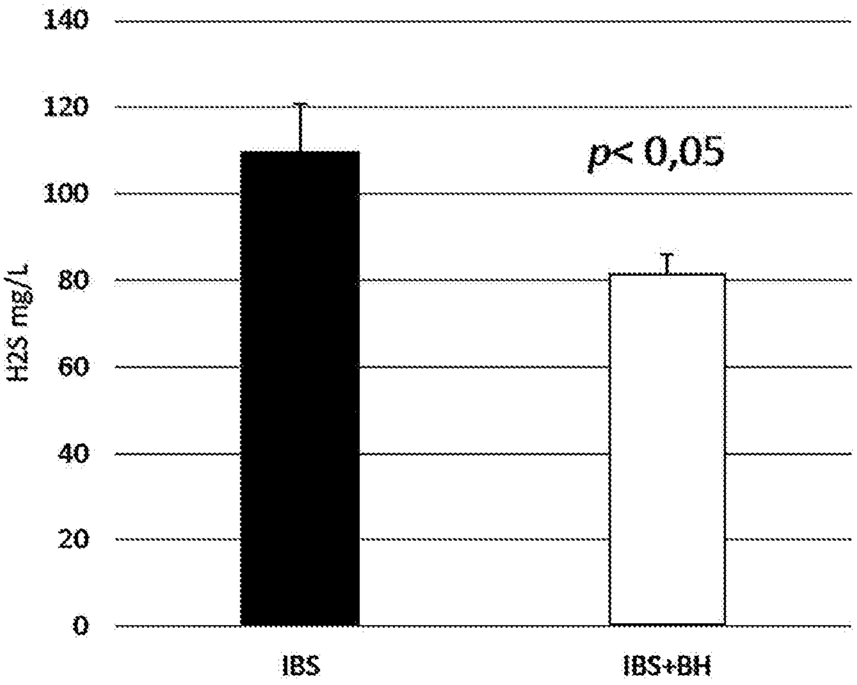
Figure 10A:
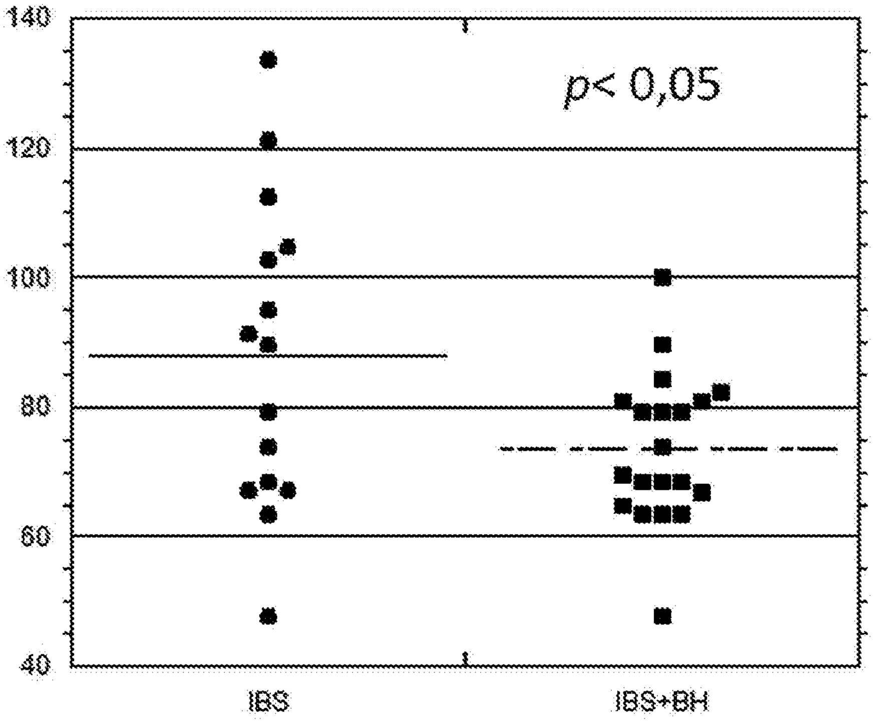
FIGS. 10A-10B: Impact of BH lyophilisate on sulphides. Rats MIH IBS+BH: All data—Sulphides concentrations (mg/L).
Figure 10B:
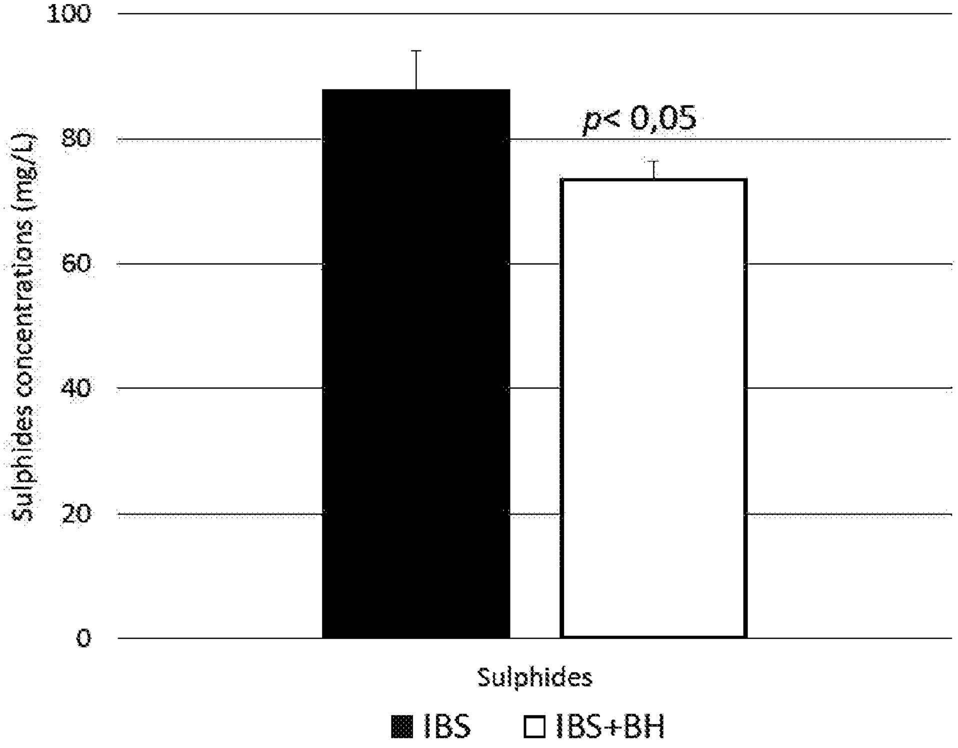

Example 2—Efficacy of Bacterial Lyophilisate in a Rat Model of Visceral Hypersensitivity The observations of Example 1 were confirmed in further experiments using a lyophilisate of *Blautia hydrogenotrophica* (BH) strain DSM 10507/14294 and a rat model of IBS. As shown in FIGS. 7 and 8, administration of BH lyophilisate provided a statistically-significant reduction in the number of abdominal contractions in response to distension, indicating a reduction in visceral hypersensitivity. Furthermore, as shown in FIGS. 9A, 9B 10A, and 10B, administration of BH lyophilisate provided a statistically-significant reduction in sulphides.

Example 3—Effects of Bacterial Lyophilisate on Healthy Rats

Figure 11:
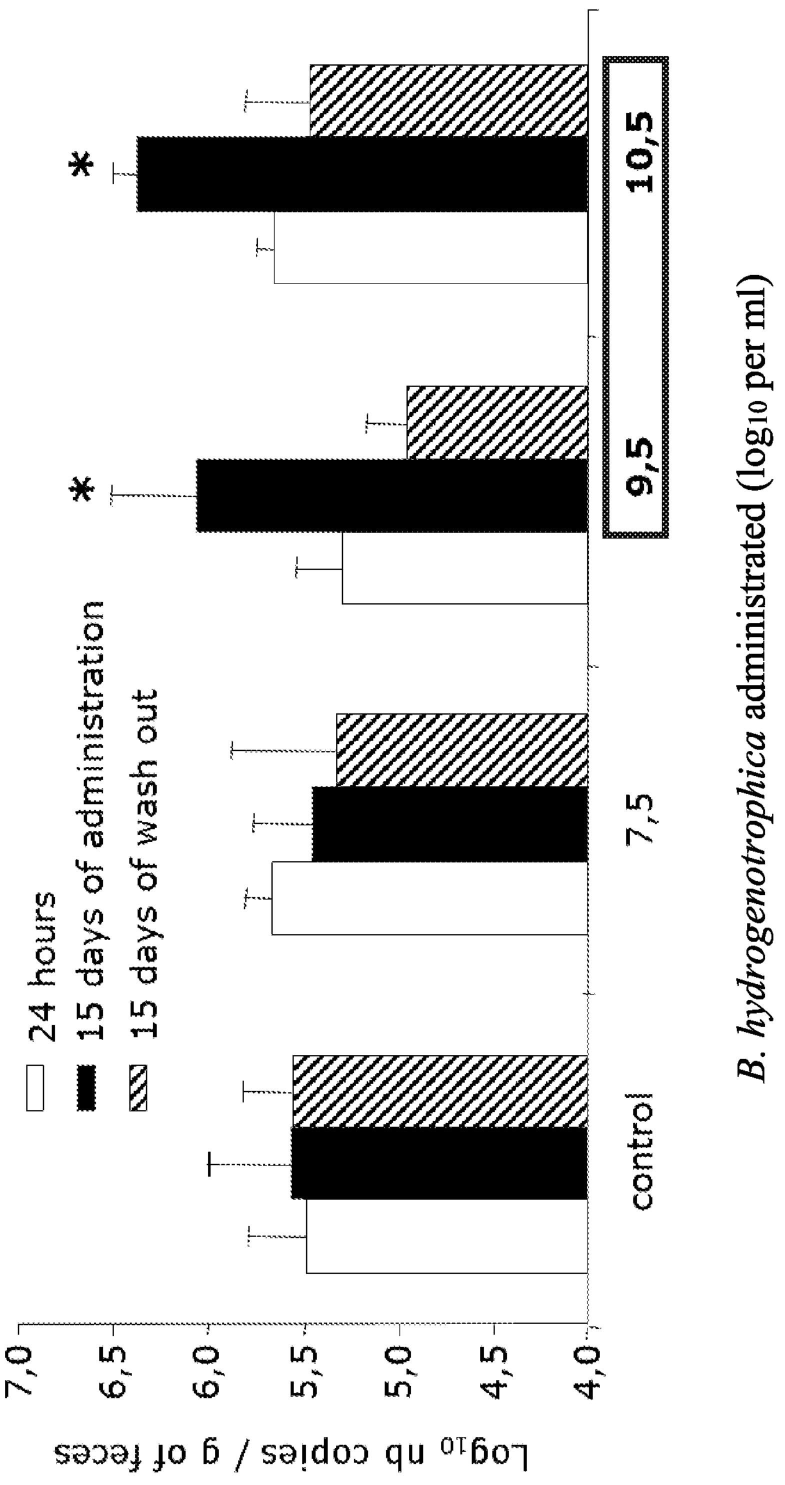
FIG. 11: Dosing study in HIM rats—RT-PCR quantification of *B. hydrogenotrophica* in fecal samples of Healthy HIM rats receiving different concentration of the bacterial species.
Figure 12:
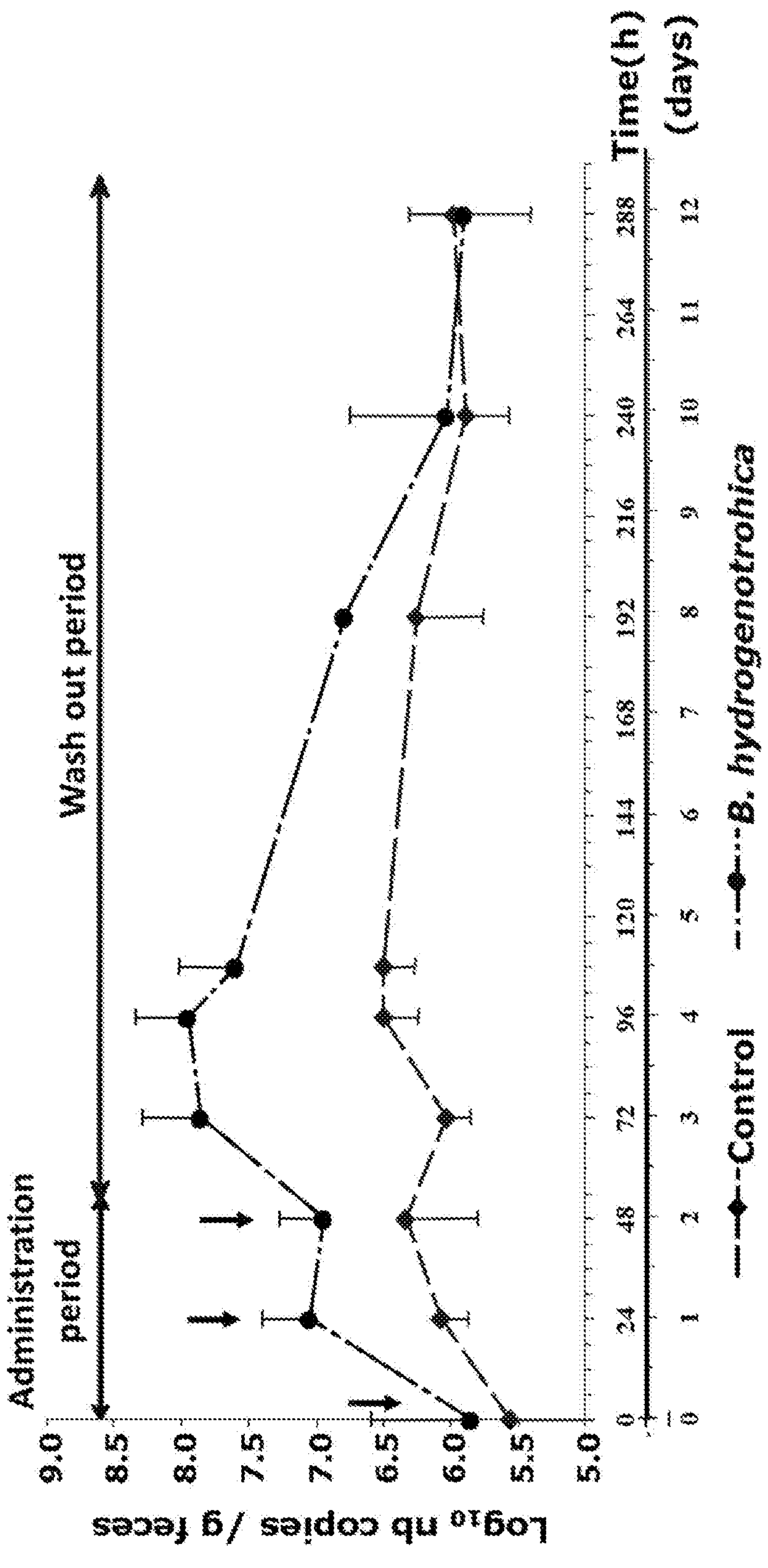
FIG. 12: Transit time of *B. hydrogenotrophica* after oral administration ($10^9$/day) to healthy HIM rats.
Figure 13:
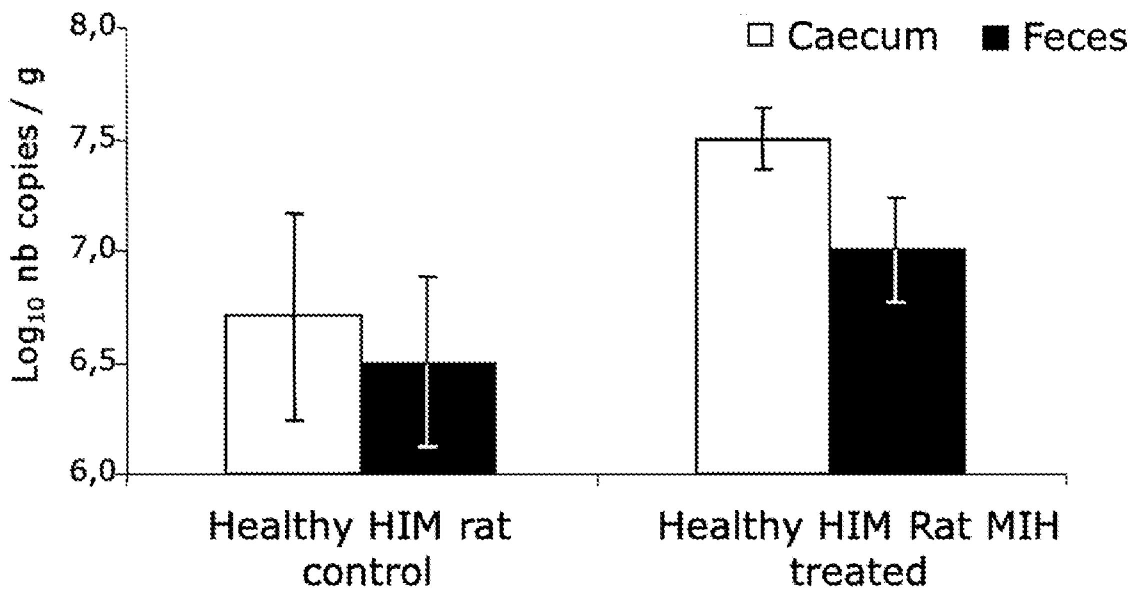
FIG. 13: Comparison of *B. hydrogenotrophica* levels found in fecal and caecal samples of healthy HIM rats (RT-PCR quantification) after 14 days administration—*B. hydrogenotrophica* administrated at $10^{10}$/day/rat.
Figure 14:
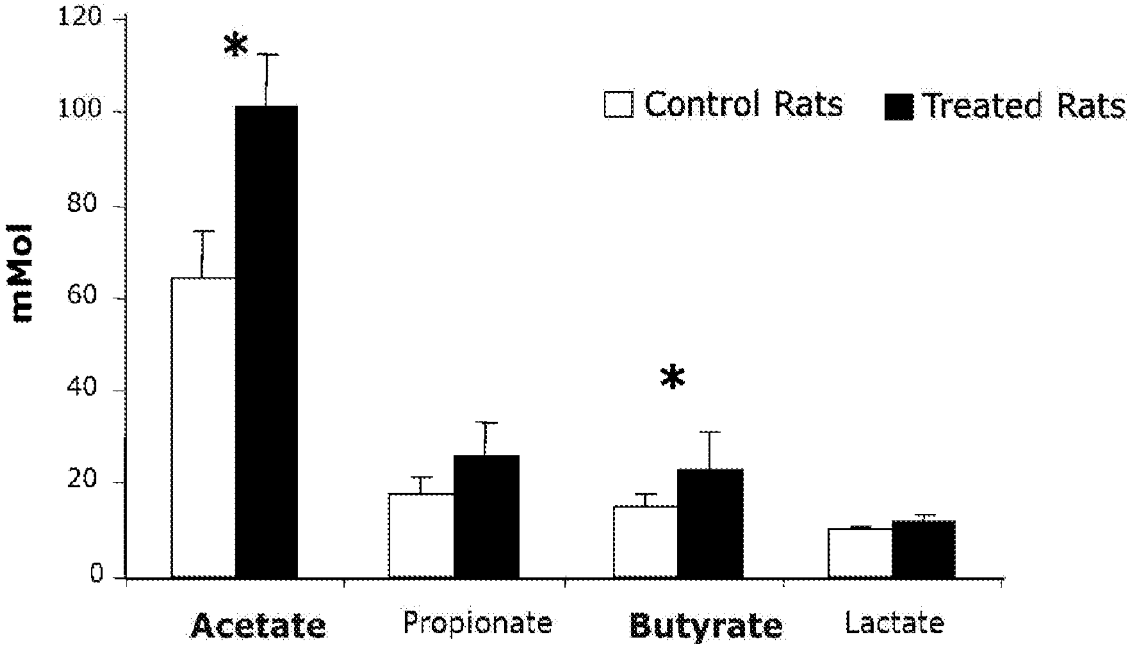
FIG. 14: Effect of *B. hydrogenotrophica* ($10^{10}$/day for 14 days) on short chain fatty acids production (RMN $^1$H) in caecal contents of healthy HIM rats.

The effects of administration of a lyophilisate of *Blautia hydrogenotrophica* (BH) strain DSM 10507/14294 on healthy HIM rats were studied and the results are reported in FIGS. 11-14. Further details regarding the experiments are provided above in the descriptions of the figures. FIG. 11 shows that an appropriate dose for BH in rats is $10^9$ cells per day or greater. FIG. 12 shows that in these experiments BH did not permanently colonise the rat digestive tract. FIG. 13 shows that BH is primarily found in the caecum. FIG. 14 shows that administration of BH induces an increase in acetate as well as in butyrate production.

Figure 15:
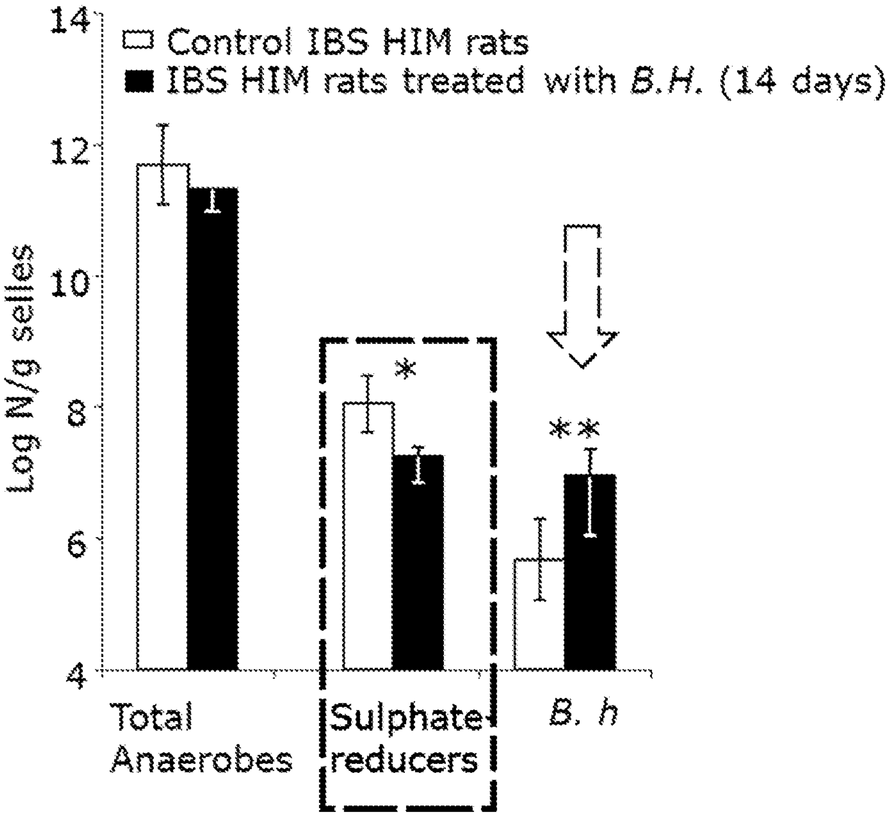
FIG. 15: Impact of *B. hydrogenotrophica* administration on the microbial populations in IBS-HIM rats.
Figure 16:
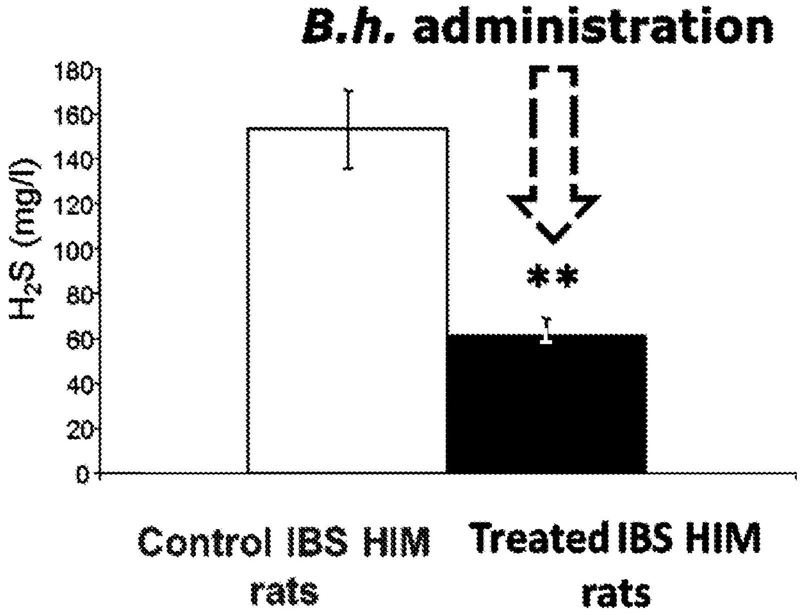
FIG. 16: Sulphides production in IBS-HIM Rats treated with *B. hydrogenotrophica* ($10^{10}$/day for 14 days). Control rats were not treated.

Example 4—Efficacy of Bacterial Lyophilisate in a Rat Model of Visceral Hypersensitivity The effects of administration of a lyophilisate of *Blautia hydrogenotrophica* (BH) strain DSM 10507/14294 on a rat model of IBS were further investigated. Germ-free rats were inoculated with faecal samples from C-IBS (with constipation) or U-IBS (unsubtyped) patients. Most of the experiments were carried out with faecal samples from IBS patients showing visceral hypersensitivity (VH measured with barostat). The results are reported in FIGS. 15 and 16 and further details regarding the experiments are provided above in the descriptions of the figures. FIG. 15 confirms that administration of BH lyophilisate causes a statistically-significant reduction in sulphate-reducing bacteria. As expected, an increase in BH is also observed. FIG. 16 shows that BH administration induced a statistically-significant decrease in the amount of $H_2S$ produced by IBS HIM rats. Over-production of caecal $H_2S$ by gut microbiota is associated with visceral hypersensitivity.

Example 5—Changes in Patient Symptoms During Phase I Clinical Trial

A Phase I clinical trial was conducted in which *Blautia hydrogenotrophica* ("Blautix", strain deposited under accession number DSM 10507 and also under accession number DSM 14294) was administered to human patients having irritable bowel syndrome (IBS). Patients were administered Blautix during a dosing period (days 1-16) with the washout period being day 19-23. Blautix was found to be both safe and well tolerated. Four symptoms were monitored, of which one was abdominal pain. The study recorded whether patients experienced an improvement in, no change in or worsening of each of these symptoms. Results from patients administered Blautix were compared with those obtained using patients administered a placebo. Symptoms were monitored at three time points: day 1, day 15/16 and at the end of the study. The results are shown in FIGS. 17 and 18.

Figure 17:
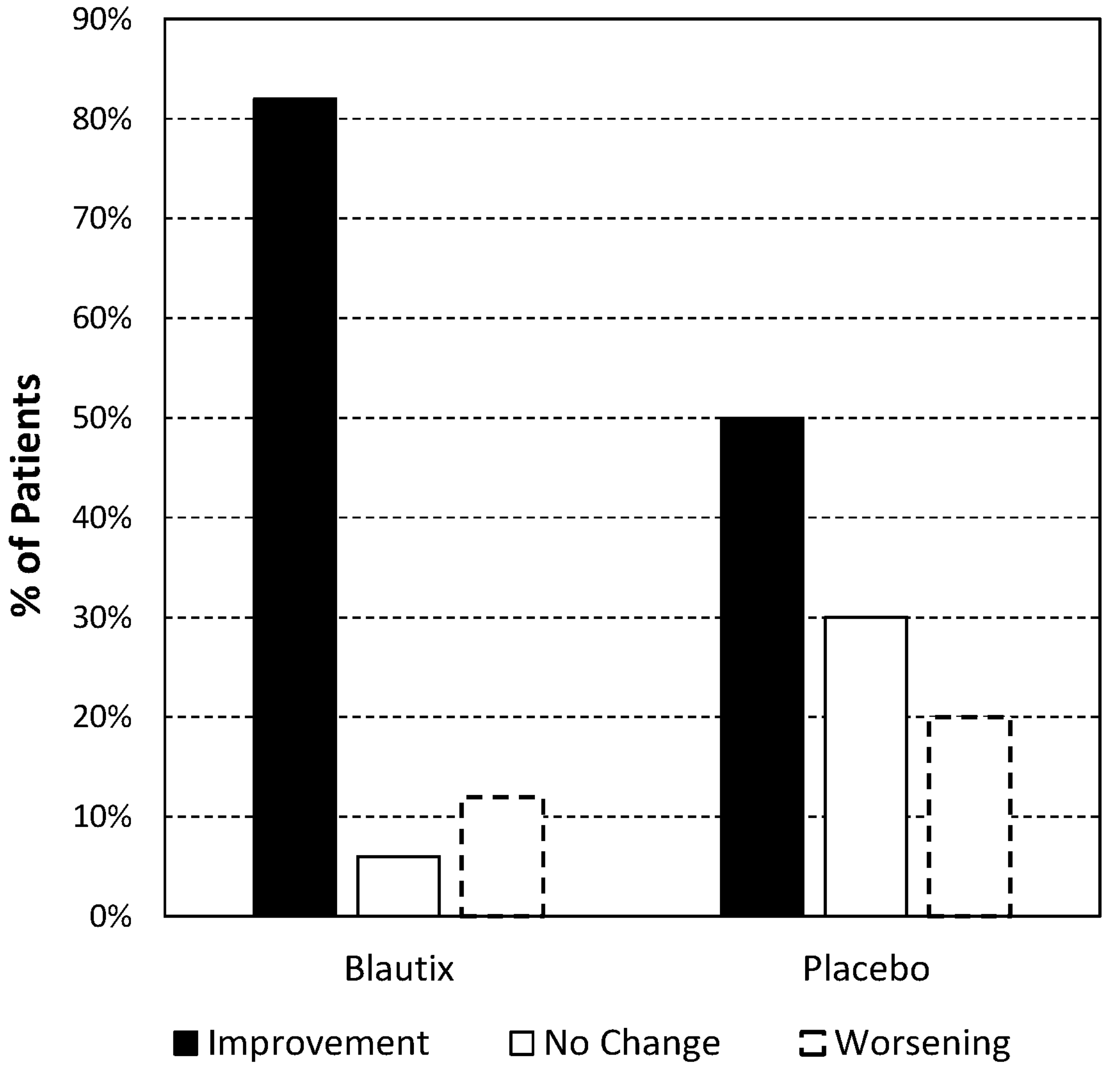
FIG. 17: Changes in patient symptoms during dosing period (days 1-16) of Phase I clinical trial.
Figure 18:
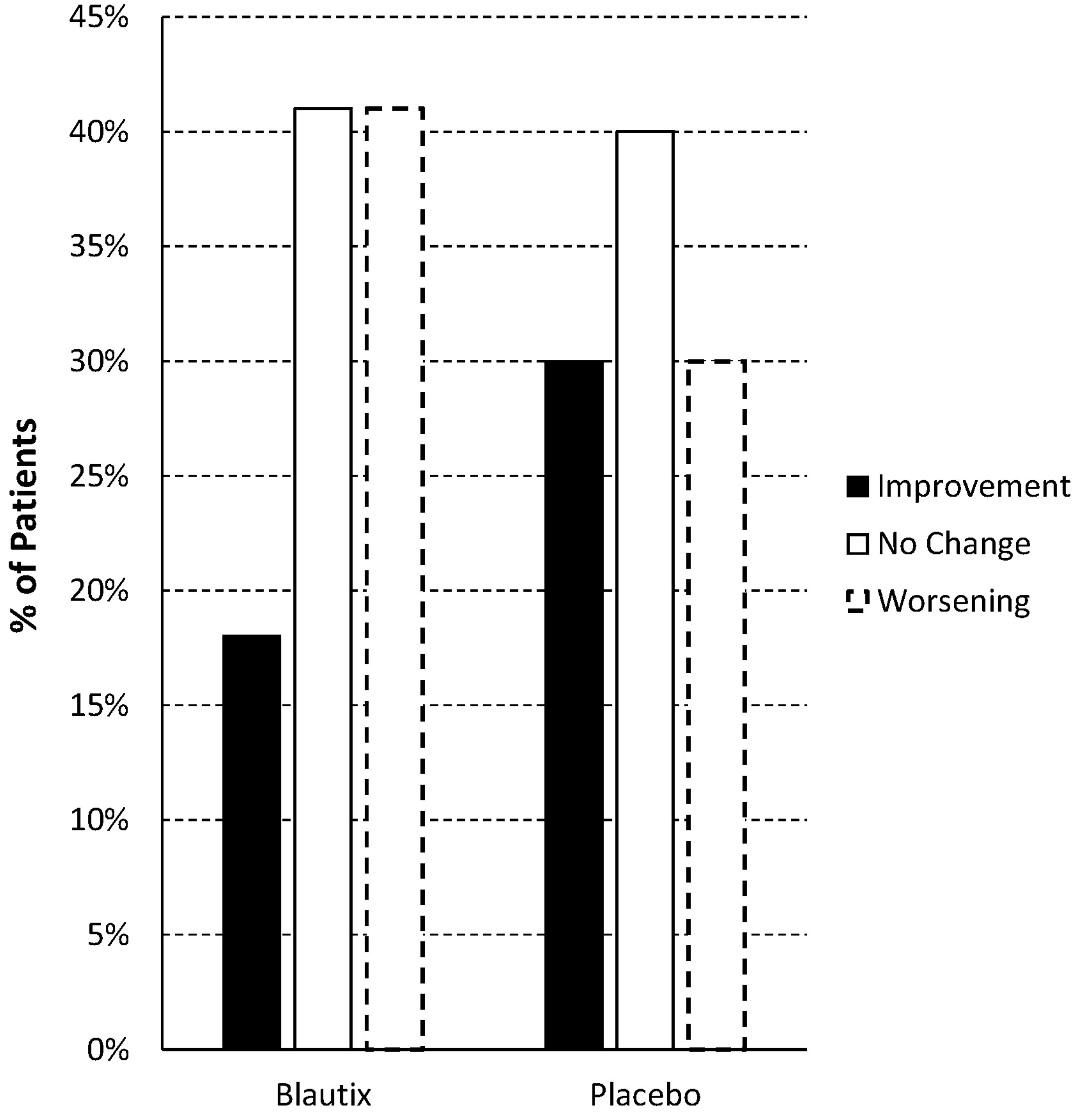
FIG. 18: Changes in patient symptoms during washout period of Phase I clinical trial.

When the patients' reported symptoms at day 16 were compared to the baseline from day 1, 82% of 17 IBS patients receiving Blautix reported an improvement in symptoms (FIG. 17). Improvement of symptoms, one of which is abdominal pain, supports the use of Blautix for treating or preventing visceral hypersensitivity. Notably, patients 3.02, 3.17 and 3.24, who all had severe abdominal pain at the beginning of the study, had mild, mild, and no abdominal pain, respectively at day 15/16.

50% of patients receiving placebo reported an improvement in symptoms (FIG. 17). High placebo response rates are an established phenomenon in IBS clinical studies. Xifaxan was recently approved to treat IBS based on much smaller improvements over placebo [45].

A worsening of symptoms at the study completion (day 19-23) compared to symptoms present upon dosing completion (day 16) is expected based on the teaching presented here. This worsening of symptoms was seen in the Phase I clinical trial: 41% of IBS patients reported worsening of symptoms following cessation of Blautix dosing (FIG. 18). The worsening of symptoms, one of which is abdominal pain, following cessation of Blautix dosing therefore also supports the use of Blautix in treating or preventing visceral hypersensitivity.

Example 6—Efficacy of *B. Hydrogenotrophica* on Visceral Hypersensitivity Studied in Human Microbiota Associated Rat (HMA Rat) Model

Summary

Groups of 20 germ-free rats were inoculated with the faecal microbiota from a human IBS subject (IBS-HMA rats). Three successive experiments were carried out using faecal samples from 3 different IBS patients. Two other groups of rats (n=10) were inoculated with faecal samples of healthy subject (n=2 subjects; 2 groups of healthy-HMA rats) as visceral sensitivity control. Half of the IBS-HMA rats were then administered for 28 days with composition comprising the bacterial strain of *B. hydrogenotrophica* according to the invention while the other half animals received a control solution. After 28 days of administration, all HMA-rats were tested using a colonic distension assay to measure visceral sensitivity. The composition of the invention were found to reduce the IBS-HMA rats' response to distension, indicating a reduction in visceral hypersensitivity that reached a normo-sensitivity as observed in healthy-HMA rats.

Strain

*Blautia hydrogenotrophica* (BH) strain DSM $10507^T$/14294.

Composition and Administration

BH lyophilisate was suspended in sterile mineral solution to a concentration of $10^{10}$ bacteria per ml. Two ml of this suspension was administered daily per IBS-HMA rat, by oral gavage, for a 28 days period.

The control solution was the sterile mineral solution that was administered daily (2 ml per rat) by oral gavage to the control group of IBS-HMA rats.

Rats

Germ-Free male Fisher rats (aged 10 weeks) were inoculated with human faecal microbiota from an IBS subject (IBS-HMA rats). Twenty rats were inoculated with the same human faecal inoculum. Three successive experiments were performed with faecal samples from three different IBS subjects. Two other groups of ten rats were inoculated with faecal sample from 2 healthy subjects (normo-sensitivity control groups).

Study Design

Day −14—Inoculation of Germ-free rats with human faecal microbiota.

Days 0 to 28—Daily dose of BH lyophilisate (assay group), or control solution (control group) by oral gavage Between days 14 and 22—operation to implant electrode into the abdomen (for distension assay) Days 22-28—Adaptation of the rats to avoid stress associated with distension test.

Day 28—distension assay and euthanasia of animals to collect the caecal samples for sulphides and short chain fatty acid (SCFA) analysis.

Days 0, 14 and 28—Collection of faecal samples for microbial analysis: qPCR for evaluating BH population and other commensal groups of miccroorganisms and enumeration of functional groups of microorganisms using selective media and strictly anaerobic method.

Results

Figure 19:
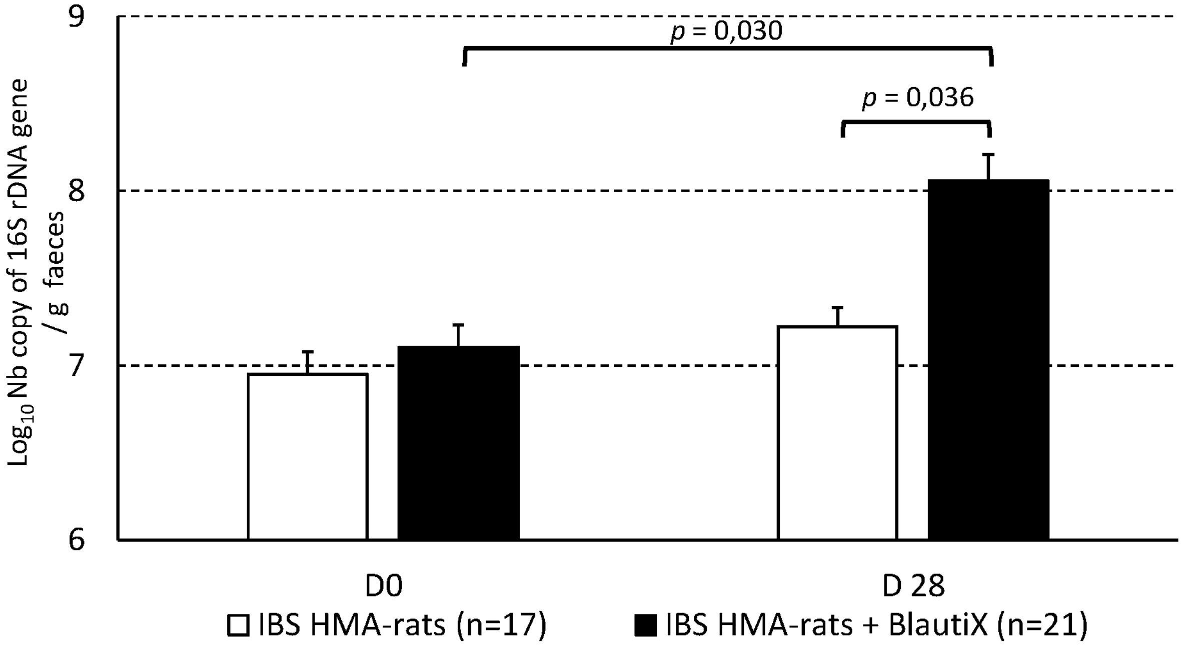
FIG. 19: qPCR evaluation of *B. hydrogenotrophica* population in faecal samples of IBS-HMA rats treated or not with a composition comprising *B. hydrogenotrophica* (BlautiX) for 28 days.

FIG. 19 presents the results of qPCR analysis of the *B. hydrogenotrophica* population in faecal samples from IBS-HMA rats receiving control solution or BH lyophilisate. A significant increase in the BH population was observed at the end of the administration period (D 28) in rats receiving the BH lyophilisate, which confirms successful delivery of BH in the colon.

Figure 20:
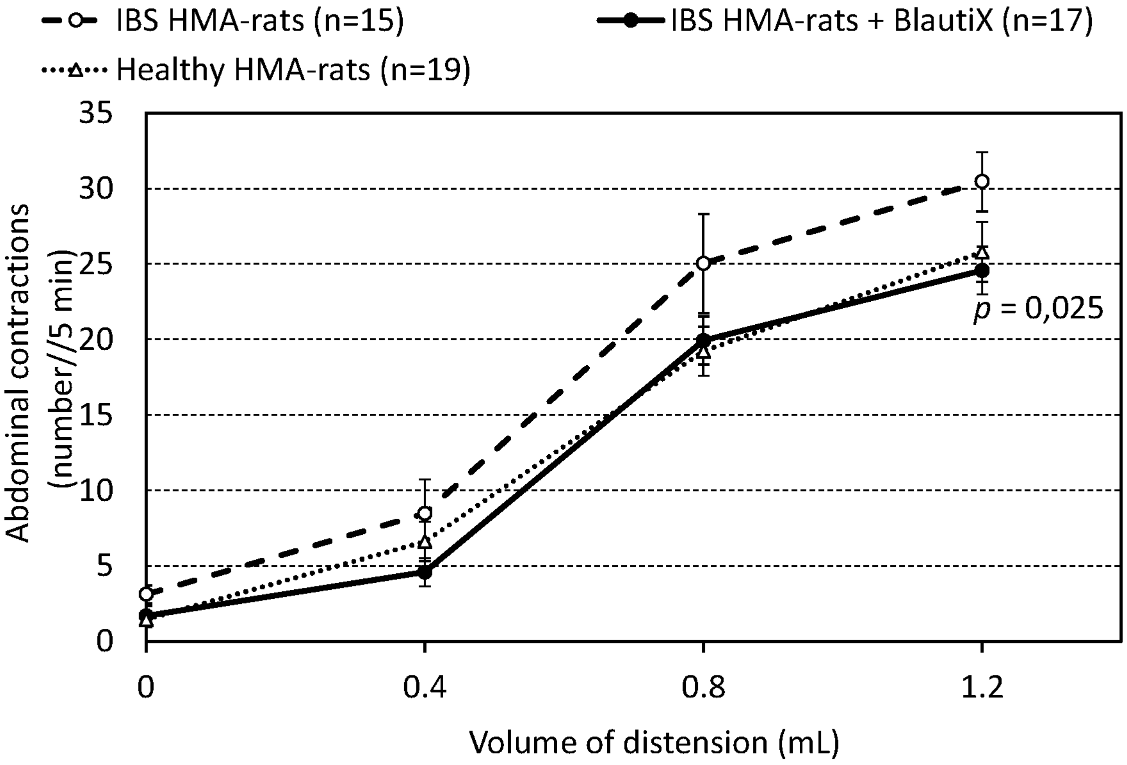
FIG. 20: Abdominal response to colorectal distension in IBS-HMA rats treated or not with *B. hydrogenotrophica* (BlautiX) for 28 days and in untreated healthy HMA rats.

FIG. 20 presents the results of the distension assay. Rats were subjected to colorectal distension and the number of contractions per 5 minutes were recorded as a specific measure of visceral hypersensitivity. The IBS-HMA rats treated with the composition of the invention exhibited reduced contractions reflecting a reduction in visceral hypersensitivity. After *B. hydrogenotrophica* treatment, the IBS-HMA rats showed a normo-visceral sensitivity, comparing with that measured in healthy HMA rats. Three of the rats within the BlautiX treatment group shown in FIG. 20 are the same as those shown in FIG. 8.

Figure 21:
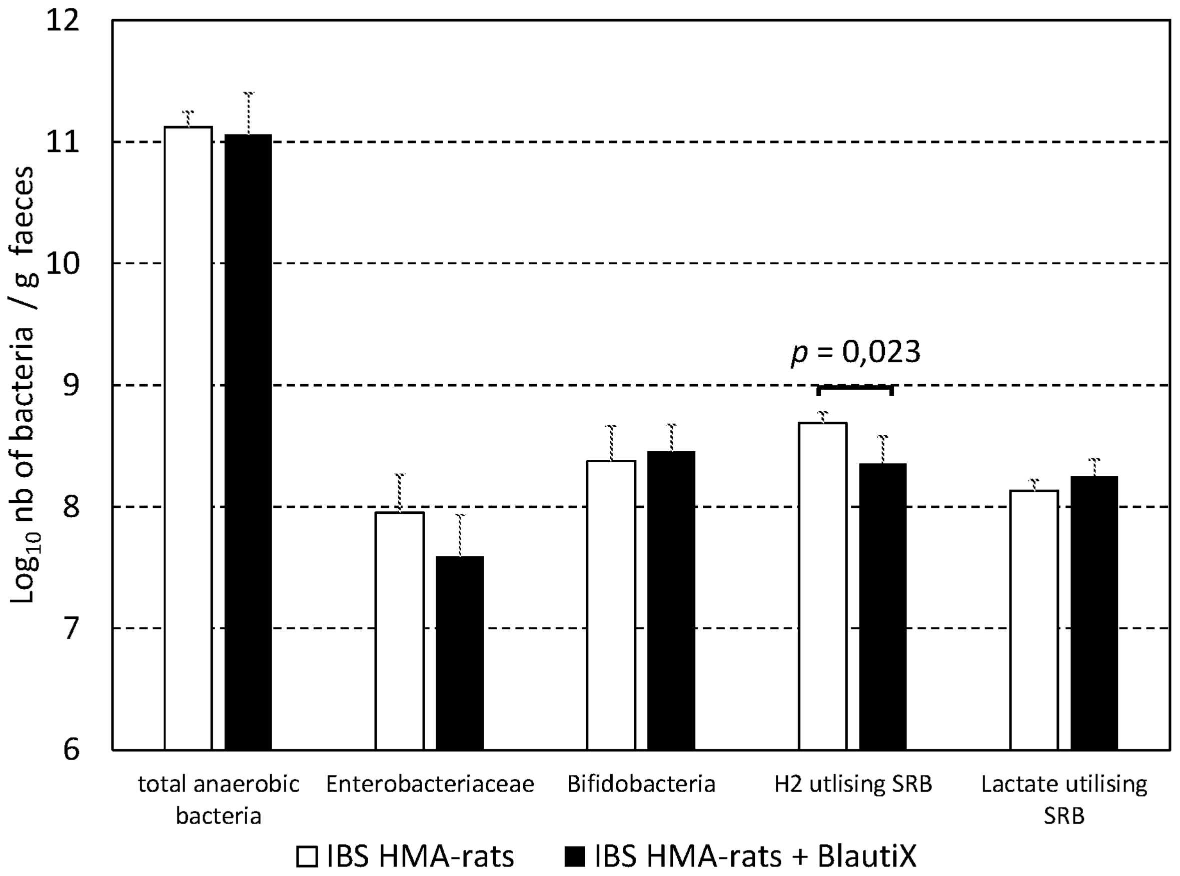
FIG. 21: Bacteria enumeration in IBS HMA-rat faecal samples after *B. hydrogenotrophica* (BlautiX) administration versus control solution.

FIG. 21 reports on the effects of administration of *B. hydrogenotrophica* on some groups of microorganisms from faecal microbiota, previously found to be affected in IBS patients. Administration of BH resulted in a significant reduction in sulphate-reducing bacteria (SRB).

Figure 22:
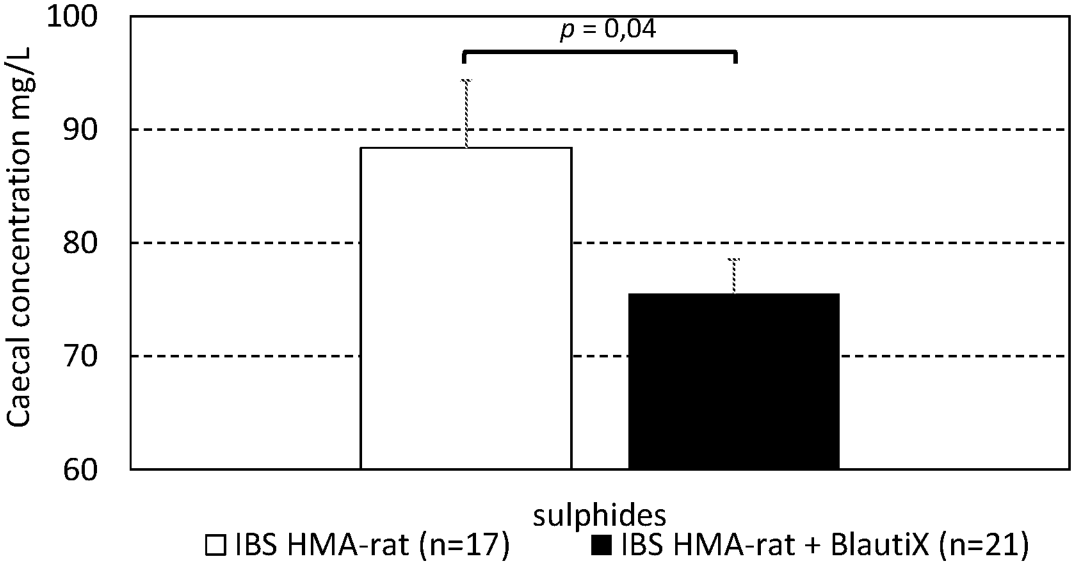
FIG. 22: Sulphide concentration in caecal samples of IBS HMA-rats treated or not with *B. hydrogenotrophica* (Blautix) for 28 days.

FIG. 22 reports on the impact of administration of BH on sulphide ($H_2S$) concentration in caecal samples of IBS-HMA rats. Administration of BH resulted in a significant decrease in sulphide production. Three of the rats within the BlautiX treatment group shown in FIG. 22 are the same as those shown in FIGS. 10A-10B.

Figure 23A:
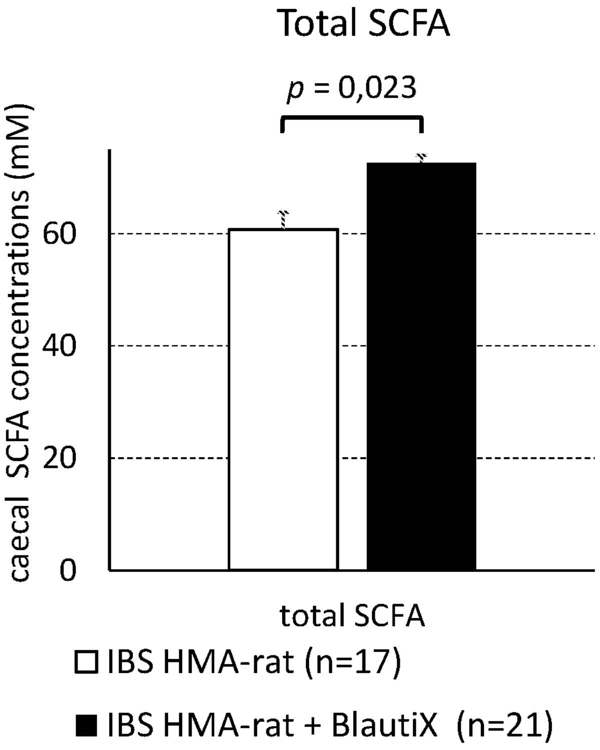
FIGS. 23A-23B: Short chain fatty acids (SCFA) concentrations in caecal samples of IBS-HMA rats treated or not with *B. hydrogenotrophica* (Blautix) for 28 days.
Figure 23B:
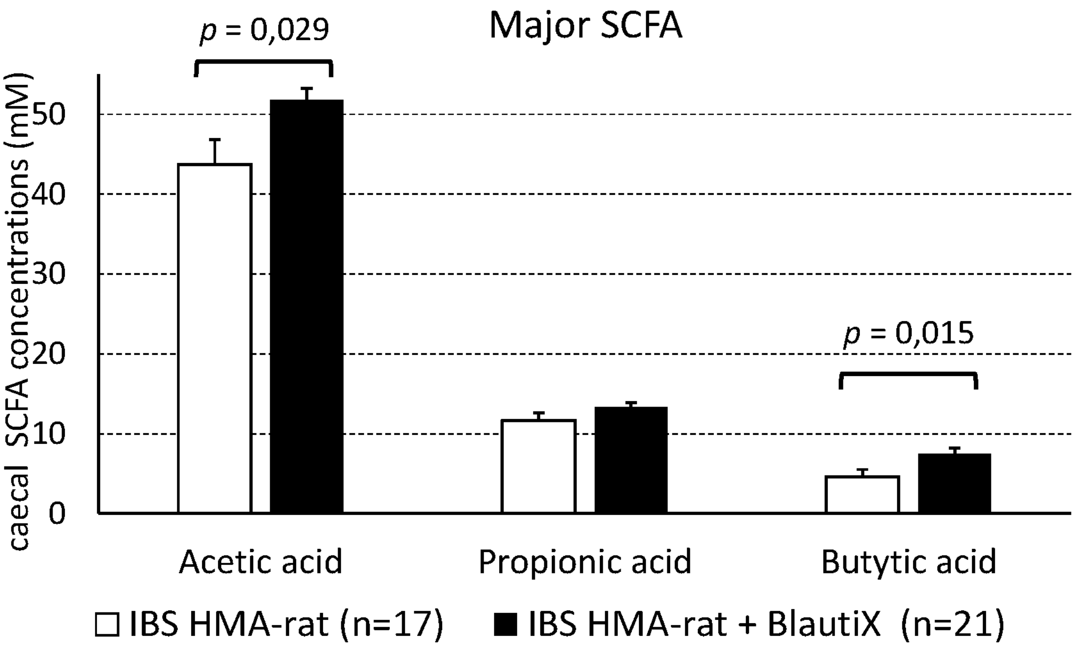

FIG. 23A reports on the impact of administration of BH on the main fermentative metabolites, short chain fatty acids, in caecal samples of IBS-HMA rats. Administration of BH-resulted in a significant increase in acetate concentration as well as in a significant increase in butyrate concentration (FIG. 23B).

Conclusions

Administration of a composition comprising *Blautia hydrogenotrophica* led a significant reduction in visceral hypersensitivity, as measured using the distension assay. After treatment, the visceral sensitivity of IBS-HMA rats was found to be similar to that measured in healthy-HMA rats. Administration of the composition comprising *B.* hydrogenotrophica can restore visceral sensitivity of IBS-HMA animals to a normal one. Administration of *Blautia hydrogenotrophica* also had a significant effect on microbiota constitution and fermentation, and especially induced important reductions in SRB and sulphide production. These data indicate that *Blautia hydrogenotrophica* may be useful for reducing visceral hypersensitivity, and in particular visceral hypersensitivity associated with IBS. The reductions in visceral hypersensitivity may be associated with the observed reductions in SRB and sulphide production.

Example 7—Stability Testing

A composition described herein containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Sequences
(*Blautia stercoris* strain GAM6-1 16S ribosomal RNA gene, partial sequence-HM626177)

SEQ ID NO: 1

```
   1 tgcaagtcga gcgaagcgct tacgacagaa ccttcggggg aagatgtaag ggactgagcg

  61 gcggacgggt gagtaacgcg tgggtaacct gcctcataca gggggataac agttggaaac

 121 ggctgctaat accgcataag cgcacggtat cgcatgatac agtgtgaaaa actccggtgg

 181 tatgagatgg acccgcgtct gattagctag ttggaggggt aacggcccac caaggcgacg

 241 atcagtagcc ggcctgagag ggtgaacggc cacattggga ctgagacacg gcccagactc

 301 ctacgggagg cagcagtggg gaatattgca caatggggga aaccctgatg cagcgacgcc

 361 gcgtgaagga agaagtatct cggtatgtaa acttctatca gcagggaaga aaatgacggt

 421 acctgactaa gaagccccgg ctaactacgt gccagcagcc gcggtaatac gtagggggca

 481 agcgttatcc ggatttactg ggtgtaaagg gagcgtagac ggaagagcaa gtctgatgtg

 541 aaaggctggg gcttaacccc aggactgcat tggaaactgt ttttcttgag tgccggagag

 601 gtaagcggaa ttcctagtgt agcggtgaaa tgcgtagata ttaggaggaa caccagtggc

 661 gaaggcggct tactggacgg taactgacgt tgaggctcga aagcgtgggg agcaaacagg

 721 attagatacc ctggtagtcc acgccgtaaa cgatgaatac taggtgttgg ggagcaaagc

 781 tcttcggtgc cgcagcaaac gcaataagta ttccacctgg ggagtacgtt cgcaagaatg

 841 aaactcaaag gaattgacgg ggacccgcac aagcggtgga gcatgtggtt taattcgaag

 901 caacgcgaag aaccttacca agtcttgaca tcgatctgac cggttcgtaa tggaaccttt

 961 ccttcgggac agagaagaca ggtggtgcat ggttgtcgtc agctcgtgtc gtgagatgtt

1021 gggttaagtc ccgcaacgag cgcaacccct atcctcagta gccagcaggt gaagctgggc

1081 actctgtgga gactgccagg gataacctgg aggaaggcgg ggacgacgtc aaatcatcat

1141 gccccttatg atttgggcta cacacgtgct acaatggcgt aaacaaaggg aagcgagccc

1201 gcgagggggga gcaaatccca aaaataacgt cccagttcgg actgcagtct gcaactcgac

1261 tgcacgaagc tggaatcgct agtaatcgcg aatcagaatg tcgcggtgaa tacgttcccg

1321 ggtcttgtac acaccgcccg tcacaccatg ggagtcagta acgcccgaag tc
```

(*Blautia wexlerae* strain WAL 14507 16S ribosomal RNA gene, partial sequence-EF036467)

SEQ ID NO: 2

```
   1 caagtcgaac gggaattant ttattgaaac ttcggtcgat ttaatttaat tctagtggcg

  61 gacgggtgag taacgcgtgg gtaacctgcc ttatacaggg ggataacagt cagaaatggc

 121 tgctaatacc gcataagcgc acagagctgc atggctcagt gtgaaaaact ccggtggtat

 181 aagatggacc cgcgttggat tagcttgttg gtggggtaac ggcccaccaa ggcgacgatc

 241 catagccggc ctgagagggt gaacggccac attgggactg agacacggcc cagactccta
```

-continued 301 cgggaggcag cagtggggaa tattgcacaa tgggggaaac cctgatgcag cgacgccgcg 361 tgaaggaaga agtatctcgg tatgtaaact tctatcagca gggaagatag tgacggtacc 421 tgactaagaa gccccggcta actacgtgcc agcagccgcg gtaatacgta gggggcaagc 481 gttatccgga tttactgggt gtaaagggag cgtagacggt gtggcaagtc tgatgtgaaa 541 ggcatgggct caacctgtgg actgcattgg aaactgtcat acttgagtgc cggaggggta 601 agcggaattc ctagtgtagc ggtgaaatgc gtagatatta ggaggaacac cagtggcgaa 661 ggcggcttac tggacggtaa ctgacgttga ggctcgaaag cgtggggagc aaacaggatt 721 agataccctg gtagtccacg ccgtaaacga tgaataacta ggtgtcgggt ggcaaagcca 781 ttcggtgccg tcgcaaacgc agtaagtatt ccacctgggg agtacgttcg caagaatgaa 841 actcaaagga attgacgggg acccgcacaa gcggtggagc atgtggttta attcgaagca 901 acgcgaagaa ccttaccaag tcttgacatc cgcctgaccg atccttaacc ggatctttcc 961 ttcgggacag gcgagacagg tggtgcatgg ttgtcgtcag ctcgtgtcgt gagatgttgg 1021 gttaagtccc gcaacgagcg caacccctat cctcagtagc cagcatttaa ggtgggcact 1081 ctggggagac tgccagggat aacctggagg aaggcgggga tgacgtcaaa tcatcatgcc 1141 ccttatgatt tgggctacac acgtgctaca atggcgtaaa caaagggaag cgagattgtg 1201 agatggagca aatcccaaaa ataacgtccc agttcggact gtagtctgca acccgactac 1261 acgaagctgg aatcgctagt aatcgcggat cagaatgccg cggtgaatac gttcccgggt 1321 cttgtacaca ccgcccgtca caccatggga gtcagtaacg cccgaagtca gtgacctaac 1381 tgcaaagaag gagctgccga aggcgggacc gatgactggg gtgaagtcgt aacaaggt (consensus 16S rRNA sequence for *Blautia stercoris* strain 830)

SEQ ID NO: 3

TTTKGTCTGGCTCAGGATGAACGCTGGCGGCGTGCTTAACACATGCAAGTCGAGCGAAGCGCTTACGACAGAACCTT

CGGGGGAAGATGTAAGGGACTGAGCGGCGGACGGGTGAGTAACGCGTGGGTAACCTGCCTCATACAGGGGGATAACA

GTTGGAAACGGCTGCTAATACCGCATAAGCGCACAGTATCGCATGATACAGTGTGAAAAACTCCGGTGGTATGAGAT

GGACCCGCGTCTGATTAGCTAGTTGGAGGGGTAACGGCCCACCAAGGCGACGATCAGTAGCCGGCCTGAGAGGGTGA

ACGGCCACATTGGGACTGAGACACGGCCCAGACTCCTACGGGAGGCAGCAGTGGGGAATATTGCACAATGGGGGAAA

CCCTGATGCAGCGACGCCGCGTGAAGGAAGAAGTATCTCGGTATGTAAACTTCTATCAGCAGGGAAGAAAATGACGG

TACCTGACTAAGAAGCCCCGGCTAACTACGTGCCAGCAGCCGCGGTAATACGTAGGGGGCAAGCGTTATCCGGATTT

ACTGGGTGTAAAGGGAGCGTAGACGGAAGAGCAAGTCTGATGTGAAAGGCTGGGGCTTAACCCCAGGACTGCATTGG

AAACTGTTTTTCTTGAGTGCCGGAGAGGTAAGCGGAATTCCTAGTGTAGCGGTGAAATGCGTAGATATTAGGAGGAA

CACCAGTGGCGAAGGCGGCTTACTGGACGGTAACTGACGTTGAGGCTCGAAAGCGTGGGGAGCAAACAGGATTAGAT

ACCCTGGTAGTCCACGCCGTAAACGATGAATACTAGGTGTTGGGGAGCAAAGCTCTTCGGTGCCGCAGCAAACGCAA

TAAGTATTCCACCTGGGGAGTACGTTCGCAAGAATGAAACTCAAAGGAATTGACGGGGACCCGCACAAGCGGTGGAG

CATGTGGTTTATTCGAAGCAACGCGAAGAACCTTACCAAGTCTTGACATCGATCTGACCGGTTCGTAATGGAACCTT

TCCTTCGGGACAGAGAAGACAGGTGGTGCATGGTTGTCGTCAGCTCGTGTCGTGAGATGTTGGGTTAAGTCCCGCAA

CGAGCGCAACCCCTATCGTCAGTAGCCAGCAGGTAAAGCTGGGCACTCTGAGGAGACTGCCAGGGATAACCTGGAGG

AAGGCGGGGACGACGTCAAATCATCATGCCCCTTATGATTTGGGCTACACACGTGCTACAATGGCGTAAACAAAGGG

AAGCGAGCCCGCGAGGGGGAGCAAATCCCAAAAATAACGTCCCAGTTCGGACTGCAGTCTGCAACTCGACTGCACGA

-continued

AGCTGGAATCGCTAGTAATCGCGAATCAGAATGTCGCGGTGAATACGTTCCCGGGTCTTGTACACACCGCCCGTCAC
ACCATGGGAGTCAGTAACGCCCGAAGTCAGTGACCCAACCTTAGGGAGGGAGCTGCCGAAGGCGGGATTGATAACTG
GGGTGAAGTCTAGGGGGT (consensus 16S rRNA sequence for *Blautia wexlerae* strain MRX008)

SEQ ID NO: 4

TTCATTGAGACTTCGGTGGATTTAGATTCTATTTCTAGTGGCGGACGGGTGAGTAACGCGTGGGTAACCTGCCTTAT
ACAGGGGGATAACAGTCAGAAATGGCTGCTAATACCGCATAAGCGCACAGAGCTGCATGGCTCAGTGTGAAAAACTC
CGGTGGTATAAGATGGACCCGCGTTGGATTAGCTTGTTGGTGGGGTAACGGCCCACCAAGGCGACGATCCATAGCCG
GCCTGAGAGGGTGAACGGCCACATTGGGACTGAGACACGGCCCAGACTCCTACGGGAGGCAGCAGTGGGGAATATTG
CACAATGGGGGAAACCCTGATGCAGCGACGCCGCGTGAAGGAAGAAGTATCTCGGTATGTAAACTTCTATCAGCAGG
GAAGATAGTGACGGTACCTGACTAAGAAGCCCCGGCTAACTACGTGCCAGCAGCCGCGGTAATACGTAGGGGGCAAG
CGTTATCCGGATTTACTGGGTGTAAAGGGAGCGTAGACGGTGTGGCAAGTCTGATGTGAAAGGCATGGGCTCAACCT
GTGGACTGCATTGGAAACTGTCATACTTGAGTGCCGGAGGGGTAAGCGGAATTCCTAGTGTAGCGGTGAAATGCGTA
GATATTAGGAGGAACACCAGTGGCGAAGGCGGCTTACTGGACGGTAACTGACGTTGAGGCTCGAAAGCGTGGGGAGC
AAACAGGATTAGATACCCTGGTAGTCCACGCCGTAAACGATGAATACTAGGTGTCNGGGGAGCATGGCTCTTCGGTG
CCGTCGCAAACGCAGTAAGTATTCCACCTGGGGAGTACGTTCGCAAGAATGAAACTCAAAGGAATTGACGGGGACCC
GCACAAGCGGTGGAGCATGTGGTTTAATTCGAAGCAACGCGAAGAACCTTACCAAGTCTTGACATCCGCCTGACCGA
TCCTTAACCGGATCTTTCCTTCGGGACAGGCGAGACAGGTGGTGCATGGTTGTCGTCAGCTCGTGTCGTGAGATGTT
GGGTTAAGTCCCGCAACGAGCGCAACCCCTATCCTCAGTAGCCAGCATTTAAGGTGGGCACTCTGGGGAGACTGCCA
GGGATAACCTGGAGGAAGGCGGGGATGACGTCAAATCATCATGCCCCTTATGATTTGGGCTACACACGTGCTACAAT
GGCGTAAACAAAGGGAAGCGAGATCGTGAGATGGAGCAAATCCCAAAAATAACGTCCCAGTTCGGACTGTAGTCTGC
AACCCGACTACACGAAGCTGGAATCGCTAGTAATCGCGGATCAGAATGCCGCGGTGAATACGTTCCCGGGTCTTGTA
CACACCGCCCGTCACACCATGGGAGTCAGTAACGCCCGAAGTCAGTGACCTAACTGCAAAGAAGGAGCTGCCGAA (*Blautia hydrogenotrophica* strain S5a36 16S ribosomal RNA gene, partial sequence-X95624.1)

SEQ ID NO: 5

```
   1 gatgaacgct ggcggcgtgc ttaacacatg caagtcgaac gaagcgatag agaacggaga
  61 tttcggttga agttttctat tgactgagtg gcggacgggt gagtaacgcg tgggtaacct
 121 gccctataca gggggataac agttagaaat gactgctaat accgcataag cgcacagctt
 181 cgcatgaagc ggtgtgaaaa actgaggtgg tataggatgg acccgcgttg gattagctag
 241 ttggtgaggt aacggcccac caaggcgacg atccatagcc ggcctgagag ggtgaacggc
 301 cacattggga ctgagacacg gcccaaactc ctacgggagg cagcagtggg gaatattgca
 361 caatggggga aaccctgatg cagcgacgcc gcgtgaagga agaagtatct cggtatgtaa
 421 acttctatca gcagggaaga aagtgacggt acctgactaa gaagccccgg ctaattacgt
 481 gccagcagcc gcggtaatac gtaaggggca agcgttatcc ggatttactg ggtgtaaagg
 541 gagcgtagac ggtttggcaa gtctgatgtg aaaggcatgg gctcaacctg tggactgcat
 601 tggaaactgt cagacttgag tgccggagag gcaagcggaa ttcctagtgt agcggtgaaa
 661 tgcgtagata ttaggaggaa caccagtggc gaaggcggcc tgctggacgg taactgacgt
 721 tgaggctcga aagcgtgggg agcaaacagg attagatacc ctggtagtcc acgctgtaaa
 781 cgatgaatac taggtgtcgg gtggcaaagc cattcggtgc cgcagcaaac gcaataagta
 841 ttcccacctg gggagtacgt tcgcaagaat gaaactcaaa ggaattgacg gggacccgca
 901 caagcggtgg agcatgtggt ttaattcgaa gcaacgcgaa gaaccttacc aaatcttgac
 961 atccctctga ccgggaagta atgttccctt ttcttcggaa cagaggagac aggtggtgca
```

-continued

```
1021 tggttgtcgt cagctcgtgt cgtgagatgt tgggttaagt cccgcaacga gcgcaaccct

1081 tattcttagt agccagcagg tagagctggg cactctaggg agactgccag ggataacctg

1141 gaggaaggtg gggatgacgt caaatcatca tgccccttat gatttgggct acacacgtgc

1201 tacaatggcg taaacaaagg gaagcgaagg ggtgacctgg agcaaatctc aaaaataacg

1261 tctcagttcg gattgtagtc tgcaactcga ctacatgaag ctggaatcgc tagtaatcgc

1321 gaatcagaat gtcgcggtga atacgttccc gggtcttgta cacaccgccc gtcacaccat

1381 gggagtcagt aacgcccgaa gtcagtgacc caaccnaaag gagggagctg ccgaaggtgg

1441 gactgataac tggggtga
```

REFERENCES

[1] Spor et al. (2011) *Nat Rev Microbiol.* 9(4):279-90.

[2] Eckburg et al. (2005) *Science.* 10; 308(5728):1635-8.

[3] Tap et al. (2009), *Environ Microbiol,* 11(10):2574-84.

[4] Macpherson et al. (2001) *Microbes Infect.* 3(12):1021-35

[5] Macpherson et al. (2002) *Cell Mol Life Sci.* 59(12):2088-96.

[6] Mazmanian et al. (2005) *Cell* 15; 122(1):107-18.

[7] Frank et al. (2007) *PNAS* 104(34):13780-5.

[8] Scanlan et al. (2006) *J Clin Microbiol.* 44(11):3980-8.

[9] Kang et al. (2010) *Inflamm Bowel Dis.* 16(12):2034-42.

[10] Machiels et al. (2013) Gut. 63(8):1275-83.

[11] Lopetuso et al. (2013), *Gut Pathogens,* 5: 23

[12] WO 2013/050792

[13] WO 03/046580

[14] WO 2013/008039

[15] WO 2014/167338

[16] Lee and Lee (2014) *World J Gastroenterol.* 20(27): 8886-8897.

[17] Liu et al. (2008) *Int J Syst Evol Microbiol* 58, 1896-1902.

[18] Bernalier et al. (1996) *Arch. Microbiol.* 166 (3), 176-183.

[19] Park et al. (2012) *Int J Syst Evol Microbiol.* 62(Pt 4):776-9.

[20] Masco et al. (2003) *Systematic and Applied Microbiology,* 26:557-563.

[21] Srůtková et al. (2011) *J. Microbiol. Methods,* 87(1):10-6.

[22] Robinson and Gebhart (2008) *Mol Interv,* 8(5): 242-253.

[23] Zhou et al. (2010) *Pain.* 148(3): 454-461.

[24] Miyamoto-Shinohara et al. (2008) *J. Gen. Appl. Microbiol.,* 54, 9-24.

[25] Cryopreservation and Freeze-Drying Protocols, ed. by Day and McLellan, Humana Press.

[26] Leslie et al. (1995) *Appl. Environ. Microbiol.* 61, 3592-3597.

[27] Mitropoulou et al. (2013) *J Nutr Metab.* (2013) 716861.

[28] Kailasapathy et al. (2002) *Curr Issues Intest Microbiol.* 3(2):39-48.

[29] Handbook of Pharmaceutical Excipients, 2nd Edition, (1994), Edited by A Wade and P J Weller

[30] Remington's Pharmaceutical Sciences, Mack Publishing Co. (A. R. Gennaro edit. 1985)

[31] US 2016/0067188

[32] *Handbook of Microbiological Media, Fourth Edition* (2010) Ronald Atlas, CRC Press.

[33] Maintaining Cultures for Biotechnology and Industry (1996) Jennie C. Hunter-Cevera, Academic Press

[34] Strobel (2009) *Methods Mol Biol.* 581:247-61.

[35] Gennaro (2000) *Remington: The Science and Practice of Pharmacy.* 20th edition, ISBN: 0683306472.

[36] *Molecular Biology Techniques: An Intensive Laboratory Course*, (Ream et al., eds., 1998, Academic Press).

[37] Methods In Enzymology (S. Colowick and N. Kaplan, eds., Academic Press, Inc.)

[38] *Handbook of Experimental Immunology*, Vols. I-IV (D. M. Weir and C. C. Blackwell, eds, 1986, Blackwell Scientific Publications)

[39] Sambrook et al. (2001) *Molecular Cloning: A Laboratory Manual,* 3rd edition (Cold Spring Harbor Laboratory Press).

[40] *Handbook of Surface and Colloidal Chemistry* (Birdi, K. S. ed., CRC Press, 1997)

[41] Ausubel et al. (eds) (2002) *Short protocols in molecular biology,* 5th edition (Current Protocols).

[42] *PCR* (*Introduction to Biotechniques Series*), 2nd ed. (Newton & Graham eds., 1997, Springer Verlag)

[43] *Current Protocols in Molecular Biology* (F. M. Ausubel et al., eds., 1987) Supplement 30

[44] Smith & Waterman (1981) *Adv. Appl. Math.* 2: 482-489.

[45] XIFAXAN—rifaximin tablet, Salix Pharmaceuticals, Inc.—FDA Highlights of Prescribing Information, Revised November 2015

The invention claimed is:

1. A pharmaceutical composition that comprises a therapeutically effective amount of a lyophilized bacteria strain of the species *Blautia hydrogenotrophica* to treat visceral hypersensitivity in a subject in need thereof, wherein the therapeutically effective amount comprises from $1\times10^3$ to $1\times10^{12}$ colony forming units (CFU)/g of the lyophilized bacteria strain, with respect to total weight of said pharmaceutical composition, wherein the bacteria strain comprises the 16s rRNA gene sequence set forth in SEQ ID NO: 5;

an oxygen scavenger that is vitamin C; a compound selected from the group consisting of inulin, transgalacto-oligosaccharides, fructo-oligosaccharides, isomalt-oligosaccharides, pectins, xylo-oligosaccharides, chitosan-oligosaccharides, beta-glucans, arable gum modified and resistant starches, polydextrose, D-tagatose, acacia fibers, carob, oats, citrus fibers, non-digestible carbohydrates, and sugar alcohols, or any combination thereof; and a pharmaceutically acceptable excipient, diluent, or carrier;

wherein the therapeutically effective amount is sufficient to increase an amount of butyrate in the gastrointestinal tract of the subject relative to a corresponding amount of butyrate prior to the administration or to decrease an amount of a sulphide reducing bacteria in the gastrointestinal tract of the subject relative to a corresponding amount of the sulphide reducing bacteria prior administration; and wherein said pharmaceutical composition is a solid enteric formulation and is encapsulated.

2. The pharmaceutical composition of claim 1, wherein said bacteria strain colonizes an intestine of a subject when administered to said subject.

3. The pharmaceutical composition of claim 1, wherein said pharmaceutical composition is formulated for oral or rectal delivery.

4. The pharmaceutical composition of claim 1, wherein said bacteria strain is the bacteria strain deposited under accession number DSM 10507, DSM 14294, or a biotype thereof.

5. A method of treating visceral hypersensitivity in a subject in need thereof comprising administering to said subject a pharmaceutical composition that comprises a therapeutically effective amount of a lyophilized bacteria strain of the species *Blautia hydrogenotrophica* to treat visceral hypersensitivity in the subject, wherein the bacteria strain comprises the 16s rRNA gene sequence set forth in SEQ ID NO: 5; an oxygen scavenger that is vitamin C; a compound selected from the group consisting of inulin, transgalacto-oligosaccharides, fructo-oligosaccharides, isomalt-oligosaccharides, pectins, xylo-oligosaccharides, chitosan-oligosaccharides, beta-glucans, arable gum modified and resistant starches, polydextrose, D-tagatose, acacia fibers, carob, oats, citrus fibers, non-digestible carbohydrates, and sugar alcohols, or any combination thereof; and a pharmaceutically acceptable excipient, diluent, or carrier;

wherein said therapeutically effective amount comprises from $1\times10^3$ to $1\times10^{12}$ colony forming units (CFU) per gram of the lyophilized bacteria strain with respect to total weight of said pharmaceutical composition;

wherein said pharmaceutical composition is a solid enteric formulation and is encapsulated; and wherein said therapeutically effective amount is sufficient to increase an amount of butyrate in the gastrointestinal tract of the subject relative to a corresponding amount of butyrate prior to the administration or to decrease an amount of a sulphide reducing bacteria in the gastrointestinal tract of the subject relative to a corresponding amount of the sulphide reducing bacteria prior administration.

6. The method of claim 5, wherein said bacteria strain colonizes an intestine of said subject when administered to said subject.

7. The method of claim 5, wherein said bacteria strain is the *Blautia hydrogenotrophica* bacteria strain deposited under accession number DSM 10507, DSM 14294, or a biotype thereof.

8. The method of claim 5, wherein said administering comprises oral, rectal, nasal, buccal, sublingual, or subcutaneous administration.

9. The method of claim 5, wherein said subject has irritable bowel syndrome.

10. The method of claim 5, wherein said subject is a human.

* * * * *

SEQUENCE LISTING

```
<160> NUMBER OF SEQ ID NOS: 5

<210> SEQ ID NO 1
<211> LENGTH: 1372
<212> TYPE: DNA
<213> ORGANISM: Blautia stercoris

<400> SEQUENCE: 1

tgcaagtcga gcgaagcgct tacgacagaa ccttcggggg aagatgtaag ggactgagcg      60
```

```
gcggacgggt gagtaacgcg tgggtaacct gcctcataca gggggataac agttggaaac    120
ggctgctaat accgcataag cgcacggtat cgcatgatac agtgtgaaaa actccggtgg    180
tatgagatgg acccgcgtct gattagctag ttggaggggt aacggcccac caaggcgacg    240
atcagtagcc ggcctgagag ggtgaacggc cacattggga ctgagacacg gcccagactc    300
ctacgggagg cagcagtggg gaatattgca caatggggga aaccctgatg cagcgacgcc    360
gcgtgaagga agaagtatct cggtatgtaa acttctatca gcagggaaga aaatgacggt    420
acctgactaa gaagccccgg ctaactacgt gccagcagcc gcggtaatac gtagggggca    480
agcgttatcc ggatttactg ggtgtaaagg gagcgtagac ggaagagcaa gtctgatgtg    540
aaaggctggg gcttaacccc aggactgcat tggaaactgt ttttcttgag tgccggagag    600
gtaagcggaa ttcctagtgt agcggtgaaa tgcgtagata ttaggaggaa caccagtggc    660
gaaggcggct tactggacgg taactgacgt tgaggctcga aagcgtgggg agcaaacagg    720
attagatacc ctggtagtcc acgccgtaaa cgatgaatac taggtgttgg ggagcaaagc    780
tcttcggtgc cgcagcaaac gcaataagta ttccacctgg ggagtacgtt cgcaagaatg    840
aaactcaaag gaattgacgg ggacccgcac aagcggtgga gcatgtggtt taattcgaag    900
caacgcgaag aaccttacca agtcttgaca tcgatctgac cggttcgtaa tggaaccttt    960
ccttcgggac agagaagaca ggtggtgcat ggttgtcgtc agctcgtgtc gtgagatgtt   1020
gggttaagtc ccgcaacgag cgcaacccct atcctcagta gccagcaggt gaagctgggc   1080
actctgtgga gactgccagg gataacctgg aggaaggcgg ggacgacgtc aaatcatcat   1140
gccccttatg atttgggcta cacacgtgct acaatggcgt aaacaaaggg aagcgagccc   1200
gcgaggggga gcaaatccca aaaataacgt cccagttcgg actgcagtct gcaactcgac   1260
tgcacgaagc tggaatcgct agtaatcgcg aatcagaatg tcgcggtgaa tacgttcccg   1320
ggtcttgtac acaccgcccg tcacaccatg ggagtcagta acgcccgaag tc           1372
```

<210> SEQ ID NO 2
<211> LENGTH: 1438
<212> TYPE: DNA
<213> ORGANISM: Blautia wexlerae
<220> FEATURE:
<221> NAME/KEY: modifed base
<222> LOCATION: 19
<223> OTHER INFORMATION: 'n' is a, c, g or t

<400> SEQUENCE: 2

```
caagtcgaac gggaattant ttattgaaac ttcggtcgat ttaatttaat tctagtggcg     60
gacgggtgag taacgcgtgg gtaacctgcc ttatacaggg ggataacagt cagaaatggc    120
tgctaatacc gcataagcgc acagagctgc atggctcagt gtgaaaaact ccggtggtat    180
aagatggacc cgcgttggat tagcttgttg gtggggtaac ggcccaccaa ggcgacgatc    240
catagccggc ctgagagggt gaacggccac attgggactg agacacggcc cagactccta    300
cgggaggcag cagtggggaa tattgcacaa tgggggaaac cctgatgcag cgacgccgcg    360
tgaaggaaga agtatctcgg tatgtaaact tctatcagca gggaagatag tgacggtacc    420
tgactaagaa gccccggcta actacgtgcc agcagccgcg gtaatacgta gggggcaagc    480
gttatccgga tttactgggt gtaaagggag cgtagacggt gtggcaagtc tgatgtgaaa    540
ggcatgggct caacctgtgg actgcattgg aaactgtcat acttgagtgc cggaggggta    600
agcggaattc ctagtgtagc ggtgaaatgc gtagatatta ggaggaacac cagtggcgaa    660
```

```
ggcggcttac tggacggtaa ctgacgttga ggctcgaaag cgtggggagc aaacaggatt    720

agataccctg gtagtccacg ccgtaaacga tgaataacta ggtgtcgggt ggcaaagcca    780

ttcggtgccg tcgcaaacgc agtaagtatt ccacctgggg agtacgttcg caagaatgaa    840

actcaaagga attgacgggg acccgcacaa gcggtggagc atgtggttta attcgaagca    900

acgcgaagaa ccttaccaag tcttgacatc cgcctgaccg atccttaacc ggatctttcc    960

ttcgggacag gcgagacagg tggtgcatgg ttgtcgtcag ctcgtgtcgt gagatgttgg   1020

gttaagtccc gcaacgagcg caacccctat cctcagtagc cagcatttaa ggtgggcact   1080

ctggggagac tgccagggat aacctggagg aaggcgggga tgacgtcaaa tcatcatgcc   1140

ccttatgatt tgggctacac acgtgctaca atggcgtaaa caaagggaag cgagattgtg   1200

agatggagca aatcccaaaa ataacgtccc agttcggact gtagtctgca acccgactac   1260

acgaagctgg aatcgctagt aatcgcggat cagaatgccg cggtgaatac gttcccgggt   1320

cttgtacaca ccgcccgtca caccatggga gtcagtaacg cccgaagtca gtgacctaac   1380

tgcaaagaag gagctgccga aggcgggacc gatgactggg gtgaagtcgt aacaaggt     1438


<210> SEQ ID NO 3
<211> LENGTH: 1481
<212> TYPE: DNA
<213> ORGANISM: Blautia stercoris
<220> FEATURE:
<221> NAME/KEY: modified base
<222> LOCATION: 4
<223> OTHER INFORMATION: 'k' is g or t

<400> SEQUENCE: 3

tttkgtctgg ctcaggatga acgctggcgg cgtgcttaac acatgcaagt cgagcgaagc     60

gcttacgaca gaaccttcgg gggaagatgt aagggactga gcggcggacg ggtgagtaac    120

gcgtgggtaa cctgcctcat acagggggat aacagttgga aacggctgct aataccgcat    180

aagcgcacag tatcgcatga tacagtgtga aaaactccgg tggtatgaga tggacccgcg    240

tctgattagc tagttggagg ggtaacggcc caccaaggcg acgatcagta gccggcctga    300

gagggtgaac ggccacattg ggactgagac acggcccaga ctcctacggg aggcagcagt    360

ggggaatatt gcacaatggg ggaaaccctg atgcagcgac gccgcgtgaa ggaagaagta    420

tctcggtatg taaacttcta tcagcaggga agaaaatgac ggtacctgac taagaagccc    480

cggctaacta cgtgccagca gccgcggtaa tacgtagggg gcaagcgtta tccggattta    540

ctgggtgtaa agggagcgta gacggaagag caagtctgat gtgaaaggct ggggcttaac    600

cccaggactg cattggaaac tgtttttctt gagtgccgga gaggtaagcg gaattcctag    660

tgtagcggtg aaatgcgtag atattaggag gaacaccagt ggcgaaggcg gcttactgga    720

cggtaactga cgttgaggct cgaaagcgtg gggagcaaac aggattagat accctggtag    780

tccacgccgt aaacgatgaa tactaggtgt tggggagcaa agctcttcgg tgccgcagca    840

aacgcaataa gtattccacc tggggagtac gttcgcaaga atgaaactca aaggaattga    900

cggggacccg cacaagcggt ggagcatgtg gtttattcga agcaacgcga agaaccttac    960

caagtcttga catcgatctg accggttcgt aatggaacct ttccttcggg acagagaaga   1020

caggtggtgc atggttgtcg tcagctcgtg tcgtgagatg ttgggttaag tcccgcaacg   1080

agcgcaaccc ctatcgtcag tagccagcag gtaaagctgg gcactctgag gagactgcca   1140

gggataacct ggaggaaggc ggggacgacg tcaaatcatc atgcccctta tgatttgggc   1200

tacacacgtg ctacaatggc gtaaacaaag ggaagcgagc ccgcgagggg gagcaaatcc   1260
```

caaaaataac gtcccagttc ggactgcagt ctgcaactcg actgcacgaa gctggaatcg 1320
ctagtaatcg cgaatcagaa tgtcgcggtg aatacgttcc cgggtcttgt acacaccgcc 1380
cgtcacacca tgggagtcag taacgcccga agtcagtgac ccaaccttag ggagggagct 1440
gccgaaggcg ggattgataa ctggggtgaa gtctaggggg t 1481

<210> SEQ ID NO 4
<211> LENGTH: 1384
<212> TYPE: DNA
<213> ORGANISM: Blautia wexlerae
<220> FEATURE:
<221> NAME/KEY: modified base
<222> LOCATION: 749
<223> OTHER INFORMATION: 'n' is a, c, g or t

<400> SEQUENCE: 4
ttcattgaga cttcggtgga tttagattct atttctagtg gcggacgggt gagtaacgcg 60
tgggtaacct gccttataca gggggataac agtcagaaat ggctgctaat accgcataag 120
cgcacagagc tgcatggctc agtgtgaaaa actccggtgg tataagatgg acccgcgttg 180
gattagcttg ttggtggggt aacggcccac caaggcgacg atccatagcc ggcctgagag 240
ggtgaacggc cacattggga ctgagacacg gcccagactc ctacgggagg cagcagtggg 300
gaatattgca caatggggga aaccctgatg cagcgacgcc gcgtgaagga agaagtatct 360
cggtatgtaa acttctatca gcagggaaga tagtgacggt acctgactaa gaagccccgg 420
ctaactacgt gccagcagcc gcggtaatac gtagggggca agcgttatcc ggatttactg 480
ggtgtaaagg gagcgtagac ggtgtggcaa gtctgatgtg aaaggcatgg gctcaacctg 540
tggactgcat tggaaactgt catacttgag tgccggaggg gtaagcggaa ttcctagtgt 600
agcggtgaaa tgcgtagata ttaggaggaa caccagtggc gaaggcggct tactggacgg 660
taactgacgt tgaggctcga aagcgtgggg agcaaacagg attagatacc ctggtagtcc 720
acgccgtaaa cgatgaatac taggtgtcng gggagcatgg ctcttcggtg ccgtcgcaaa 780
cgcagtaagt attccacctg gggagtacgt tcgcaagaat gaaactcaaa ggaattgacg 840
gggacccgca caagcggtgg agcatgtggt ttaattcgaa gcaacgcgaa gaaccttacc 900
aagtcttgac atccgcctga ccgatcctta accggatctt tccttcggga caggcgagac 960
aggtggtgca tggttgtcgt cagctcgtgt cgtgagatgt tgggttaagt cccgcaacga 1020
gcgcaacccc tatcctcagt agccagcatt taaggtgggc actctgggga gactgccagg 1080
gataacctgg aggaaggcgg ggatgacgtc aaatcatcat gccccttatg atttgggcta 1140
cacacgtgct acaatggcgt aaacaaaggg aagcgagatc gtgagatgga gcaaatccca 1200
aaaataacgt cccagttcgg actgtagtct gcaacccgac tacacgaagc tggaatcgct 1260
agtaatcgcg gatcagaatg ccgcggtgaa tacgttcccg ggtcttgtac acaccgcccg 1320
tcacaccatg ggagtcagta acgcccgaag tcagtgacct aactgcaaag aaggagctgc 1380
cgaa 1384

<210> SEQ ID NO 5
<211> LENGTH: 1458
<212> TYPE: DNA
<213> ORGANISM: Blautia hydrogenotrophica
<220> FEATURE:
<221> NAME/KEY: modified base
<222> LOCATION: 1416
<223> OTHER INFORMATION: 'n' is a, c, g or t -continued

```
<400> SEQUENCE: 5

gatgaacgct ggcggcgtgc ttaacacatg caagtcgaac gaagcgatag agaacggaga     60

tttcggttga agttttctat tgactgagtg gcggacgggt gagtaacgcg tgggtaacct    120

gccctataca gggggataac agttagaaat gactgctaat accgcataag cgcacagctt    180

cgcatgaagc ggtgtgaaaa actgaggtgg tataggatgg acccgcgttg gattagctag    240

ttggtgaggt aacggcccac caaggcgacg atccatagcc ggcctgagag ggtgaacggc    300

cacattggga ctgagacacg gcccaaactc ctacgggagg cagcagtggg gaatattgca    360

caatggggga aaccctgatg cagcgacgcc gcgtgaagga agaagtatct cggtatgtaa    420

acttctatca gcagggaaga aagtgacggt acctgactaa gaagccccgg ctaattacgt    480

gccagcagcc gcggtaatac gtaaggggca agcgttatcc ggatttactg ggtgtaaagg    540

gagcgtagac ggtttggcaa gtctgatgtg aaaggcatgg gctcaacctg tggactgcat    600

tggaaactgt cagacttgag tgccggagag gcaagcggaa ttcctagtgt agcggtgaaa    660

tgcgtagata ttaggaggaa caccagtggc gaaggcggcc tgctggacgg taactgacgt    720

tgaggctcga aagcgtgggg agcaaacagg attagatacc ctggtagtcc acgctgtaaa    780

cgatgaatac taggtgtcgg gtggcaaagc cattcggtgc cgcagcaaac gcaataagta    840

ttcccacctg gggagtacgt tcgcaagaat gaaactcaaa ggaattgacg gggacccgca    900

caagcggtgg agcatgtggt ttaattcgaa gcaacgcgaa gaaccttacc aaatcttgac    960

atccctctga ccgggaagta atgttccctt ttcttcggaa cagaggagac aggtggtgca   1020

tggttgtcgt cagctcgtgt cgtgagatgt tgggttaagt cccgcaacga gcgcaaccct   1080

tattcttagt agccagcagg tagagctggg cactctaggg agactgccag ggataacctg   1140

gaggaaggtg gggatgacgt caaatcatca tgccccttat gatttgggct acacacgtgc   1200

tacaatggcg taaacaaagg gaagcgaagg ggtgacctgg agcaaatctc aaaaataacg   1260

tctcagttcg gattgtagtc tgcaactcga ctacatgaag ctggaatcgc tagtaatcgc   1320

gaatcagaat gtcgcggtga atacgttccc gggtcttgta cacaccgccc gtcacaccat   1380

gggagtcagt aacgcccgaa gtcagtgacc caaccnaaag gagggagctg ccgaaggtgg   1440

gactgataac tggggtga                                                 1458
```